US012653668B2

(12) United States Patent
Levi et al.

(10) Patent No.: US 12,653,668 B2
(45) Date of Patent: Jun. 16, 2026

(54) PROSTHETIC HEART VALVES WITH H-SHAPED COMMISSURE WINDOWS AND METHODS FOR ASSEMBLY THEREOF

(71) Applicant: Edwards Lifesciences Corporation, Irvine, CA (US)

(72) Inventors: Tamir S. Levi, Zikhron Yaakov (IL); Itay Avinathan, Tel-Aviv (IL)

(73) Assignee: Edwards Lifesciences Corporation, Irvine, CA (US)

( * ) Notice: Subject to any disclaimer, the term of this patent is extended or adjusted under 35 U.S.C. 154(b) by 663 days.

(21) Appl. No.: 18/099,394

(22) Filed: Jan. 20, 2023

(65) Prior Publication Data

US 2023/0149159 A1 May 18, 2023

Related U.S. Application Data

(63) Continuation of application No. PCT/US2021/042161, filed on Jul. 19, 2021.
(Continued)

(51) Int. Cl.
*A61F 2/24* (2006.01)

(52) U.S. Cl.
CPC .......... *A61F 2/2418* (2013.01); *A61F 2/2415* (2013.01); *A61F 2220/0075* (2013.01); *A61F 2230/0039* (2013.01)

(58) Field of Classification Search
CPC .... A61F 2/2418; A61F 2/2427; A61F 2/2409; A61F 2/2412; A61F 2/91; A61F 2/9522; A61F 2/2445; A61F 2/24; A61F 2/82; A61F 2/856; A61F 2/86; A61F 2/97; A61F 2250/0069; A61F 2/246; A61F 2/2463; A61F 2/2439; A61F 2002/9511
See application file for complete search history.

(56) References Cited

U.S. PATENT DOCUMENTS

| | | |
|---|---|---|
| 3,409,013 A | 11/1968 | Henry |
| 3,548,417 A | 12/1970 | Kischer et al. |

(Continued)

FOREIGN PATENT DOCUMENTS

| | | | | | |
|---|---|---|---|---|---|
| CN | 111182856 A | * | 5/2020 | ........... | A61F 2/2418 |
| CN | 113164258 A | * | 7/2021 | ........... | A61L 31/148 |

(Continued)

*Primary Examiner* — Seema Mathew
(74) *Attorney, Agent, or Firm* — Klarquist Sparkman, LLP; Joel B. German

(57) ABSTRACT

Assembly methods for installing a valvular structure to an expandable annular frame of a prosthetic heart valve are described. The valvular structure has a multiple leaflets, each with a pair of tabs. Each tab of the leaflet has upper and lower portions. Commissures formed by paired tabs of adjacent leaflets are coupled to corresponding commissure windows to support the valvular structure within the frame. Each commissure window has upper and lower openings separated from each other by a crossbar and may have an H-shape. The upper and lower tab portions extend through the upper and lower openings, respectively, of the corresponding commissure window. One or more wedge members coupled to the tab portions can prevent the leaflet tab from passing back through the commissure window, thereby retaining the valvular structure to the annular frame.

21 Claims, 15 Drawing Sheets

Related U.S. Application Data

(60) Provisional application No. 63/054,394, filed on Jul. 21, 2020.

(56) References Cited

U.S. PATENT DOCUMENTS

| | | | |
|---|---|---|---|
| 3,587,115 A | 6/1971 | Shiley | |
| 3,657,744 A | 4/1972 | Ersek | |
| 3,671,979 A | 6/1972 | Moulopoulos | |
| 3,714,671 A | 2/1973 | Goodenough et al. | |
| 3,755,823 A | 9/1973 | Hancock | |
| 4,035,849 A | 7/1977 | Angell et al. | |
| 4,056,854 A | 11/1977 | Boretos et al. | |
| 4,106,129 A | 8/1978 | Carpentier et al. | |
| 4,222,126 A | 9/1980 | Boretos et al. | |
| 4,265,694 A | 5/1981 | Boretos et al. | |
| 4,297,749 A | 11/1981 | Davis et al. | |
| RE30,912 E | 4/1982 | Hancock | |
| 4,339,831 A | 7/1982 | Johnson | |
| 4,343,048 A | 8/1982 | Ross et al. | |
| 4,345,340 A | 8/1982 | Rosen | |
| 4,373,216 A | 2/1983 | Klawitter | |
| 4,406,022 A | 9/1983 | Roy | |
| 4,441,216 A | 4/1984 | Ionescu et al. | |
| 4,470,157 A | 9/1984 | Love | |
| 4,535,483 A | 8/1985 | Klawitter et al. | |
| 4,574,803 A | 3/1986 | Storz | |
| 4,592,340 A | 6/1986 | Boyles | |
| 4,605,407 A | 8/1986 | Black et al. | |
| 4,612,011 A | 9/1986 | Kautzky | |
| 4,643,732 A | 2/1987 | Pietsch et al. | |
| 4,655,771 A | 4/1987 | Wallsten | |
| 4,692,164 A | 9/1987 | Dzemeshkevich et al. | |
| 4,733,665 A | 3/1988 | Palmaz | |
| 4,759,758 A | 7/1988 | Gabbay | |
| 4,762,128 A | 8/1988 | Rosenbluth | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |
| 4,820,299 A | 4/1989 | Philippe et al. | |
| 4,829,990 A | 5/1989 | Thuroff et al. | |
| 4,851,001 A | 7/1989 | Taheri | |
| 4,856,516 A | 8/1989 | Hillstead | |
| 4,878,495 A | 11/1989 | Grayzel | |
| 4,878,906 A | 11/1989 | Lindemann et al. | |
| 4,883,458 A | 11/1989 | Shiber | |
| 4,922,905 A | 5/1990 | Strecker | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Samuels | |
| 5,059,177 A | 10/1991 | Towne et al. | |
| 5,080,668 A | 1/1992 | Bolz et al. | |
| 5,085,635 A | 2/1992 | Cragg | |
| 5,089,015 A | 2/1992 | Ross | |
| 5,152,771 A | 10/1992 | Sabbaghian et al. | |
| 5,163,953 A | 11/1992 | Vince | |
| 5,167,628 A | 12/1992 | Boyles | |
| 5,192,297 A | 3/1993 | Hull | |
| 5,266,073 A | 11/1993 | Wall | |
| 5,282,847 A | 2/1994 | Trescony et al. | |
| 5,295,958 A | 3/1994 | Shturman | |
| 5,332,402 A | 7/1994 | Teitelbaum | |
| 5,360,444 A | 11/1994 | Kusuhara | |
| 5,370,685 A | 12/1994 | Stevens | |
| 5,397,351 A | 3/1995 | Pavcnik et al. | |
| 5,411,055 A | 5/1995 | Kane | |
| 5,411,552 A | 5/1995 | Andersen et al. | |
| 5,443,446 A | 8/1995 | Shturman | |
| 5,480,424 A | 1/1996 | Cox | |
| 5,500,014 A | 3/1996 | Quijano et al. | |
| 5,545,209 A | 8/1996 | Roberts et al. | |
| 5,545,214 A | 8/1996 | Stevens | |
| 5,549,665 A | 8/1996 | Vesely et al. | |
| 5,554,185 A | 9/1996 | Block et al. | |
| 5,558,644 A | 9/1996 | Boyd et al. | |
| 5,571,175 A | 11/1996 | Vanney et al. | |
| 5,584,803 A | 12/1996 | Stevens et al. | |
| 5,591,185 A | 1/1997 | Kilmer et al. | |
| 5,591,195 A | 1/1997 | Taheri et al. | |
| 5,607,464 A | 3/1997 | Trescony et al. | |
| 5,609,626 A | 3/1997 | Quijano et al. | |
| 5,628,792 A | 5/1997 | Lentell | |
| 5,639,274 A | 6/1997 | Fischell et al. | |
| 5,665,115 A | 9/1997 | Cragg | |
| 5,716,417 A | 2/1998 | Girard et al. | |
| 5,728,068 A | 3/1998 | Leone et al. | |
| 5,749,890 A | 5/1998 | Shaknovich | |
| 5,756,476 A | 5/1998 | Epstein et al. | |
| 5,769,812 A | 6/1998 | Stevens et al. | |
| 5,800,508 A | 9/1998 | Goicoechea et al. | |
| 5,840,081 A | 11/1998 | Andersen et al. | |
| 5,855,597 A | 1/1999 | Jayaraman | |
| 5,855,601 A | 1/1999 | Bessler et al. | |
| 5,855,602 A | 1/1999 | Angell | |
| 5,925,063 A | 7/1999 | Khosravi | |
| 5,957,949 A | 9/1999 | Leonhardt et al. | |
| 6,027,525 A | 2/2000 | Suh et al. | |
| 6,132,473 A | 10/2000 | Williams et al. | |
| 6,168,614 B1 | 1/2001 | Andersen et al. | |
| 6,171,335 B1 | 1/2001 | Wheatley et al. | |
| 6,174,327 B1 | 1/2001 | Mertens et al. | |
| 6,210,408 B1 | 4/2001 | Chandrasekaran et al. | |
| 6,217,585 B1 | 4/2001 | Houser et al. | |
| 6,221,091 B1 | 4/2001 | Khosravi | |
| 6,231,602 B1 | 5/2001 | Carpentier et al. | |
| 6,245,102 B1 | 6/2001 | Jayaraman | |
| 6,254,636 B1* | 7/2001 | Peredo | A61F 2/2412 |
| | | | 623/2.15 |
| 6,299,637 B1 | 10/2001 | Shaolian et al. | |
| 6,302,906 B1 | 10/2001 | Goicoechea et al. | |
| 6,338,740 B1 | 1/2002 | Carpentier | |
| 6,350,277 B1 | 2/2002 | Kocur | |
| 6,352,547 B1 | 3/2002 | Brown et al. | |
| 6,425,916 B1 | 7/2002 | Garrison et al. | |
| 6,440,764 B1 | 8/2002 | Focht et al. | |
| 6,454,799 B1* | 9/2002 | Schreck | A61F 2/2433 |
| | | | 623/2.14 |
| 6,458,153 B1 | 10/2002 | Bailey et al. | |
| 6,461,382 B1 | 10/2002 | Cao | |
| 6,468,660 B2 | 10/2002 | Ogle et al. | |
| 6,482,228 B1 | 11/2002 | Norred | |
| 6,488,704 B1 | 12/2002 | Connelly et al. | |
| 6,527,979 B2 | 3/2003 | Constantz et al. | |
| 6,569,196 B1 | 5/2003 | Vesely | |
| 6,582,462 B1 | 6/2003 | Andersen et al. | |
| 6,605,112 B1 | 8/2003 | Moll et al. | |
| 6,689,123 B2 | 2/2004 | Pinchasik | |
| 6,716,244 B2 | 4/2004 | Klaco | |
| 6,730,118 B2 | 5/2004 | Spenser et al. | |
| 6,733,525 B2 | 5/2004 | Yang et al. | |
| 6,767,362 B2 | 7/2004 | Schreck | |
| 6,769,161 B2 | 8/2004 | Brown et al. | |
| 6,783,542 B2 | 8/2004 | Eidenschink | |
| 6,830,584 B1 | 12/2004 | Seguin | |
| 6,878,162 B2 | 4/2005 | Bales et al. | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,018,408 B2 | 3/2006 | Bailey et al. | |
| 7,096,554 B2 | 8/2006 | Austin et al. | |
| 7,225,518 B2 | 6/2007 | Eidenschink et al. | |
| 7,276,078 B2 | 10/2007 | Spenser et al. | |
| 7,316,710 B1 | 1/2008 | Cheng et al. | |
| 7,318,278 B2 | 1/2008 | Zhang et al. | |
| 7,374,571 B2 | 5/2008 | Pease et al. | |
| 7,393,360 B2 | 7/2008 | Spenser et al. | |
| 7,462,191 B2 | 12/2008 | Spenser et al. | |
| 7,585,321 B2 | 9/2009 | Cribier | |

(56) References Cited

U.S. PATENT DOCUMENTS

| | | | |
|---|---|---|---|
| 7,618,446 B2 | 11/2009 | Andersen et al. | |
| 7,785,366 B2 | 8/2010 | Maurer et al. | |
| 7,959,665 B2 | 6/2011 | Pienknagura | |
| 7,959,672 B2 | 6/2011 | Salahieh et al. | |
| 7,993,394 B2 | 8/2011 | Hariton et al. | |
| 8,029,556 B2 | 10/2011 | Rowe | |
| 8,075,611 B2 | 12/2011 | Millwee et al. | |
| 8,128,686 B2 | 3/2012 | Paul, Jr. et al. | |
| 8,167,932 B2 | 5/2012 | Bourang et al. | |
| 8,317,858 B2* | 11/2012 | Straubinger | A61F 2/82 |
| | | | 623/2.12 |
| 8,348,998 B2 | 1/2013 | Pintor et al. | |
| 8,449,606 B2 | 5/2013 | Eliasen et al. | |
| 8,652,203 B2 | 2/2014 | Quadri et al. | |
| 8,685,055 B2 | 4/2014 | Vantassel et al. | |
| 8,747,463 B2 | 6/2014 | Fogarty et al. | |
| 9,615,920 B2* | 4/2017 | Alkhatib | A61F 2/2415 |
| 11,109,963 B2* | 9/2021 | Dienno | A61F 2/2433 |
| 11,207,175 B2* | 12/2021 | Yohanan | A61F 2/2433 |
| 11,224,509 B2 | 1/2022 | Dasi et al. | |
| 11,382,738 B2* | 7/2022 | Tian | A61F 2/2433 |
| 11,439,502 B2* | 9/2022 | Busalacchi | A61F 2/2412 |
| 11,589,981 B2* | 2/2023 | Girard | A61F 2/2418 |
| 11,850,148 B2* | 12/2023 | Levi | A61F 2/2418 |
| 11,883,281 B2* | 1/2024 | Hoang | A61F 2/0077 |
| 11,938,021 B2* | 3/2024 | Tzadok | A61F 2/2418 |
| 11,980,544 B2* | 5/2024 | Chang | A61F 2/2418 |
| 12,011,349 B2* | 6/2024 | Peterson | A61F 2/9522 |
| 12,023,241 B2* | 7/2024 | Gao | A61F 2/2418 |
| 12,029,644 B2* | 7/2024 | Gurovich | A61F 2/2418 |
| 12,201,520 B2* | 1/2025 | Bennett | A61F 2/2418 |
| 12,268,596 B2* | 4/2025 | Dasi | A61L 27/18 |
| 12,427,013 B2* | 9/2025 | Bukin | A61F 2/2415 |
| 2001/0021872 A1 | 9/2001 | Bailey et al. | |
| 2002/0026094 A1 | 2/2002 | Roth | |
| 2002/0032481 A1 | 3/2002 | Gabbay | |
| 2002/0138135 A1 | 9/2002 | Duerig et al. | |
| 2002/0143390 A1 | 10/2002 | Ishii | |
| 2002/0173842 A1 | 11/2002 | Buchanan | |
| 2003/0040791 A1 | 2/2003 | Oktay | |
| 2003/0050694 A1 | 3/2003 | Yang et al. | |
| 2003/0100939 A1 | 5/2003 | Yodfat et al. | |
| 2003/0158597 A1 | 8/2003 | Quiachon et al. | |
| 2003/0212454 A1 | 11/2003 | Scott et al. | |
| 2004/0024452 A1 | 2/2004 | Kruse et al. | |
| 2004/0039436 A1 | 2/2004 | Spenser et al. | |
| 2004/0078074 A1 | 4/2004 | Anderson et al. | |
| 2004/0186558 A1 | 9/2004 | Pavcnik et al. | |
| 2004/0186563 A1* | 9/2004 | Lobbi | A61F 2/2418 |
| | | | 623/2.11 |
| 2004/0186565 A1 | 9/2004 | Schreck | |
| 2004/0260389 A1 | 12/2004 | Case et al. | |
| 2005/0010285 A1 | 1/2005 | Lambrecht et al. | |
| 2005/0075725 A1 | 4/2005 | Rowe | |
| 2005/0075728 A1 | 4/2005 | Nguyen et al. | |
| 2005/0096736 A1 | 5/2005 | Osse et al. | |
| 2005/0137686 A1 | 6/2005 | Salahieh et al. | |
| 2005/0188525 A1 | 9/2005 | Weber et al. | |
| 2005/0203614 A1 | 9/2005 | Forster et al. | |
| 2005/0234546 A1 | 10/2005 | Nugent et al. | |
| 2006/0004469 A1 | 1/2006 | Sokel | |
| 2006/0025857 A1 | 2/2006 | Bergheim et al. | |
| 2006/0058872 A1 | 3/2006 | Salahieh et al. | |
| 2006/0074484 A1 | 4/2006 | Huber | |
| 2006/0108090 A1 | 5/2006 | Ederer et al. | |
| 2006/0149350 A1 | 7/2006 | Patel et al. | |
| 2006/0183383 A1 | 8/2006 | Asmus et al. | |
| 2006/0195184 A1* | 8/2006 | Lane | A61F 2/2418 |
| | | | 623/2.38 |
| 2006/0229719 A1 | 10/2006 | Marquez et al. | |
| 2006/0259136 A1 | 11/2006 | Nguyen et al. | |
| 2006/0259137 A1 | 11/2006 | Artof et al. | |
| 2006/0287717 A1 | 12/2006 | Rowe et al. | |
| 2007/0005131 A1 | 1/2007 | Taylor | |
| 2007/0010876 A1 | 1/2007 | Salahieh et al. | |
| 2007/0010877 A1 | 1/2007 | Salahieh et al. | |
| 2007/0112422 A1 | 5/2007 | Dehdashtian et al. | |
| 2007/0162102 A1 | 7/2007 | Ryan et al. | |
| 2007/0203503 A1 | 8/2007 | Salahieh et al. | |
| 2007/0203575 A1 | 8/2007 | Forster et al. | |
| 2007/0203576 A1 | 8/2007 | Lee et al. | |
| 2007/0208550 A1 | 9/2007 | Cao et al. | |
| 2007/0213813 A1 | 9/2007 | Von Segesser et al. | |
| 2007/0233228 A1 | 10/2007 | Eberhardt et al. | |
| 2007/0260305 A1 | 11/2007 | Drews et al. | |
| 2007/0265700 A1 | 11/2007 | Eliasen et al. | |
| 2008/0021546 A1 | 1/2008 | Patz et al. | |
| 2008/0114442 A1 | 5/2008 | Mitchell et al. | |
| 2008/0125853 A1 | 5/2008 | Bailey et al. | |
| 2008/0154355 A1 | 6/2008 | Benichou et al. | |
| 2008/0183271 A1 | 7/2008 | Frawley et al. | |
| 2008/0208327 A1* | 8/2008 | Rowe | A61F 2/2427 |
| | | | 604/509 |
| 2008/0243245 A1 | 10/2008 | Thambar et al. | |
| 2008/0255660 A1 | 10/2008 | Guyenot et al. | |
| 2008/0275537 A1 | 11/2008 | Limon | |
| 2008/0294248 A1 | 11/2008 | Yang et al. | |
| 2009/0118826 A1 | 5/2009 | Khaghani | |
| 2009/0125118 A1 | 5/2009 | Gong | |
| 2009/0157175 A1 | 6/2009 | Benichou | |
| 2009/0216312 A1* | 8/2009 | Straubinger | A61F 2/2418 |
| | | | 623/1.36 |
| 2009/0276040 A1 | 11/2009 | Rowe et al. | |
| 2009/0281619 A1 | 11/2009 | Le et al. | |
| 2009/0287296 A1 | 11/2009 | Manasse | |
| 2009/0287299 A1 | 11/2009 | Tabor et al. | |
| 2009/0299452 A1 | 12/2009 | Eidenschink et al. | |
| 2009/0319037 A1 | 12/2009 | Rowe et al. | |
| 2010/0004735 A1 | 1/2010 | Yang et al. | |
| 2010/0049313 A1 | 2/2010 | Alon et al. | |
| 2010/0082094 A1 | 4/2010 | Quadri et al. | |
| 2010/0100176 A1 | 4/2010 | Elizondo et al. | |
| 2010/0168844 A1 | 7/2010 | Toomes et al. | |
| 2010/0185277 A1 | 7/2010 | Braido et al. | |
| 2010/0198347 A1 | 8/2010 | Zakay et al. | |
| 2010/0204781 A1 | 8/2010 | Alkhatib | |
| 2011/0015729 A1 | 1/2011 | Jimenez et al. | |
| 2011/0022157 A1 | 1/2011 | Essinger et al. | |
| 2011/0066224 A1 | 3/2011 | White | |
| 2011/0137397 A1 | 6/2011 | Chau et al. | |
| 2011/0218619 A1 | 9/2011 | Benichou et al. | |
| 2011/0319991 A1 | 12/2011 | Hariton et al. | |
| 2012/0030090 A1 | 2/2012 | Johnston et al. | |
| 2012/0078357 A1* | 3/2012 | Conklin | A61F 2/243 |
| | | | 623/2.18 |
| 2012/0089223 A1 | 4/2012 | Nguyen et al. | |
| 2012/0101571 A1 | 4/2012 | Thambar et al. | |
| 2012/0123529 A1 | 5/2012 | Levi et al. | |
| 2013/0023984 A1* | 1/2013 | Conklin | A61F 2/2418 |
| | | | 623/2.14 |
| 2013/0023985 A1 | 1/2013 | Khairkhahan et al. | |
| 2013/0046373 A1 | 2/2013 | Cartledge et al. | |
| 2013/0073030 A1* | 3/2013 | Tuval | A61F 2/2436 |
| | | | 623/2.18 |
| 2013/0096674 A1* | 4/2013 | Lobbi | A61F 2/2427 |
| | | | 623/2.19 |
| 2013/0150956 A1 | 6/2013 | Yohanan et al. | |
| 2013/0166017 A1 | 6/2013 | Cartledge et al. | |
| 2013/0190857 A1 | 7/2013 | Mitra et al. | |
| 2013/0274873 A1 | 10/2013 | Delaloye et al. | |
| 2013/0310926 A1 | 11/2013 | Hariton | |
| 2013/0331929 A1 | 12/2013 | Mitra et al. | |
| 2014/0194981 A1 | 7/2014 | Menk et al. | |
| 2014/0200661 A1 | 7/2014 | Pintor et al. | |
| 2014/0209238 A1 | 7/2014 | Bonyuet et al. | |
| 2014/0222136 A1 | 8/2014 | Geist et al. | |
| 2014/0277417 A1 | 9/2014 | Schraut et al. | |
| 2014/0277419 A1 | 9/2014 | Garde et al. | |
| 2014/0277424 A1 | 9/2014 | Oslund | |
| 2014/0277563 A1 | 9/2014 | White | |
| 2014/0296962 A1 | 10/2014 | Cartledge et al. | |
| 2014/0330372 A1 | 11/2014 | Weston et al. | |
| 2014/0343670 A1 | 11/2014 | Bakis et al. | |
| 2014/0343671 A1 | 11/2014 | Yohanan et al. | |

(56)                    References Cited

U.S. PATENT DOCUMENTS

| | | | |
|---|---|---|---|
| 2014/0350667 A1 | 11/2014 | Braido et al. | |
| 2015/0073545 A1 | 3/2015 | Braido | |
| 2015/0073546 A1 | 3/2015 | Braido | |
| 2015/0135506 A1 | 5/2015 | White | |
| 2015/0142103 A1* | 5/2015 | Vidlund | A61F 2/2439 |
| | | | 623/2.17 |
| 2015/0157455 A1 | 6/2015 | Hoang et al. | |
| 2016/0175096 A1* | 6/2016 | Dienno | A61F 2/2412 |
| | | | 623/2.13 |
| 2016/0228243 A1* | 8/2016 | Braido | A61F 2/2412 |
| 2016/0270910 A1* | 9/2016 | Birmingham | A61F 2/90 |
| 2016/0278922 A1* | 9/2016 | Braido | A61F 2/89 |
| 2017/0014229 A1 | 1/2017 | Nguyen-Thien-Nhon et al. | |
| 2018/0028310 A1 | 2/2018 | Gurovich et al. | |
| 2018/0153689 A1 | 6/2018 | Maimon et al. | |
| 2018/0325665 A1* | 11/2018 | Gurovich | A61F 2/2418 |
| 2018/0344456 A1 | 12/2018 | Barash et al. | |
| 2019/0125528 A1* | 5/2019 | Busalacchi | A61F 2/2427 |
| 2019/0125530 A1* | 5/2019 | Arcaro | A61F 2/2412 |
| 2020/0000586 A1* | 1/2020 | Tian | A61F 2/2445 |
| 2020/0138573 A1* | 5/2020 | Shang | A61L 27/3633 |
| 2022/0110749 A1* | 4/2022 | Hariton | A61F 2/2418 |
| 2022/0192824 A1* | 6/2022 | Vidlund | A61F 2/2418 |
| 2023/0149162 A1* | 5/2023 | Gurovich | A61F 2/2418 |
| | | | 623/2.17 |
| 2023/0414349 A1* | 12/2023 | Kovalsky | A61F 2/2418 |
| 2024/0180696 A1* | 6/2024 | Bukin | A61F 2/2418 |
| 2024/0285399 A1* | 8/2024 | O'Dell | A61L 31/022 |
| 2024/0293227 A1* | 9/2024 | Kuske | A61F 2/2418 |
| 2024/0398558 A1* | 12/2024 | Tuval | A61F 2/24 |
| 2025/0032248 A1* | 1/2025 | Baldwin | A61F 2/2418 |
| 2025/0213354 A1* | 7/2025 | Yohanan | A61F 2/2418 |
| 2025/0228663 A1* | 7/2025 | Haynes | A61F 2/2418 |
| 2025/0288415 A1* | 9/2025 | Bukin | A61F 2/243 |

FOREIGN PATENT DOCUMENTS

| | | | | | |
|---|---|---|---|---|---|
| JP | 2024525974 A | * | 7/2024 | | A61L 31/022 |
| WO | WO-2012048035 A2 | * | 4/2012 | | A61F 2/2433 |
| WO | WO-2016196933 A1 | * | 12/2016 | | A61F 2/243 |
| WO | WO-2022020229 A1 | * | 1/2022 | | A61F 2/2415 |
| WO | WO-2025046450 A1 | * | 3/2025 | | A61F 2/2418 |
| WO | WO-2025193686 A1 | * | 9/2025 | | A61F 2/2418 |
| WO | WO-2025193854 A1 | * | 9/2025 | | A61F 2/2418 |
| WO | WO-2025221856 A1 | * | 10/2025 | | A61F 2/2418 |

* cited by examiner

PROSTHETIC HEART VALVES WITH H-SHAPED COMMISSURE WINDOWS AND METHODS FOR ASSEMBLY THEREOF

CROSS-REFERENCE TO RELATED APPLICATIONS

This application is a continuation of PCT Application No. PCT/US2021/042161, filed Jul. 19, 2021, which claims the benefit of U.S. Provisional Application No. 63/054,394, filed Jul. 21, 2020, all of which are incorporated by reference herein.

FIELD

The present disclosure relates to prosthetic heart valves, and to methods and assemblies for forming and installing leaflet assemblies to frames of such prosthetic heart valves.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted, actuating a mechanical actuator that applies an expansion force to the prosthetic valve, or by deploying the prosthetic valve from a sheath of the delivery device so that the prosthetic valve can self-expand to its functional size. Prosthetic valves that rely on a mechanical actuator for expansion can be referred to as "mechanically expandable" prosthetic heart valves. The actuator typically takes the form of pull cables, sutures, wires and/or shafts that are configured to transmit expansion forces from a handle of the delivery apparatus to the prosthetic valve.

Expandable, transcatheter heart valves can comprise an annular metal frame or stent and prosthetic leaflets mounted inside the frame. The leaflets can be attached to a portion of the frame via commissure tab assemblies, for example, by passing through and/or wrapping around a commissure window. Each commissure tab assembly can be preassembled by connecting tabs of adjacent leaflets to each other and then attached by suture to commissure window. However, such commissure tab assemblies may be relatively complex and time-consuming to assemble. Moreover, certain configurations of the commissure window may suffer from reliability issues (e.g., due to undesirable changes in shape during expansion of the prosthetic heart valve) and/or commissure mounting problems.

Accordingly, a need exists for improved prosthetic heart valves and methods for securing leaflet assemblies to a frame of the prosthetic heart valve.

SUMMARY

Described herein are embodiments of prosthetic heart valves and methods for assembling prosthetic heart valves. A valvular structure, formed by a plurality of leaflets, is supported by an expandable annular frame of the prosthetic heart valve. Each leaflet can have a pair of tabs. In some embodiments, each tab can have upper and lower portions. Commissures formed by paired tabs of adjacent leaflets can be coupled to corresponding commissure windows to support the valvular structure within the frame. Each commissure window can have upper and lower openings or channels separated from each other by a crossbar. For example, each commissure window can be substantially H-shaped in respective side view, with the crossbar connecting between a pair of struts extending along an axial direction of the valve. A thickness of each axially-extending strut of the H-shaped commissure window and a location of the crossbar along the axial direction can be selected such that the H-shape does not deform, or experiences minimal deformation, as the frame transitions between fully-expanded and crimped states.

In some embodiments, the upper and lower tab portions can extend through the upper and lower openings, respectively, of the corresponding commissure window. In other embodiments, the paired tabs of a commissure extend through only one of the upper and lower openings of the corresponding commissure window. One or more wedge members can be coupled to the tab portions. The wedge member(s) can prevent the leaflet tab from passing back through the commissure window, thereby retaining the valvular structure to the annular frame. Embodiments of the disclosed subject matter may thus offer simple and cost-effective methods for reliably mounting the valvular structure to the frame of the prosthetic valve while avoiding stitching sutures (or at least reducing the impact thereof) through dynamic portions of the leaflets, thereby reducing the risk of leaflet tearing.

In one representative embodiment, an assembly method for a prosthetic heart valve is provided. The method can comprise providing first and second leaflets for a valvular structure of the prosthetic heart valve. Each leaflet can have a pair of tabs, and one of the tabs can be on an opposite side from the other of the tabs with respect to a centerline of the leaflet. Each tab can have an upper tab portion and a lower tab portion separated from the upper tab portion along a direction parallel to the centerline by a gap. The method can further comprise disposing the upper and lower tab portions of a second tab of the pair of tabs of the second leaflet adjacent to the upper and lower tab portions of a first tab of the pair of tabs of the first leaflet, respectively. The method can also comprise stitching together the upper tab portions of the first and second leaflet tabs, and stitching together the lower tab portions of the first and second leaflet tabs. The method can further comprise folding the upper and lower tab portions of the first leaflet tab. The method can also comprise conveying the first and second leaflet tabs through a commissure window of an expandable annular frame of the prosthetic heart valve. The commissure window can have upper and lower openings separated from each other along an axial direction of the annular frame by a crossbar. The conveying can be along a radial direction of the annular frame from a radially inner-side of the commissure window to a radially-outer side of the commissure window. The conveying can be such that the upper tab portions are inserted through the upper opening and the lower tab portions are inserted through the lower opening. The method can further comprise inserting one or more wedge members between facing surfaces of the folded upper tab portion of the first leaflet tab and between facing surfaces of the folded lower tab portion of the first leaflet tab. The method can also comprise folding the upper tab portion of the second leaflet tab around the folded upper tab portion of the first leaflet tab, and folding the lower tab portion of the second leaflet tab around the folded lower tab portion of the first leaflet tab. The method can further comprise stitching together the one or more wedge members and the upper tab portions of the first and second leaflet tabs, and stitching together the one or more wedge members and the lower tab portions of the first and second leaflet tabs.

In another representative embodiment, an assembly method for a prosthetic heart valve is provided. The method can comprise providing first and second leaflets for a valvular structure of the prosthetic heart valve. Each leaflet can have a pair of tabs, and one of the tabs can be on an opposite side from the other of the tabs with respect to a centerline of the leaflet. Each tab can have an upper tab portion and a lower tab portion separated from the upper tab portion along a direction parallel to the centerline by a gap. The method can further comprise disposing the upper tab portion of a first tab of the pair of tabs of the first leaflet to surround at least a portion of a circumference of a first wedge member, and disposing the lower tab portion of the first leaflet tab to surround at least a portion of a circumference of a second wedge member. The method can also comprise stitching together the first wedge member and at least the upper tab portion of the first leaflet tab, and stitching together the second wedge member and at least the lower tab portion of the first leaflet tab. The method can further comprise conveying the first wedge member, the second wedge member, and the first leaflet tab through a commissure window of an expandable annular frame of the prosthetic heart valve. The commissure window can have upper and lower openings separated from each other along an axial direction of the annular frame by a crossbar. The conveying can be along a radial direction of the annular frame from a radially inner-side of the commissure window to a radially-outer side of the commissure window. The conveying can be such that the upper tab portion of the first leaflet tab and the first wedge member are inserted through the upper opening and the lower tab portion of the first leaflet tab and the second wedge member are inserted through the lower opening. The method can also comprise conveying a second tab of the pair of tabs of the second leaflet through the commissure window. The conveying can be along the radial direction from the radially inner-side of the commissure window to the radially-outer side of the commissure window and such that the upper tab portion of the second leaflet tab is inserted through the upper opening and the lower tab portion of the second leaflet tab is inserted through the lower opening. The method can further comprise folding the upper tab portion of the second leaflet tab around the upper tab portion of the first leaflet tab, and folding the lower tab portion of the second leaflet tab around the lower tab portion of the first leaflet tab. The method can also comprise stitching together the first wedge member, and the upper tab portions of the first and second leaflet tabs, and stitching together the second wedge member and the lower tab portions of the first and second leaflet tabs.

In another representative embodiment, an assembly method for a prosthetic heart valve is provided. The method can comprise providing first and second leaflets for a valvular structure of the prosthetic heart valve. Each leaflet can have a pair of tabs, and one of the tabs can be on an opposite side from the other of the tabs with respect to a centerline of the leaflet. Each tab can have an upper tab portion and a lower tab portion separated from the upper tab portion along a direction parallel to the centerline by a gap. The method can further comprise conveying a first tab of the pair of tabs of the first leaflet through a commissure window of an expandable annular frame of the prosthetic heart valve, and conveying a second tab of the pair of tabs of the second leaflet through the commissure window. The commissure window can have upper and lower openings separated from each other along an axial direction of the annular frame by a crossbar. The conveying can be along a radial direction of the annular frame from a radially inner-side of the commissure window to a radially-outer side of the commissure window. The conveying can be such that the upper tab portions are inserted through the upper opening and the lower tab portions are inserted through the lower opening. The method can also comprise disposing the upper and lower tab portions of the first leaflet tab to surround at least a portion of a circumference of one or more wedge members. The method can further comprise folding the upper tab portion of the second leaflet tab around the upper tab portion of the first leaflet tab, and folding the lower tab portion of the second leaflet tab around the lower tab portion of the first leaflet tab. The method can also comprise stitching together the one or more wedge members and the upper tab portions of the first and second leaflet tabs, and stitching together the one or more wedge members and the lower tab portions of the first and second leaflet tabs.

In another representative embodiment, an assembly method for a prosthetic heart valve is provided. The method can comprise providing first and second leaflets for a valvular structure of the prosthetic heart valve. Each leaflet can have a pair of tabs, and one of the tabs can be on an opposite side from the other of the tabs with respect to a centerline of the leaflet. Each tab can have an upper tab portion and a lower tab portion separated from the upper tab portion along a direction parallel to the centerline by a gap. The method can further comprise disposing the upper tab portion of a first tab of the pair of tabs of the first leaflet to surround at least a portion of a circumference of a first wedge member. The method can also comprise stitching together the first wedge member and at least the upper tab portion of the first leaflet tab. The method can further comprise conveying a lower tab portion of the first leaflet tab through a commissure window of an expandable annular frame of the prosthetic heart valve. The commissure window can have upper and lower openings separated from each other along an axial direction of the annular frame by a crossbar. The conveying can be along a radial direction of the annular frame from a radially-inner side of the commissure window to a radially-outer side of the commissure window. The conveying can be such that the lower tab portion of the first leaflet tab extends through the lower opening. The method can also comprise conveying the first wedge member and the upper tab portion of the first leaflet tab from the radially-inner side of the commissure window through or over the upper opening of the commissure window to the radially-outer side of the commissure window, such that the upper tab portion of the first leaflet tab extends through the upper opening. The method can further comprise folding the lower tab portion of the first leaflet tab around the first wedge member. The method can also comprise conveying a second tab of the pair of tabs of the second leaflet through the commissure window. The conveying the second tab can be along the radial direction from the radially inner-side of the commissure window to the radially-outer side of the commissure window. The conveying the second tab can be such that the upper tab portion of the second leaflet tab is inserted through the upper opening and the lower tab portion of the second leaflet tab is inserted through the lower opening. The method can further comprise folding the upper tab portion of the second leaflet tab around the upper tab portion of the first leaflet tab, and folding the lower tab portion of the second leaflet tab around the lower tab portion of the first leaflet tab. The method can also comprise stitching together the first wedge member and the upper and lower tab portions of the first and second leaflet tabs.

In another representative embodiment, a prosthetic heart valve can comprise an expandable annular frame and a valvular structure. The expandable annular frame can have a plurality of commissure windows. The valvular structure can be coupled to the commissure windows. The valvular structure can comprise a plurality of leaflets. The tabs of adjacent leaflets can be coupled to a respective one of the commissure windows according to any of the disclosed assembly methods.

In another representative embodiment, a prosthetic heart valve can comprise an expandable annular frame and a valvular structure. The expandable annular frame can have a plurality of commissure windows. The valvular structure can comprise a plurality of leaflets. Each leaflet can have a pair of tabs, one of which can be on an opposite side from the other with respect to a centerline of the leaflet. Each tab can have an upper tab portion and a lower tab portion separated from the upper tab portion along a direction parallel to the centerline by a gap. The valvular structure can have a plurality of commissures formed by paired tabs of adjacent leaflets. Each commissure can be coupled to a corresponding one of the commissure windows to support the valvular structure within the annular frame. Each commissure window can have upper and lower openings separated from each other along an axial direction of the annular frame by a respective crossbar. The upper and lower tab portions for each tab can extend through the upper and lower openings, respectively, to a radially-outer side of the respective commissure window. The annular frame can be expandable between a crimped state having a first diameter and an expanded state having a second diameter greater than the first diameter.

The various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the invention will become more apparent from the following detailed description, which proceeds with reference to the accompanying figures.

DETAILED DESCRIPTION

Figure 1:
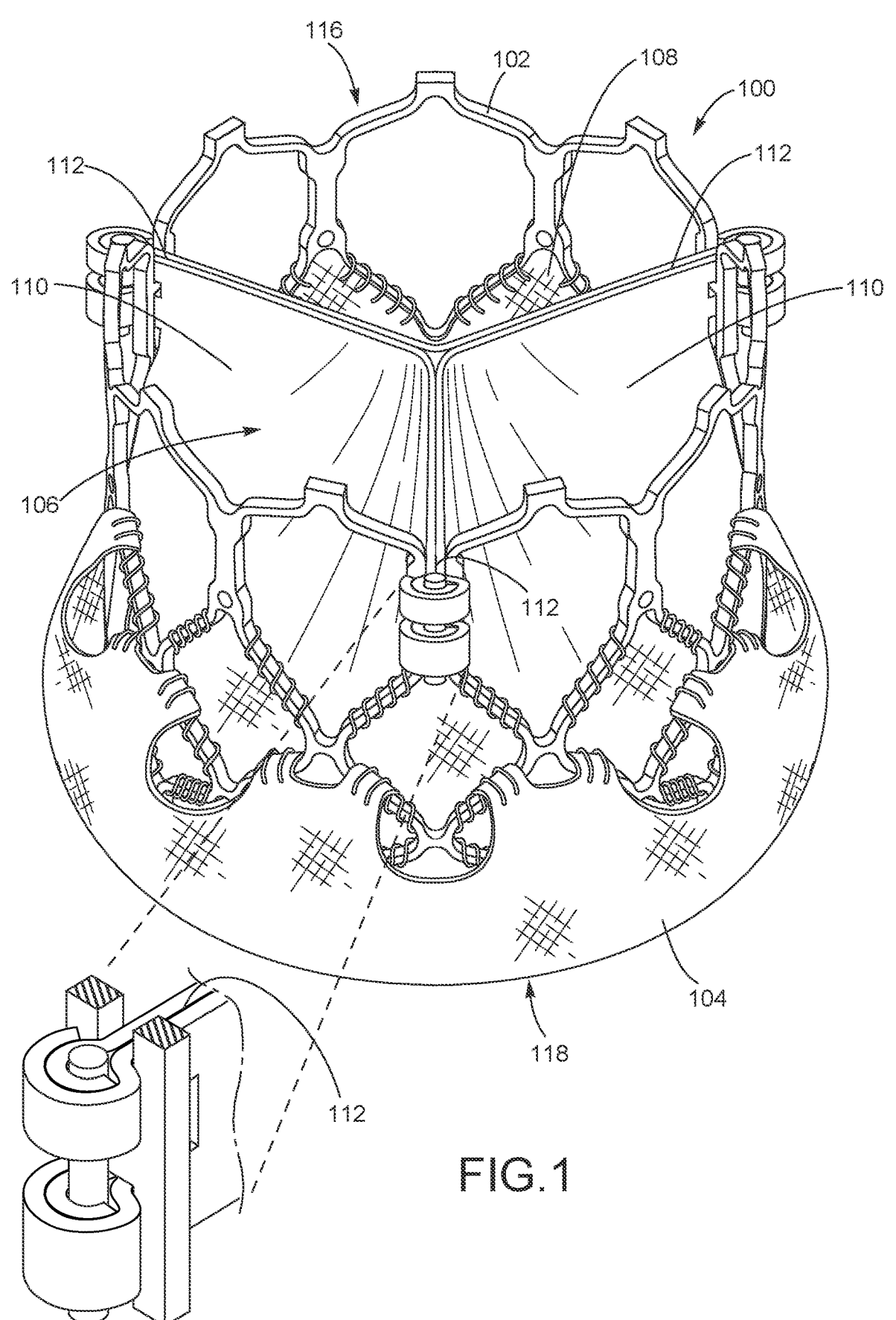
FIG. 1 is a perspective view of an exemplary prosthetic heart valve with H-shaped commissure windows.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present, or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used herein with reference to the prosthetic heart valve assembly and implantation and structures of the prosthetic heart valve, "proximal" refers to a position, direction, or portion of a component that is closer to the user and a handle of the delivery system that is outside the patient, while "distal" refers to a position, direction, or portion of a component that is further away from the user and the handle and closer to the implantation site. The terms "longitudinal" and "axial" refer to an axis extending in the proximal and distal directions, unless otherwise expressly defined.

The terms "axial direction," "radial direction," and "circumferential direction" have been used herein to describe the arrangement of components and assembly of commissures to respective windows, relative to the geometry of the frame of the prosthetic heart valve. Such terms have been used for convenient description, but the disclosed embodiments are not strictly limited to the description. In particular, where a component or action is described relative to a particular direction, directions parallel to the specified direction as well as minor deviations therefrom. Thus, a description of a component extending along an axial direction of the frame does not require the component to be aligned with a center of the frame; rather, the component can extend substantially along a direction parallel to a central axis of the frame.

As used herein, the terms "integrally formed" and "unitary construction" refer to a construction that does not include any welds, fasteners, or other means for securing separately formed pieces of material to each other.

As used herein, operations that occur "simultaneously" or "concurrently" occur generally at the same time as one another, although delays in the occurrence of operation relative to the other due to, for example, spacing between components, are expressly within the scope of the above terms, absent specific contrary language.

As used in this application and in the claims, the singular forms "a," "an," and "the" include the plural forms unless the context clearly dictates otherwise. Additionally, the terms "have" or "includes" means "comprises." Further, the terms "coupled" and "connected" generally mean electrically, electromagnetically, and/or physically (e.g., mechanically or chemically) coupled or linked and does not exclude the presence of intermediate elements between the coupled or associated items absent specific contrary language. As used herein, "and/or" means "and" or "or," as well as "and" and "or."

Directions and other relative references may be used to facilitate discussion of the drawings and principles herein, but are not intended to be limiting. For example, certain terms may be used such as "inner," "outer," "upper,"

"lower," "inside," "outside,", "top," "bottom," "interior," "exterior," "left," right," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same.

Described herein are examples of prosthetic heart valves, annular frames with commissure windows and leaflets for prosthetic heart valves, and methods for assembling leaflets to commissure windows of annular frames to form prosthetic heart valves. A valvular structure, which is formed by multiple leaflets, is supported by an expandable annular frame of the prosthetic heart valve. Each tab of the leaflet can have upper and lower portions separated from each other by a gap. Commissures formed by paired tabs of adjacent leaflets are coupled to corresponding commissure windows to support the valvular structure within the frame. Each commissure window can have upper and lower openings separated from each other by a crossbar. The upper and lower tab portions can extend through the upper and lower openings, respectively, of the corresponding commissure window. One or more wedge members coupled to the tab portions can prevent the leaflet tab from passing back through the commissure window, thereby retaining the valvular structure to the annular frame. As a result, a position of the leaflet assembly for a prosthetic heart valve may be effectively locked in place during assembly and use of the prosthetic heart valve, and a time and effort for securing the leaflet assembly to the frame of the prosthetic heart valve may be reduced.

In some embodiments, each commissure window can be substantially H-shaped in respective side view, with the crossbar connecting between a pair of struts extending along an axial direction of the valve. A thickness of each axially-extending strut of the H-shaped commissure window and a location of the crossbar along the axial direction can be selected such that the H-shape does not deform, or experiences minimal deformation, as the frame transitions between fully-expanded and crimped states, thereby reducing the risk of damage to the leaflets and/or detachment of the leaflets from the frame.

Figures 3A, 3B:
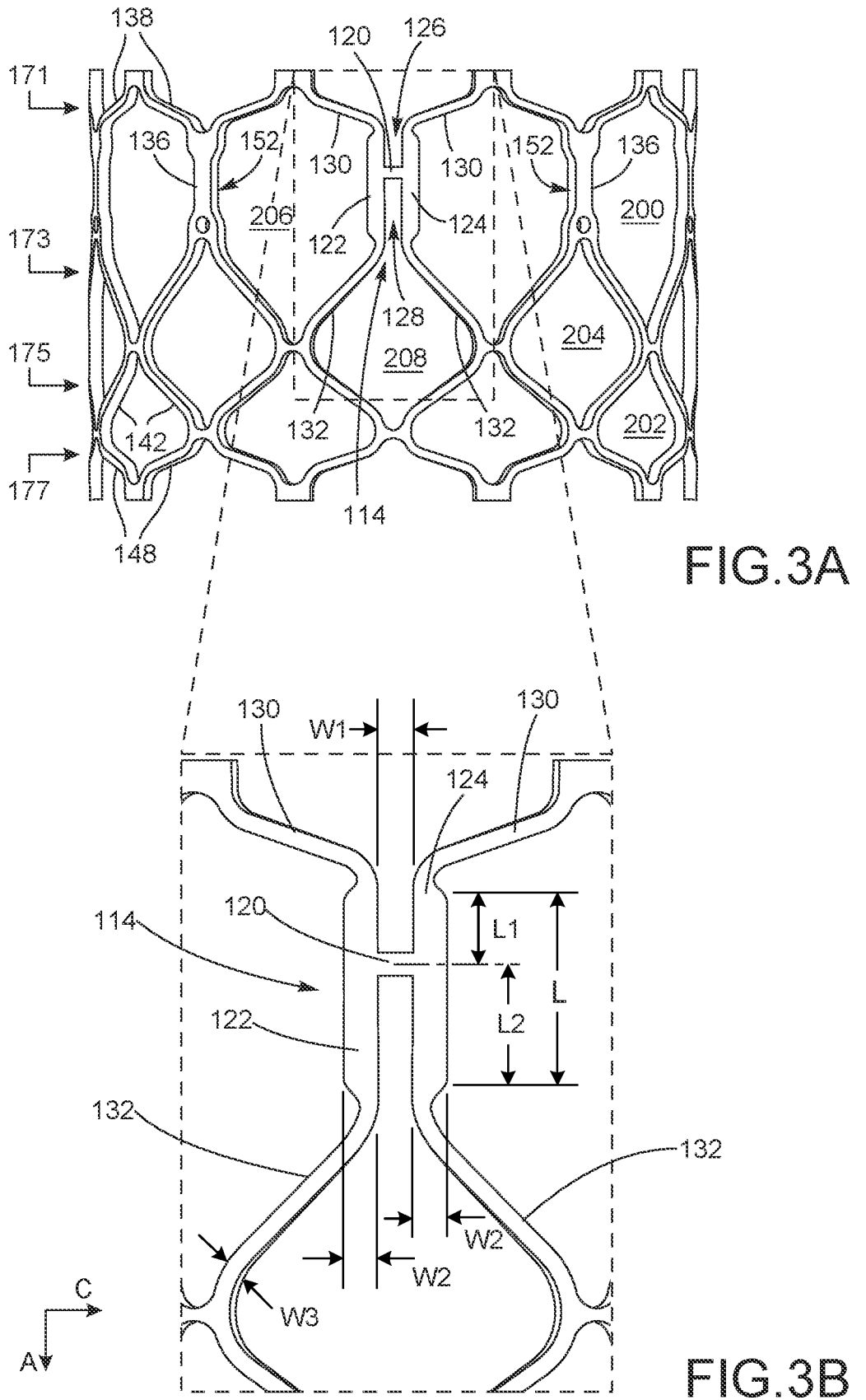
FIGS. 3A-3B are side and detail views, respectively, of an exemplary H-shaped commissure window of the prosthetic heart valve frame of FIG. 2.
Figure 3C:
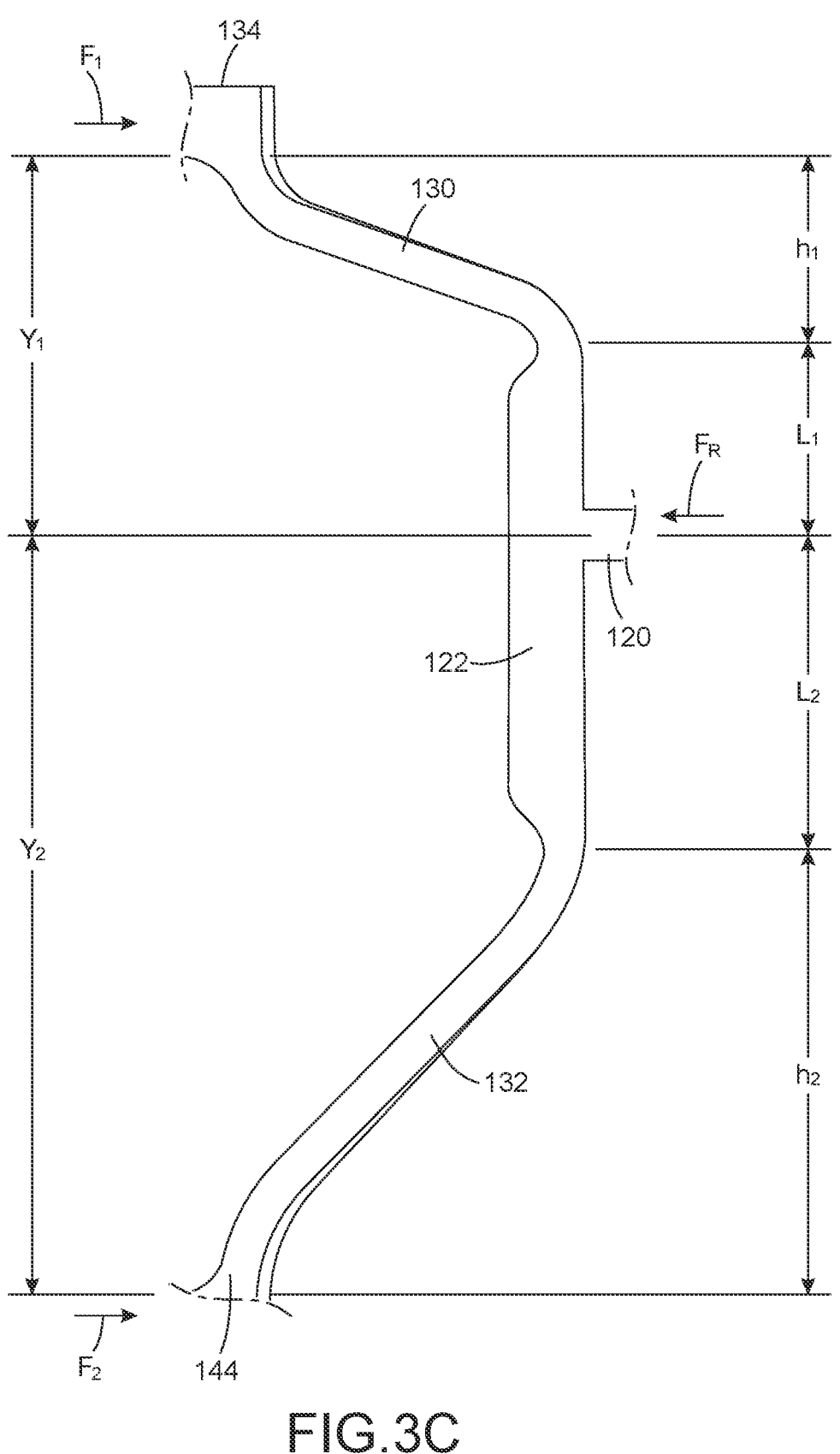
FIG. 3C is a detail view of a section of the H-shaped commissure window of FIG. 3A and surrounding angled struts, when the prosthetic heart valve is at a configuration midway between the fully-expanded and crimped configurations.
Figures 4A, 4B:
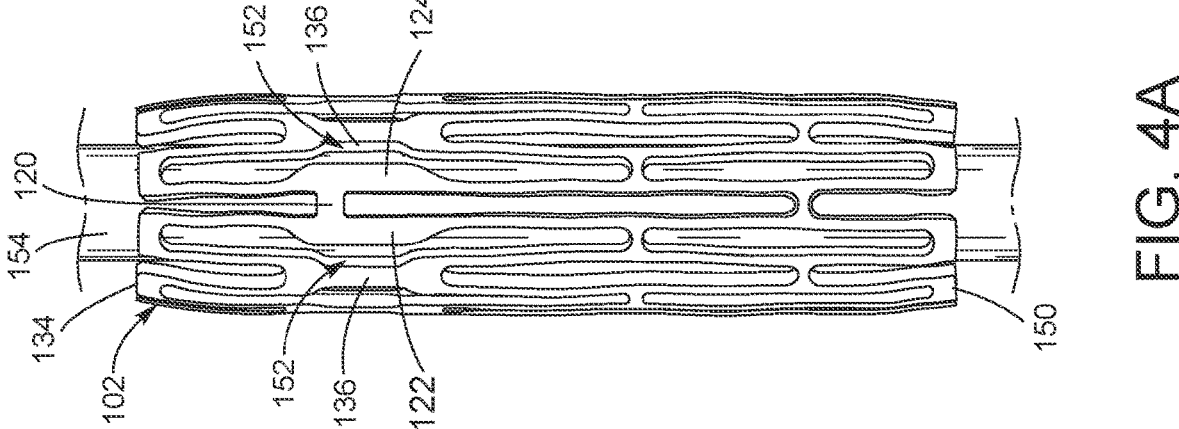
FIGS. 4A-4B are side views of the prosthetic heart valve frame of FIG. 2 in crimped and expanded configurations, respectively.

FIGS. 1-4B illustrate various features of an exemplary prosthetic heart valve 100, according to one or more embodiments of the disclosed subject matter. The prosthetic heart valve 100 can be radially compressible and expandable between a radially compressed configuration for delivery (e.g., a crimped state) into a patient, for example, as illustrated in FIG. 4A, and a radially expanded configuration (e.g., a deployed state), for example, as illustrated in FIGS. 1 and 4B. In particular embodiments, the prosthetic heart valve 100 can be implanted within the native aortic annulus, although it also can be implanted at other locations in the heart, including within the native mitral valve, the native pulmonary valve, or the native tricuspid valve.

The prosthetic heart valve 100 can include an annular stent or frame 102. The frame 102 can have a first axial end 116 and a second axial end 118. In the depicted embodiment, the first axial end 116 can be an outflow end, and the second axial end 118 can be an inflow end. The outflow end 116 can be coupled to a delivery apparatus for delivering and implanting the prosthetic heart valve 100 within the native aortic valve using a transfemoral, retrograde delivery approach. Thus, in the delivery configuration of the prosthetic heart valve, the outflow end 116 can be considered the proximal-most end of the prosthetic valve. In other embodiments, the inflow end 118 can instead be coupled to the delivery apparatus, depending on the particular native valve being replaced and the delivery technique that is used (e.g., trans-septal, transapical, etc.). For example, the inflow end 118 can be coupled to the delivery apparatus (and therefore would be the proximal-most end of the prosthetic heart valve in the delivery configuration) when delivering the prosthetic heart valve to the native mitral valve via a trans-septal delivery approach.

In some embodiments, the frame 102, or components thereof (e.g., struts and/or fasteners), can be made of any of various suitable plastically-expandable materials (e.g., stainless steel, etc.) or self-expanding materials (e.g., nickel titanium alloy (NiTi), such as nitinol), as known in the art. Suitable plastically-expandable materials that can be used to form the frame 102 include, without limitation, stainless steel, biocompatible high-strength alloys (e.g., a cobalt-chromium or a nickel-cobalt-chromium alloys), polymers, or combinations thereof. In particular embodiments, frame 102 is made of a nickel-cobalt-chromium-molybdenum alloy, such as MP35N® alloy (SPS Technologies, Jenkintown, Pennsylvania), which is equivalent to UNS R30035 alloy (covered by ASTM F562-02). MP35N® alloy/UNS R30035 alloy comprises 35% nickel, 35% cobalt, 20% chromium, and 10% molybdenum, by weight.

When constructed of a plastically-expandable material, the frame 102 (and thus the prosthetic valve 100) can be crimped to a radially collapsed configuration on a delivery catheter and then expanded inside a patient by an inflatable balloon or equivalent expansion mechanism. For example, FIGS. 4A-4B illustrates expansion of the frame 102 from a crimped state (e.g., FIG. 4A) to a deployed state (e.g., FIG. 4B) using inflatable balloon 154. When constructed of a self-expandable material, the frame 102 (and thus the prosthetic valve 100) can be crimped to a radially collapsed configuration and restrained in the collapsed configuration by insertion into a sheath or equivalent mechanism of a delivery catheter. Once inside the body, the prosthetic valve can be advanced from the delivery sheath, which allows the prosthetic valve to expand to its functional size.

Figure 16:
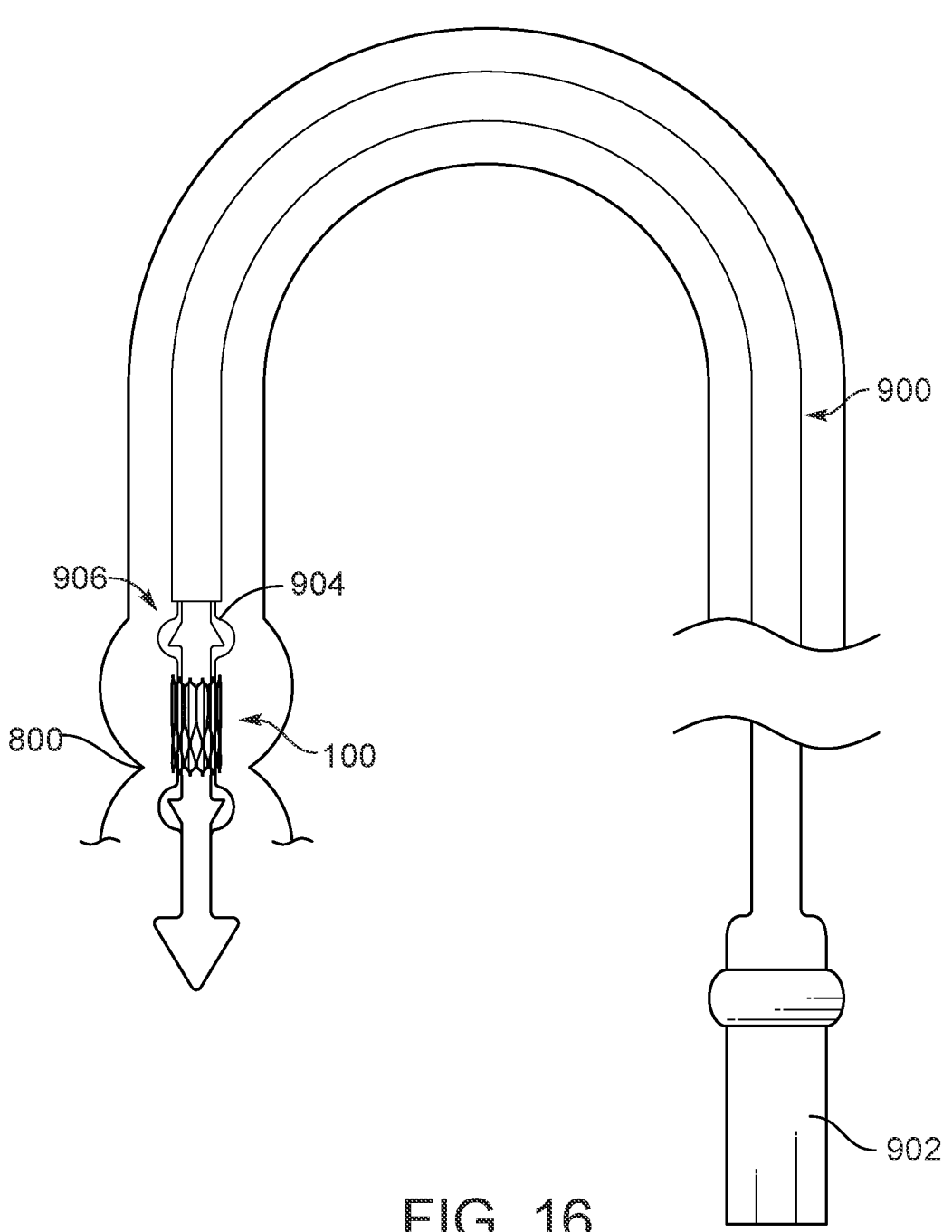
FIG. 16 is a side view of an embodiment of a prosthetic valve being implanted within a native aortic valve of a heart, which is partially shown.

For example, referring to FIG. 16, a delivery apparatus 900 including a handle 902 can be used to deliver and implant the prosthetic valve 100 in the following exemplary manner. The prosthetic valve 100 can be disposed on a distal end portion 906 of the delivery apparatus 900 in a radially compressed state. The prosthetic valve 100 can be crimped on an inflatable balloon 904 (e.g., balloon 154) or another type of expansion member that can be used to radially expand the prosthetic valve 100. The distal end portion 906 of the delivery apparatus 900, including prosthetic valve 100, can be advanced through the vasculature to a selected implantation site (e.g., within a previously implanted host valve and/or within a native valve). In the illustrated embodiment, the distal end portion of the delivery apparatus 900 and the prosthetic valve 100 are inserted into a femoral artery and advanced through the femoral artery and the aorta and positioned within the native aortic valve 800 or a host valve previously implanted within the native aortic valve 800. The prosthetic valve 100 can then be deployed at the implantation site, such as by inflating the balloon 904. Further details of delivery apparatuses that can be used to deliver and implant plastically expandable prosthetic valves, such as the prosthetic valve 100 (or any other prosthetic valves disclosed herein), are disclosed in U.S. Patent Application Publication Nos. 2017/0065415, 2016/0158497, and 2013/0030519, which are incorporated herein by reference.

If the prosthetic valve 100 being implanted is a self-expandable prosthetic valve, the prosthetic valve can be retained in a radially compressed state within a delivery capsule or sheath of the delivery apparatus when inserted into and advanced through the patient's vasculature to the desired implantation site. Once positioned at the desired implantation site, the prosthetic valve can be deployed from the delivery capsule, which allows the prosthetic valve to self-expand to its radially-expanded, functional size within the native valve or a previously implanted host valve. Further details of delivery apparatuses that can be used to deliver and implant self-expandable prosthetic valves (including any of the prosthetic valves disclosed herein when the frames are constructed of a self-expandable material such as Nitinol) are disclosed in U.S. Patent Application Publication Nos. 2014/0343670 and 2010/0049313, which are incorporated herein by reference.

In some embodiments, struts of the frame 102 are pivotable or bendable relative to each other to permit radial expansion and contraction of the frame 102. For example, the frame 102 can be formed (e.g., via laser cutting, electroforming or physical vapor deposition) from a single piece of material (e.g., a metal tube). In other embodiments, the frame 102 can be constructed by forming individual components (e.g., the struts and fasteners of the frame) and then mechanically assembling and connecting the individual components together. For example, instead of the strut structure illustrated in FIGS. 1-4B, the frame can have individual diagonally-extending struts pivotably coupled to one another at one or more pivot joints along the length of each strut, as described in U.S. Patent Application Publication Nos. 2018/0153689, 2018/0344456, and 2019/0060057, all of which are incorporated herein by reference. Further details regarding exemplary constructions of frame 102 and/or prosthetic heart valve 100 are described in U.S. Patent Application Publication Nos. 2012/0123529 and 2019/0365530, U.S. Provisional Application No. 62/869, 948, International Publication No. WO-2020/081893, and International Application No. PCT/US2019/056865, all of which are incorporated herein by reference.

Figure 2:
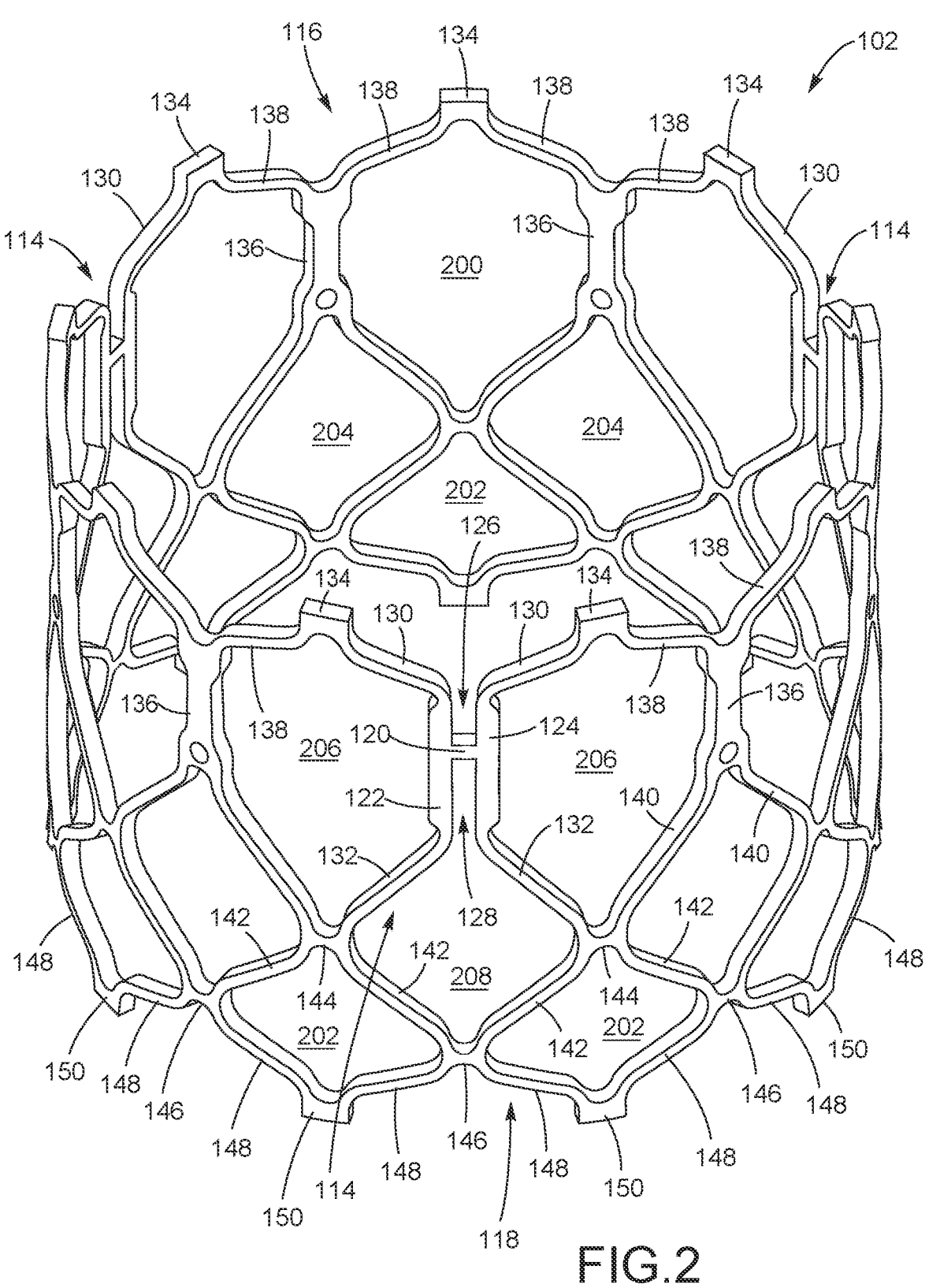
FIG. 2 is a perspective view of an exemplary frame of the prosthetic valve of FIG. 1.

As illustrated in FIGS. 2-3A, frame 102 can include a plurality of struts that are angled with respect to an axial direction (A) of the frame 102 so as to extend along a circumferential direction (C) of the frame 102. The struts can be organized into circumferentially-extending rows, for example, a first row 171 of angled struts 138 and angled struts 130 arranged end-to-end and extending circumferentially at the outflow end 116 of the frame 102; a second row 173 of angled struts 132 and 140 arranged end-to-end and extending circumferentially; a third row 175 of angled struts 142 arranged end-to-end and extending circumferentially; and a fourth row 177 of angled struts 148 arranged end-to-end and extending circumferentially at the inflow end 118 of the frame 102. In some embodiments, a magnitude of the angle with respect to the axial direction for the struts 130, 138 in the first row 171 can be the same as, or substantially similar to (e.g., within 10%), that for the struts 148 in the fourth row 177. In some embodiments, a magnitude of the angle with respect to the axial direction for the struts 132, 140 in the second row 173 and/or the struts 142 in the third row 175 can be different than that for the struts 130, 138 in the first row 171 and/or the struts 148 in the fourth row 177.

Within first row 171, angled struts 130, 138 can connect to (e.g., by joining or integrally formed with) adjacent angled struts 130, 138 via joint or union 134. Similarly, within fourth row 177, angled struts 148 can connect to (e.g., by joining or integrally formed with) adjacent angled struts 148 via joint or union 150. Angled struts 132, 140 of the second row 173 and angled struts 142 of the third row 175 can connect to (e.g., by joining or integrally formed with) each other via joint or union 144. Angled struts 142 of the third row 175 and angled struts 148 of the fourth row 177 can connect to (e.g., by joining or integrally formed with) each other via joint or union 146.

Between the first row 171 and the second row 173, the frame 102 can further include a plurality of support struts 136 and a plurality of commissure windows 114. Each support strut 136 can extend substantially parallel to the axial direction (A) of the frame 102. Each support strut 136 can connect to (e.g., by joining or integrally formed with) an adjacent pair of the angled struts 138 of the first row 171 at its first end (e.g., closest to outflow end 116 of the frame 102) and can connect to (e.g., by joining or integrally formed with) an adjacent pair of the angled struts 140 of the second row 173 at its opposite second end (e.g., closest to inflow end 118 of the frame 102). Similarly, each commissure window 114 can connect to (e.g., by joining or integrally formed with) an adjacent pair of angled struts 130 of the first row 171 at its first end (e.g., closest to outflow end 116 of the frame 102) and can connect to (e.g., by joining or integrally formed with) an adjacent pair of angled struts 132 of the second row 173 at its opposite second end (e.g., closest to inflow end 118 of the frame 102).

The angled struts, support struts, commissure windows, and other frame portions collectively define an open-cell lattice structure, with each of the cells 200-208 being open along a radial direction (R) of the annular frame. At the outflow end 116 of the valve 100, each cell 200 can be defined, at least in part, by a pair of angled struts 138 of the first row 171, a pair of support struts 136, and a pair of angled struts 140 of the second row 173. Also at the outflow end 116 of the valve 100, each cell 206 can be defined, at least in part, by angled strut 130 and angled strut 138 of the first row 171, a support strut 136, a commissure window 114, and angled strut 132 and angled strut 140 of the second row 173. At the inflow end 118 of the valve, each cell 202 can be defined, at least in part, by a pair of angled struts 142 of the third row 175 and a pair of angled struts 148 of the fourth row 177. In between cells 200 at the outflow end and cells 202 at the inflow end along the axial direction, each cell 204 can be defined, at least in part, by a pair of angled struts 140 of the second row 173 and a pair of angled struts 142 of the third row 175. In between cells 206 at the outflow end and cells 202 at the inflow end along the axial direction, each cell 208 can be defined, at least in part, by a pair of angled struts 132 of the second row 173 and a pair of angled struts 142 of the third row 175.

In the illustrated embodiment, each cell 200, 206 at the outflow end 116 has a respective open area that is greater than that of the cells 202 at the inflow end 118. Each of the cells 204, 208 can have a respective open area that is between that of the outflow end cells 200, 206 and the inflow end cells 202. The relatively-larger openings of cells 200, 206 at the outflow end 116 can allow portions of the leaflets of the valvular structure to protrude or bulge into and/or through the openings of the cells when the frame 102 is crimped, for example, to minimize crimping profile of the valve 100. In other embodiments, cells 200-208 can have substantially the same open areas, the cells 202 at the inflow end 118 can have the largest open area instead of cells 200, 206, or the intermediate cells 204, 208 can have the largest open area instead of cells 200, 206.

The frame 102 can be formed with a plurality of circum-ferentially-spaced commissure windows 114 that are adapted to couple the valvular structure 106 to the frame 102. In particular, each commissure 112 of the valvular structure 106 is mounted to a respective one of the com-missure windows 114. The support struts 136 and the commissure windows 114 can be disposed at equal intervals along the circumferential direction of the frame 102. In the illustrated embodiment, the valvular structure 106 comprises three leaflets 110 (e.g., a tricuspid configuration), and the commissure windows 114 are equally spaced at 120° inter-vals (i.e., 0°, 120°, and 240°) along the circumference of the frame 102. A pair of support struts 136 are disposed along the circumference of the frame between each sequential pair of the commissure windows 114 and equally spaced from each other. Thus, either a support strut 136 or a commissure window 114 can be disposed at regular intervals around the circumference of the frame 102, for example, at each 40° interval.

Other spacings and numbers of supports struts 136 and commissure windows 114 are also possible according to one or more contemplated embodiments. For example, a single support strut 136 can be disposed between each sequential pair of commissure windows 114. In such an example, either a support strut 136 or a commissure window 114 can be disposed at 60° intervals around the circumference of the frame 102. In another example, the valvular structure 106 comprises two leaflets 110 (e.g., a bicuspid configuration), and the commissure windows 114 are disposed on opposite sides of the frame (e.g., aligned on a same diameter of the frame). Multiple support struts 136 can be disposed along the circumference of the frame between the pair of com-missure windows 114, and each support strut 136 may be disposed on an opposite side of the frame from another support strut 136 (e.g., both aligned on a same diameter of the frame).

As shown in FIGS. 2A-3B, each commissure window 114 can be formed by a pair of window struts 122, 124 and a crossbar 120. Window struts 122, 124 can extend substan-tially parallel to the axial direction of the frame 102. Each window strut 122, 124 can connect to (e.g., by joining or integrally formed with) an adjacent angled strut 130 at its first end (e.g., closest to the outflow end 116 of the frame 102) and connect to (e.g., by joining or integrally formed with) an adjacent angled strut 132 at its second end (e.g., closets to the inflow end 118 of the frame 102). The crossbar 120 can extend between the window struts 122, 124 along the circumferential direction and connect with the window struts 122, 124, thereby dividing a spacing between the window struts 122, 124 into an upper window or opening 126 and a lower window or opening 128. For example, each commissure window 114 is constructed to have a substan-tially H-shape in respective side view.

The upper opening 126, which is defined by facing surfaces of portions of the window struts 122, 124 at the first end and an upper surface of the crossbar 120, can be open to the outflow end 116 along the axial direction of the valve 100. The lower opening 128, which is defined by facing surfaces of portions of the window struts 122, 124 at the second end and a lower surface of the crossbar 120, can be open to an adjacent cell 208 along the axial direction of the valve 100. Lower opening 128 of the window 114 is closed to the inflow end 118 of the valve 100 by virtue of union 146, which closes cell 208 to the inflow end 118 of the valve 100. However, in other embodiments, union 146 of cell 208 can be omitted, thereby allowing lower opening 128 of com-missure window 114 to be open to the inflow end 118 while upper opening 126 of commissure window 114 is open to the outflow end 118. In still other embodiments, lower opening 128 of commissure window 114 can be open to the inflow end 118 (e.g., via removal of union 146 of cell 208) while upper opening 126 of commissure window 114 can be closed to the outflow end 116 (e.g., by providing another crossbar or union between angled struts 130 at an end of the upper opening 126).

The window struts 122, 124 can be spaced from each other along the circumferential direction by a gap width, $W_1$. The size of the upper and lower openings 126, 128 is thus defined by the spacing between struts 122, 124 and the position of the crossbar 120. Alternatively, the upper opening 126 can have a different gap width than that of the lower opening 128. In some embodiments, the gap width $W_1$ can be defined based on the size of leaflet tabs that are inserted into the openings 126, 128 of the commissure window 114. For example, the gap width $W_1$ can be greater than twice a thickness of a leaflet tab, and/or less than four times the thickness of the leaflet tab. A commissure 112 formed by a pair of leaflet tabs can thus be inserted through the gap width $W_1$ of each opening 126, 128, but is prevented from passing back through the opening upon folding of the leaflet tab in combination with one or more wedge members, as described in further detail below.

The commissure window 114 can have a length, L, along the axial direction of the frame 102 between first ends of the window struts 122, 124 (e.g., ends closest to the outflow end 116) and second ends of the window struts 122, 124 (e.g., ends closest to the inflow end 118). In some embodiments, the crossbar 120 can be offset from a midpoint of the window struts 122, 124 (e.g., L/2) along the axial direction of the frame 102, for example, between the outflow end 116 and the window strut midpoints. For example, a length, $L_1$, of the upper opening 126, as measured from the first ends of the window struts 122 to a middle of the crossbar 120, is less than a length, $L_2$, measured from the second ends of the window struts 122, 124 to the middle of the crossbar 120, such that the upper opening 126 is smaller (e.g., in terms of dimension along the axial direction or open area) than the lower opening 128. For example, a ratio of $L_1$ to $L_2$ (e.g., $L_1/L_2$) can be in a range of 0.25 to 0.35, inclusive.

In some embodiments, each window strut 122, 124 can have a width, $W_2$, along the circumferential direction of the frame 102 that is relatively larger than that of the surrounding angled struts 130, 132. For example, each angled strut 130, 132 can have a width, $W_3$, measured in a direction perpendicular to its direction of extension, and $W_2$ may be greater than $W_3$. In some embodiments, the other angled struts 138, 140, 142, and 148 can each have a width that is the same as or substantially similar (e.g., within 10%) to the width $W_3$ of angled struts 130, 132. Thus, each window strut 122, 124 can be wider than the angled struts of the frame 102.

In some embodiments, the sizing and/or location of components of the commissure window 114 can be tailored to avoid formation of convex or concave contours along the struts 122, 124 during transition between crimped (FIG. 4A) and fully expanded (FIG. 4B) configurations of the valve 100. For example, by increasing widths $W_2$ of the window struts 122, 124, the stiffness of the window struts can be increased such that the struts maintain a substantially linear contour during the transition. Alternatively or additionally, the sizing and/or location of components of the commissure window 114 can be tailored such that the gap widths $W_1$ of the upper opening 126 and/or the lower opening 128 remain substantially constant (e.g., variations of 10% or less) as the valve 100 transitions between crimped (FIG. 4A) and fully expanded (FIG. 4B) configurations. For example, by positioning the crossbar 120 at a particular location along the axial direction, circumferentially-directed forces acting on the first ends of the struts 122, 124 can be balanced with circumferentially-directed forces acting on the second ends of the struts 122, 124. In combination with the increased widths of the window struts 122, 124, the balancing can allow the widths $W_1$ of the upper and lower openings to remain substantially constant during the transition.

For example, both the location of the crossbar 120 along the axial direction of the frame 102 and the widths $W_2$ of the window struts 122, 124 can be selected such that the shape of the commissure window 114 does not deform, or experiences only minimal deformation (e.g., no more than 10% variation), as the frame 102 transitions between fully expanded and crimped states, in order to reduce the risk of damage to and/or detachment of the leaflets. In some embodiments, finite element analysis (FEA) can be used to determine optimal values for the widths for the struts 122, 124 and axial location of crossbar 120, which values may depend on the particular construction of the valve frame 102 (e.g., material composition, number and geometry of open cells, sizes and angles of adjacent struts 130, 132, etc.).

Alternatively, or additionally, the axial location for the crossbar 120 can be based on relative positions along the axial direction of the angled struts 130, 132. FIG. 3C shows a section view for a commissure window 114 and surrounding angled struts 130, 132, when the valve 100 is at a configuration midway between the fully-expanded and crimped states. In FIG. 3C, $h_1$ represents a relative length along the axial direction for angled strut 130 as measured from one end of strut 130 (adjacent to the first end of window strut 122) to an opposite end of strut 130 (at union 134), and $h_2$ represents a relative length along the axial direction for angled strut 132 as measured from one end of strut 132 (adjacent to the second end of the window strut 122) to an opposite end of strut 132 (at union 144). The angled strut 130 is associated with a relative distance $y_1$, measured along the axial direction from a middle of crossbar 120 to the end of strut 130 at union 134. The angled strut 132 is also associated with a relative distance $y_2$, measured along the axial direction from the middle of crossbar 120 to the end of strut 132 at union 144. To avoid (or at least reduce) deformation of the commissure window 114, the location of the crossbar 120 can be selected such that the $(h_1 \times y_2)/(h_2 \times y_1)$ is within a range of 0.8-1.2, inclusive, preferably 0.9-1.1, inclusive. For example, the location of the crossbar 120 can be selected such that $(h_1 \times y_2)/(h_2 \times y_1) \approx 1$. Note that the values recited above are for $h_1$, $h_2$, $y_1$, and $y_2$ measured when the frame 102 is midway (e.g., at a mean diameter, $D_3 = (D_2 - D_1)/2$) between the fully-expanded ($D_2$) and crimped ($D_1$) states.

Using the crossbar location, the width $W_2$ of the window strut 122 can be derived based on forces applied by angled struts 130, 132, for example, such that the maximum force applied along the circumferential direction to the angled strut 130 (e.g., $F_1$) during transition between crimped and expanded states results in minimal deflection of the first end of the window strut 122 and such that the maximum force applied along the circumferential direction to the angle strut 132 (e.g., $F_2$) during the transition between states results in minimal deflection of the second end of the window strut 122. In some embodiments, the other window strut 124 of the commissure window 114 can have dimensions (e.g., width $W_2$ and length along the axial direction) identical to that of window strut 122 for symmetrical application of forces.

In some embodiments, each support strut 136 can also have a width along the circumferential direction of the frame 102 that is relatively larger than the of the surrounding angled struts 138, 140. For example, the angled struts 138, 140 can also have a width, $W_3$, measured in a direction perpendicular to its direction of extension, and a minimum width of the support strut 136 can be greater than $W_3$. In the illustrated embodiment, each support strut 136 can have a width (as measured along the circumferential direction) that varies along the axial direction of the frame 102. For example, opposite ends of the support strut 136 can have a relatively larger width while a mid-portion between the opposite ends can have a relatively smaller width. Thus, each support strut 136 can have a dog-bone shape in respective side view, with a recess 152 being formed between the larger-width ends of the strut 136. When the frame 102 is in the crimped configuration (e.g., as shown in FIG. 4A), the dog-bone shape of the support strut 136 can complement a shape of a facing strut 122, 124 of the adjacent commissure window 114, with a portion of the facing strut 122, 124 fitting into recess 152. The dog-bone shape of the support strut 136 can thus allow the frame 102 to achieve a minimum crimping profile despite the presence of the commissure windows 114. In some embodiments, some of the support struts 136 may have a width that is substantially constant along the axial direction while other of the support struts 136 that are immediately adjacent to one of the commissure windows may have the dog-bone shape.

The prosthetic valve 100 also includes a valvular structure 106 configured for allowing blood flow through the frame 102 in one direction, for example, to regulate the flow of blood through the prosthetic heart valve 100 from the inflow end 118 to the outflow end 116. The valvular structure 106 can include, for example, a leaflet assembly formed by one or more leaflets 110 (three leaflets illustrated in FIG. 1) made of a flexible material. Tabs of adjacent leaflets 110 can be arranged together to form commissures 112 that are coupled (directly or indirectly) to respective commissure windows 114 of the frame 102, thereby securing at least a portion of the valvular structure 106 to the frame 102.

Figure 5:
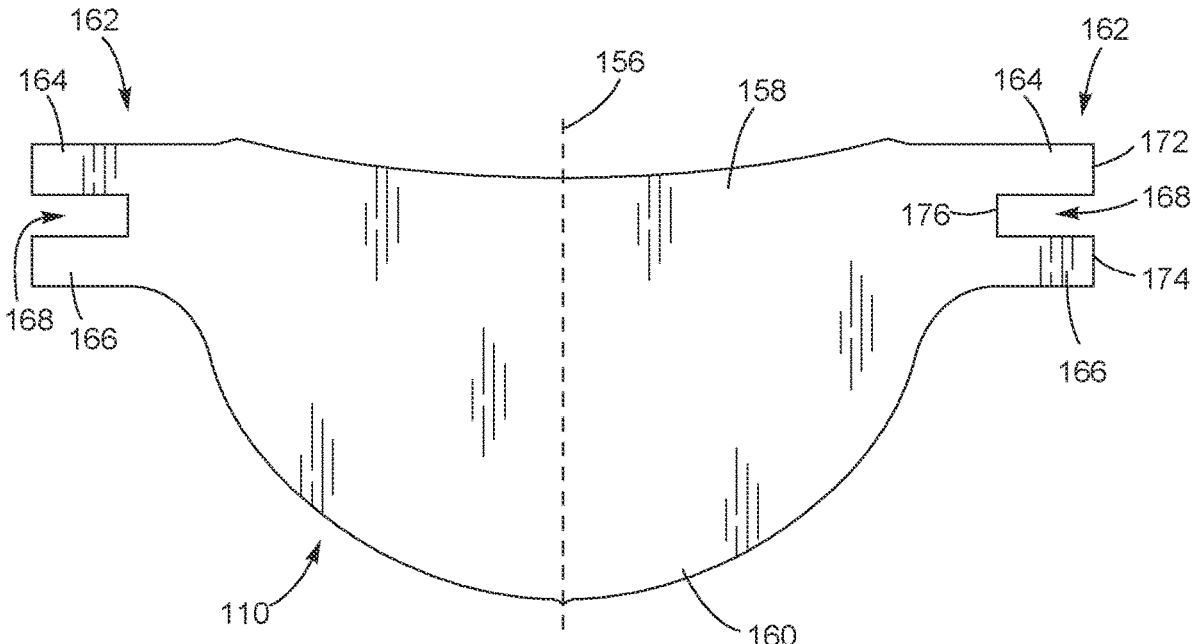
FIG. 5 is a plan view of an individual leaflet used to form a leaflet assembly for a prosthetic heart valve.

As shown in FIG. 5, each leaflet 110 can comprise a main, cusp edge portion 160, two leaflet tabs (also referred to herein as commissure tabs) 162 at opposing ends of the leaflet 110, and an upper edge portion 158. The cusp edge portion 160, leaflet tabs 162, and upper edge portion 158 may be arranged around an outer perimeter of the leaflet 110. The upper edge portion 158 can extend between the two leaflet tabs 162 at an upper edge of the leaflet 110, and the cusp edge portion 160 can extend between the two leaflet tabs 162 at a lower edge of the leaflet 110. As used here, "upper" and "lower" may be relative to a central longitudinal axis of the prosthetic heart valve 100 when the valvular structure is installed and coupled to frame 102, with upper being closer to the outflow end of the valve 100 and lower being closer to the inflow end of the valve 100. The upper edge of the leaflet 110 can be referred to as the "free edge" or the "coaptation edge" of the leaflet.

In some embodiments, the cusp edge portion 160 has a curved, scalloped shape (as shown in FIG. 5). Thus, the cusp edge portion 160 may curve between the two leaflet tabs 162. FIG. 5 further illustrates a centerline 156 for each of the individual leaflets 110, which may also be a centerline of the leaflet assembly. For example, when assembled, the centerlines 156 for each of the leaflets 110 may overlap. Further, as shown in FIG. 5, the leaflet tabs 162 may be arranged at opposing ends of the leaflet 110, across the centerline 156 from one another. In some embodiments, the leaflets and/or components of the leaflet assembly may have symmetry with respect to the centerline 156.

The leaflets 110 of the valvular structure 106 can be made from in whole or part, biological materials, bio-compatible synthetic materials, or other such materials. Suitable biological materials can include, for example, bovine pericardium (or pericardium from other sources). Further details regarding transcatheter prosthetic heart valves, including the manner in which the valvular structure can be coupled to the frame 102 of the prosthetic heart valve 100, can be found, for example, in U.S. Provisional Application No. 62/959, 723, U.S. Pat. Nos. 6,730,118, 7,393,360, 7,510,575, 7,993, 394, and 8,652,202, and U.S. Patent Application Publication No. 2018/0325665, all of which are incorporated herein by reference in their entireties.

The tabs 162 of adjacent leaflets 110 can be arranged together to form commissures 112 that can be coupled to respective commissure windows 114, thereby securing at least a portion of the valvular structure 106 to the frame 102. Each tab 162 of the leaflet 110 can have an upper tab portion 164 and a lower tab portion 166. A gap 168 along a direction parallel to centerline 156 can separate the upper tab portion 164 from the lower tab portion 166. Thus, the upper tab portion 164 extends from an end surface 176 of gap 168 outward (e.g., in a direction away from centerline 156) and terminates at free end 172. Similarly, the lower tab portion 166 extends from end surface 176 of gap 168 outward and terminates at free end 174. In some embodiments, the upper and lower tab portions extend substantially parallel to each other, thereby forming a sideways U-shape or C-shape in side view. A length of the upper tab portion 164 along a direction perpendicular to centerline 156 can be substantially the same as that of the lower tab portion 166. However, the height of the upper tab portion 164 along a direction parallel to centerline 156 may be different than that of the lower tab portion 166. For example, upper tab portion 164 can have a height that corresponds to a size of upper opening 126 (e.g., length $L_1$ minus part of the thickness of crossbar 120 in FIG. 3B) of commissure window 114, while lower tab portion 166 can have a height that corresponds to a size of the lower opening 128 (e.g., length $L_2$ minus part of the thickness of crossbar 120 in FIG. 3B) of commissure window 114.

Figure 6:
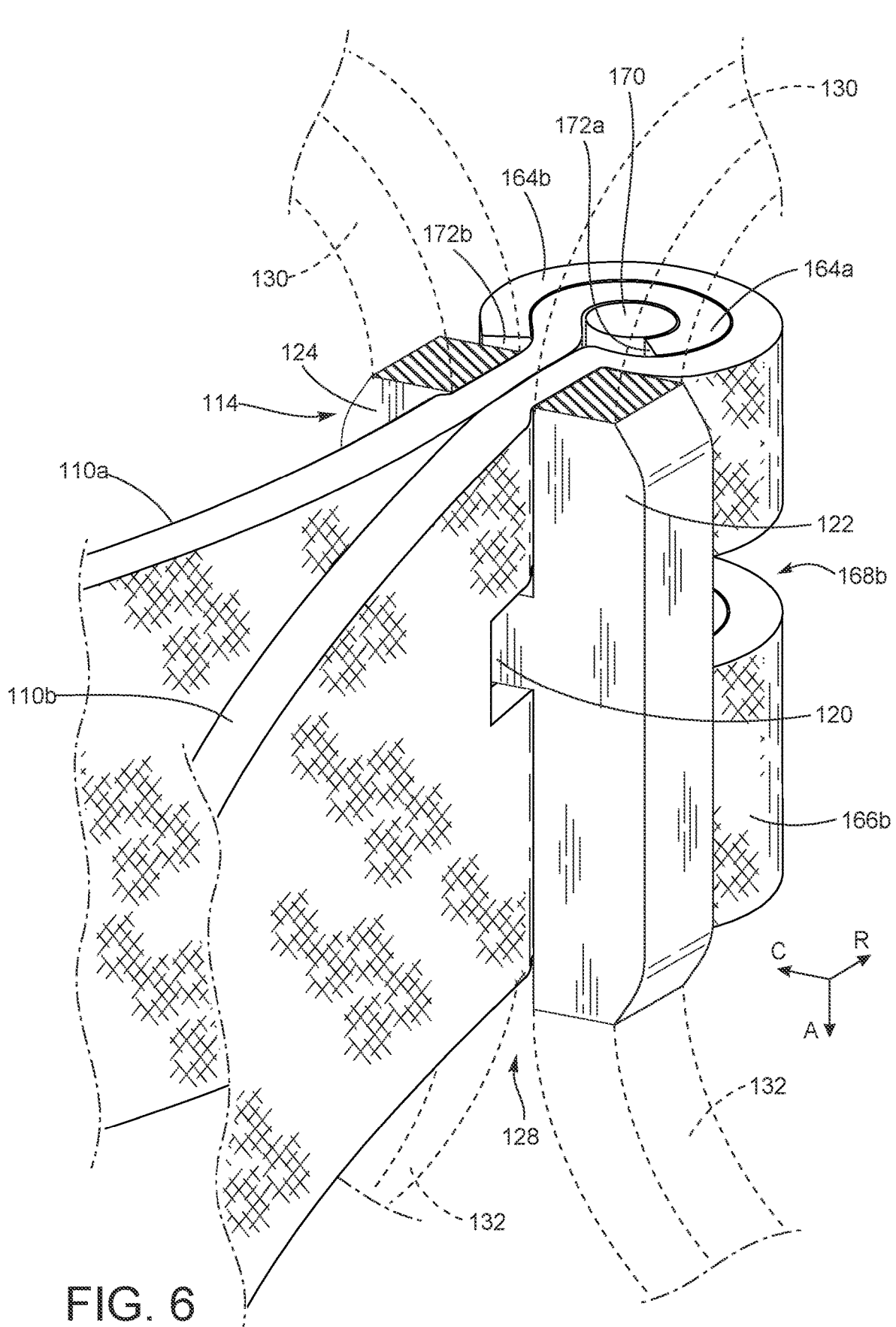
FIG. 6 is a simplified perspective view showing an exemplary assembly of a commissure to the H-shaped commissure window of the prosthetic heart valve frame of FIG. 2.

FIG. 6 shows an exemplary arrangement of leaflets 110a, 110b assembled to an H-shaped commissure window 114, according to one or more embodiments of the disclosed subject matter. Tabs 162 of adjacent leaflets 110a, 110b can be paired together and inserted into commissure window 114 (e.g., by conveying from a radially-inner side to a radially-outer side of the window 114), with upper tab portions 164a, 164b of each leaflet 110a, 110b extending through the upper opening 126 and lower tab portions 166a, 166b of each leaflet extending through the lower opening 128. The gaps separating the upper and lower tabs portions (of which, only gap 168b is visible in FIG. 6) can correspond to a location of the crossbar 120 of the window 114, and the end surface 176 of each gap 168 can be arranged to abut, or at least approach, a radially-inner surface of the crossbar 120 once the commissure is fully installed to the window 114.

The upper tab portions 164a, 164b and the lower tab portions 166a, 166b can be wrapped around a wedge member 170 (or multiple wedge members) and coupled thereto. For example, the leaflet tabs and the wedge member 170 can be coupled to each other using one or more sutures, adhesive, welding, and/or any other means for attaching leaflets to wedge members. In some embodiments, a thickness of the combination of the wrapped tab portions and the wedge member 170 is greater than width $W_1$ of the openings 126, 128 of commissure window 114, thereby preventing the combination from sliding radially inward and back through commissure window 114. Alternatively, or additionally, the wedge member 170 can be a single continuous member that extends along the axial direction between the upper tab portions 164 and the lower tab portions 166. In such configurations, the wedge member 170 may interact with the radially-outer side of the crossbar 120 to prevent the combination from sliding radially inward and back through commissure window 114.

The one or more wedge members 170 can be formed from a relatively thick, multi-filament or monofilament suture, yarn or cable (e.g., a braided, polyester suture, such as an Ethibond suture), a piece of cloth or fabric folded one or more times to increase its thickness, or any other structure. For example, the disclosed wedge members, or sutures coupled thereto, can be formed of a material that does not encourage tissue ingrowth, such as ultra-high molecular weight polyethylene (UHMPE), polyethylene terephthalate (PET), polyurethane (PU), or polytetrafluoroethylene (PTFE). Alternatively, or additionally, any other material that is minimally porous, configured to prevent or minimize neo-vascularization, or does not allow tissue anchoring can be used for the disclosed wedge members. Alternatively, or additionally, the disclosed wedge members can be a coated or laminated polymeric material. In some embodiments, the material for the disclosed wedge members can be a polymer material that is processed in a manner, or otherwise configured, to reduce the likelihood for tissue ingrowth. For example, if exposure of the material to certain levels of heat may induce thrombogenicity, the materials for the disclosed wedge members may be processed in a manner that avoids or reduces such heating steps.

In the illustrated embodiment, commissure windows 114 are formed as part of the lattice structure of the frame 102. In other embodiments, commissure windows 114 may instead be formed in another structure of the frame 102 or as a separate structure attached to the frame 102. For example, in some embodiments, the prosthetic valve includes one or more actuators coupled to the frame to cause transition of the valve between crimped and expanded configurations, and/or one or more locking mechanisms that maintains a shape of the frame after expansion or contraction. In addition to or in place of commissure windows provided in the lattice structure of the frame, at least one of the actuators or locking mechanisms can include an H-shaped commissure window formed therein and can be used to mount a commissure of the valvular assembly thereto. Further details of the actuators, locking mechanisms and delivery apparatuses for actuating the actuators can be found in U.S. Patent Application Publication Nos. 2018/0153689, 2018/0325665, and 2019/0060057, each of which is incorporated herein by reference in its entirety. Any of the actuators and locking mechanisms disclosed in the previously filed applications can be incorporated in any of the prosthetic valves disclosed herein. Further, any of the delivery apparatuses disclosed in the previously filed applications can be used to deliver and implant any of the prosthetic valves discloses herein.

Alternatively, or additionally, the prosthetic valve can include one or more support members that form a part of or are coupled to the annular frame and that include an H-shaped commissure window. For example, the support member can be an axially extending member that is attached to a radially-inner surface of the frame, and the H-shaped commissure window can be formed in the support member (e.g., an axially-extending commissure post coupled to the frame, an actuator, or a locking mechanism). Alternatively, or additionally, the H-shaped commissure window can be formed by a wireform (e.g., bent piece of wire) or clamp coupled to the frame, actuator, locking mechanism, or support member. Further details regarding commissure windows formed from wireforms and commissure windows formed in or on actuators, locking mechanisms, and support members can be found in U.S. Provisional Applications No. 62/959,723 and International Publication No. WO-2020/102487, both of which are incorporated herein by reference in their entireties.

As shown in FIG. 1, the prosthetic heart valve 100 can also include one or more skirts or sealing members. For example, the prosthetic heart valve 100 can include an inner skirt 108 mounted on an inner surface of the frame 102 and/or an outer skirt 104 mounted on an outer surface of the frame 102. The inner skirt 108 can be a circumferential inner skirt that spans an entire circumference of the inner surface of the frame 102. The inner skirt 108 can function as a sealing member to prevent or decrease perivalvular leakage (e.g., when the valve is placed at the implantation site) and as an attachment surface to anchor a portion of the leaflets 110 to the frame 102. For example, the cusp edge portions 160 of the leaflets 110 (see FIG. 5) can be sutured to the inner skirt 108, which in turn can be sutured to selected struts 142 of the frame 102. The outer skirt 104 can function as a sealing member by sealing against the tissue of the native valve annulus and helping to reduce paravalvular leakage past the prosthetic valve 100. The inner and outer skirts 108, 104 can be formed from any of various suitable biocompatible materials, including any of various synthetic materials (e.g., polyethylene terephthalate (PET)) or natural tissue (e.g., pericardial tissue). The inner and outer skirts 108, 104 can be mounted to the frame 102 using sutures, adhesive, welding, and/or other means for attaching the skirts to the frame. Further details regarding the inner and outer skirts, techniques for assembling the leaflets to the inner skirt, and techniques for assembling the skirts on the frame are disclosed in U.S. Patent Application Publication Nos. 2012/0123529, 2019/0192296, and 2019/0365530, and International Patent Application Nos. PCT/US2020/014701 and PCT/US2020/024559, each of which is incorporated herein by reference.

Once each commissure 112 of the valvular structure 106 has been secured to a respective one of the commissure windows 114, the lower edges of the leaflets 110 between commissures 112 can be sutured to the inner skirt 108. For example, the sutures can be in-and-out sutures extending through each leaflet, inner skirt, and optionally a reinforcing strip (not shown). Each leaflet and respective reinforcing strip can be sewn separately to the inner skirt. In this manner, the lower edges of the leaflets 110 can be secured to the frame 102 via the inner skirt 108. In some embodiments, the lower edges of the leaflets 110 can be secured to the skirt with blanket sutures that extend through each reinforcing strip, leaflet, and the inner skirt while looping around edges of the reinforcing strips and leaflets.

In some embodiments, adjacent leaflet tabs of a commissure can be coupled together prior to insertion through the commissure window. A first leaflet tab of the commissure can be folded and attached to a second leaflet tab, which can remain unfolded. Once the upper and lower tab portions of the first and second leaflet tabs are passed through the upper and lower openings, respectively, to the radially-outer side of the commissure window, one or more wedge members can be inserted between folded portions of the first leaflet tab. Prior to or after insertion of the wedge member(s), the second leaflet tab can be wrapped around the folded first leaflet tab. The wedge member(s) can increase a width of the combination of first and second folded leaflet tabs such that the leaflet tabs cannot pass back through the window.

Figure 7A:
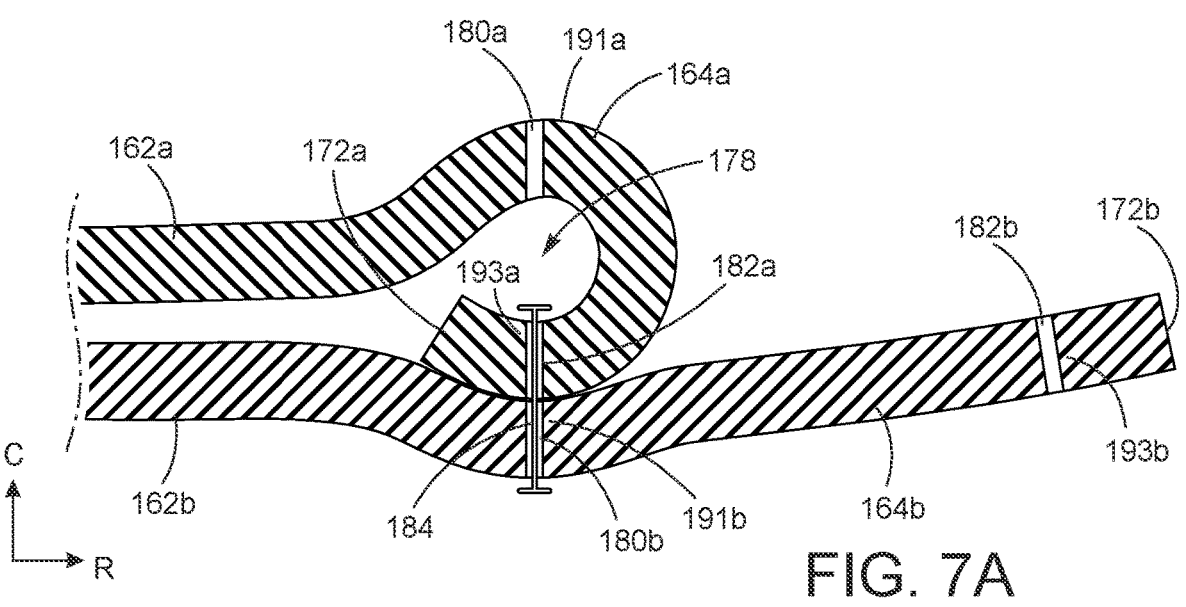
FIG. 7A-7B are simplified top-down and perspective views, respectively, that illustrate coupling of a pair of leaflet tabs of a commissure prior to insertion through an H-shaped commissure window, according to a first exemplary assembly method.

For example, FIGS. 7A-10 illustrate a first exemplary method of installing a commissure 112 to an H-shaped commissure window 114. Referring to FIGS. 7A-7B, a first leaflet tab 162a and a second leaflet tab 162b can be disposed adjacent to each other. The first leaflet tab 162a can have an upper tab portion 164a with free end 172a, a lower tab portion 166a with free end 174a, and a gap 168a with end surface 176a separating the upper and lower tab portions. Similarly, the second leaflet tab 162b can have an upper tab portion 164b with free end 172b, a lower tab portion 166b with free end 174b, and a gap 168b with end surface 176b separating the upper and lower tab portions. Each upper tab portion 162a,b can have a first part 193a,b that is adjacent to a free end 172a,b of the upper tab portion and a second part 191a,b that is between the first part 193a,b and the centerline of the leaflet (or the respective end surface 176a,b of the gap 168a,b along a direction perpendicular to the centerline). Similarly, each lower tab portion 164a,b can have a first part that is adjacent to a free end 174a,b of the lower tab portion and a second part that is between the first part and the centerline of the leaflet (or the respective end surface 176a,b of the gap 168a,b along a direction perpendicular to the centerline).

In some embodiments, each of the upper tab portions 164a,b and the lower tab portions 166a,b can optionally be provided with one or more holes, through which one or more sutures can be passed to couple the tab portions and/or a wedge member together. For example, the first parts 193a of the upper and lower tab portions 164a, 166a of the first leaflet tab 162a can have through-holes 182a, while the second parts 191a of the upper and lower tab portions 164a, 166a of the first leaflet tab 162a can have through-holes 180a. Similarly, the first parts 193b of the upper and lower tab portions 164b, 166b of the second leaflet tab 162b can have through-holes 182b, while the second parts of the upper and lower tab portions 164b, 166b of the second leaflet tab 162b can have through-holes 180b. One or more sutures 184 can be passed through the holes 182a in the first leaflet tab 162a and the holes 180b in the second leaflet tab 162b to couple the leaflet tabs 162a,b together. In other embodiments, only some or none of the first and second parts of the tab portions are provided with holes 180, 182. In such embodiments, a suture can pierce through the first or second parts of the leaflet tab portions, or a means for attachment other than a suture can be used to couple the leaflet tab portions together, for example, by welding or adhesive.

Figure 7B:
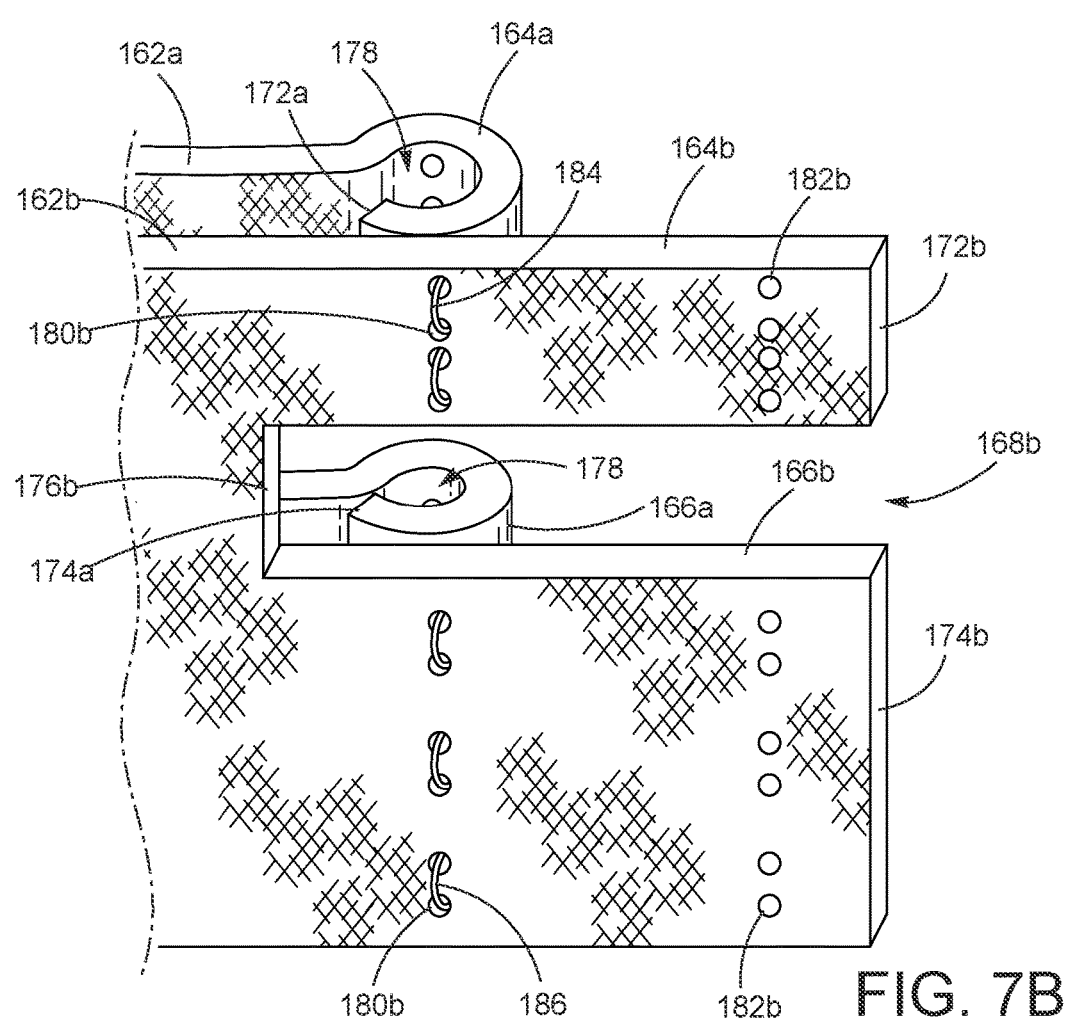

As illustrated in FIGS. 7A-7B, the first leaflet tab 162a can be folded onto itself, for example, by passing the free ends 172a, 174a of the upper and lower tab portions 164a, 166a between the first leaflet tab 162a and the second leaflet tab 162b. Thus, the first part 193a of the upper tab portion 164a of the first leaflet tab 162a contacts, or at least faces, the second part 191b of the upper tab portion 164b of the second leaflet tab 162b, and the first part of the lower tab portion 166a of the first leaflet tab 162a contacts, or at least faces, the second part of the lower tab portion 166b of the second leaflet tab 162b. The folded portions of the first leaflet tab 162a also creates a gap or recess 178 between the facing surfaces of the first part 193a and second part 193a of the upper tab portion 164a and between the facing surfaces of the first and second parts of the lower tab portion 166a.

In some embodiments, one or more sutures 184 can be used to couple the leaflet tabs 162a, 162b together after the folding of the first leaflet tab 162a. Alternatively, the one or more sutures 184 can be used to couple the leaflet tabs 162a, 162b together before the folding of the first leaflet tab 162a. For example, the first leaflet tab 162a can be disposed in a substantially flat configuration on the second leaflet tab 162b and extending in an opposite direction from the second leaflet tab 162b, such that the centerlines of the leaflets are on opposite sides of overlapping portions of the first and second leaflet tabs 162a, 162b. Thus, the first parts 193a of the upper and lower tab portions 164a, 166a of the first leaflet tab 162a can be aligned with the second parts 191b of the upper and lower tab portions 164b, 166b of the second leaflet tab 162b, and the first parts 193b of the upper and lower tab portions 164b, 166b of the second leaflet tab 162b can be aligned with the second parts 191a of the upper and lower tab portions 164a, 166a of the first leaflet tab 162a. In this overlapping configuration, the one or more first sutures 184 can be passed through the first parts 193a of the upper and lower tab portions 164a, 166a of the first leaflet tab 162a (e.g., via through-holes 182a) and through the second parts 191b of the upper and lower tab portions 164b, 166b of the second leaflet tab 162b (e.g., via through-holes 180b) to couple together the leaflet tabs 162a, 162b. After the leaflet tabs are coupled together, the upper and lower tab portions 164a, 166a can then be folded, as described above. In some embodiments, a single suture 184 can be used to couple both the upper and lower tab portions of the first and second leaflet tabs 162a, 162b, so long as the portion of the suture 184 extending between the upper tab portions 164a, 164b and the lower tab portions 166a, 166b does not otherwise interfere with crossbar 120 as the leaflet tabs 162a, 162b are inserted into the commissure window 114.

Figure 8:
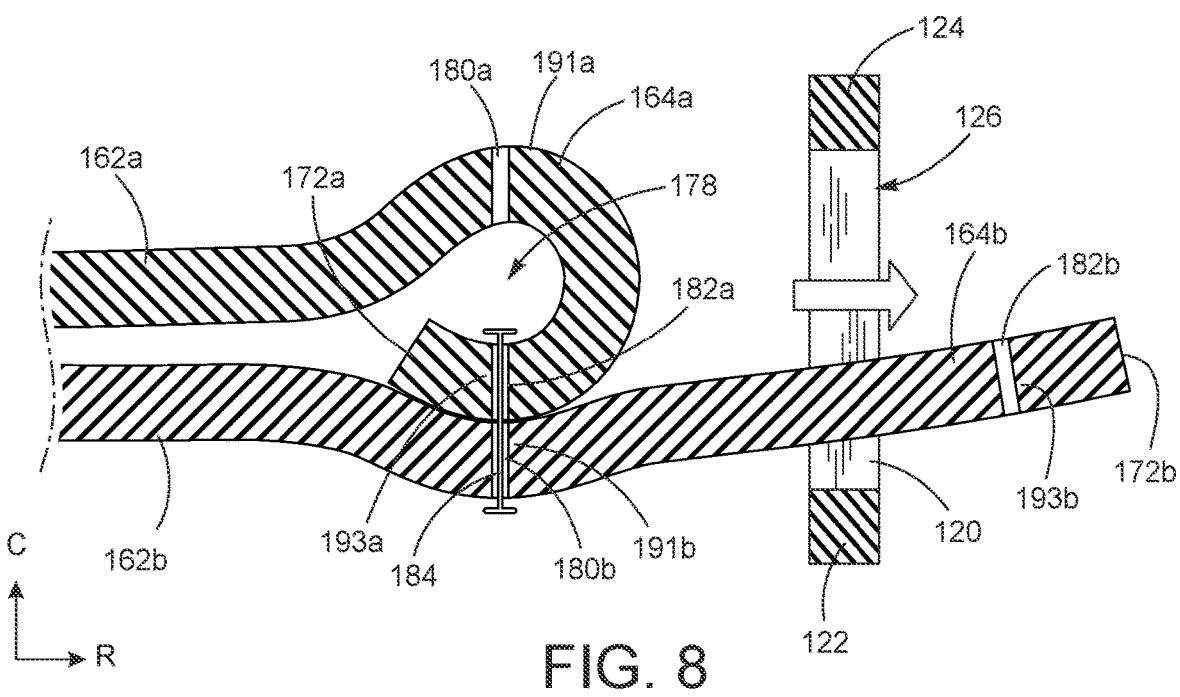
FIGS. 8-10 are simplified top-down views that illustrate insertion of the leaflet tabs of FIGS. 7A-7B through the H-shaped commissure window, insertion of a wedge member, and further attachment of the leaflet tabs, respectively, according to the first exemplary assembly method.

With the upper and lower tab portions 164a, 166a of the first leaflet tab 162a folded, the coupled-together first and second leaflet tabs 162a, 162b can then be conveyed from a radially-inner side through respective openings 126, 128 to a radially-outer side of the commissure window 114. For example, as shown in FIG. 8, the free end 172b of the upper tab portion 166b of the second leaflet tab 162b can be inserted into the upper opening 126 of the commissure window, followed by the remainder of the upper tab portion 166b of the second leaflet tab 162b and the folded portions of the upper tab portion 164a of the first leaflet tab 162a. Similarly, the free end 174b of the lower tab portion 166b of the second leaflet tab 162b can be inserted into the lower opening 128 of the commissure window, followed by the remainder of the lower tab portion 166b of the second leaflet tab 162b and the folded portions of the lower tab portion 166a of the first leaflet tab 162a. In some embodiments, the insertion of the upper tab portions 164a, 164b into the upper opening 126 and the insertion of the lower tab portions 166a, 166b into the lower opening 128 can occur simultaneously or substantially at the same time. In other embodiments, the lower tab portions 166a, 166b can be fully inserted through the lower opening 128 prior to insertion of the upper tab portions 164a, 164b into the upper opening 126, or vice versa.

Figure 9:
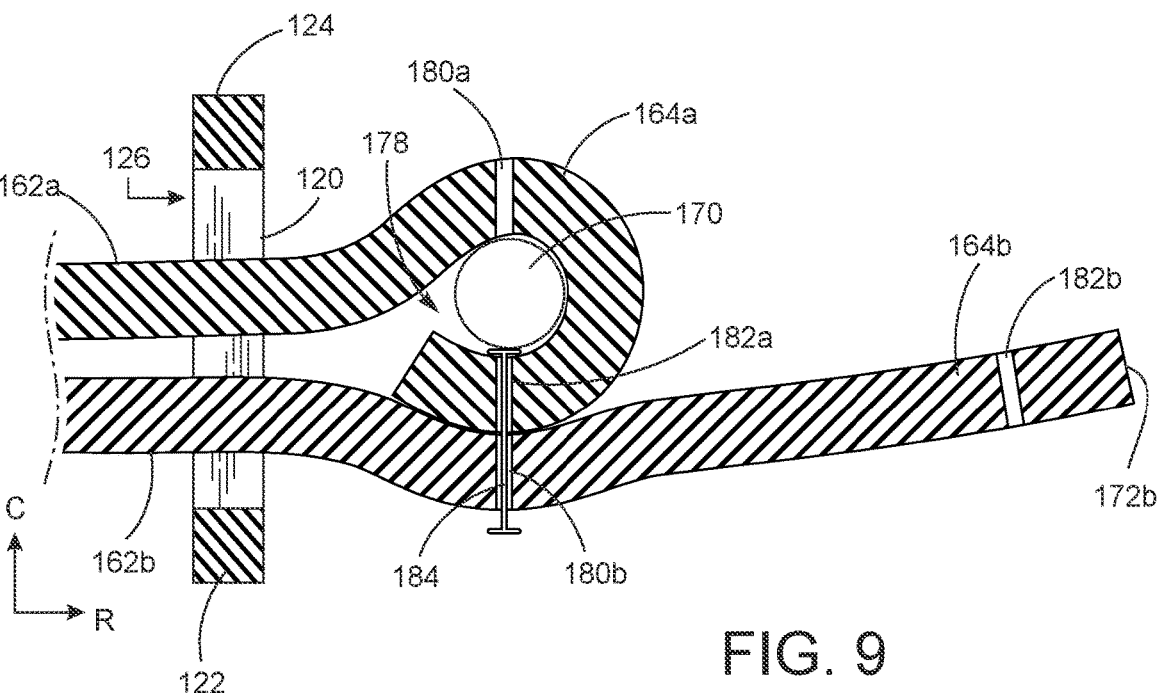

Once the upper and lower tab portions of the first and second leaflet tabs 162a, 162b have been inserted through the respective openings 126, 128 of the commissure window, one or more wedge members can be added to the assembly at the radially-outer side of the commissure window. For example, a wedge member 170 can be inserted into the recess 178 formed by the upper and lower tab portions 164a, 166a of the first leaflet tab 162a, as illustrated in FIG. 9. The wedge member 170 can be conveyed parallel to the axial direction of the frame (e.g., from the outflow end 116 to the inflow end 118 or vice versa) in between the facing surfaces of the first and second parts 191a, 193a of the upper and lower tab portions 164a, 166a of the first leaflet tab 162a. The wedge member 170 can extend between the upper and lower tab portions 164a, 166a and thus prevent, or at least restrain, the leaflet tabs 162a, 162b from passing back through the commissure window 114 (e.g., from the radially-outer side of the window back to the radially-inner side of the window) due to interaction between an intermediate portion of the wedge member 170 (e.g., between the upper tab portion 164a and the lower tab portion 164b along the axial direction of the frame) and the crossbar 120 of the window. The wedge member 170 may also cause a width (along the circumferential direction) of the combination of the first and second leaflet tabs 162a, 162b at the radially-outer side of the window 114 to be greater than that of the upper opening 126 and/or lower opening 128. Thus, the increased width can also prevent, or at least restrain, leaflet tabs 162a, 162b from passing back through the commissure window 114.

Alternatively, multiple wedge members can be provided, for example, a first wedge member for the upper tab portion 164a of the first leaflet tab 162a and a separate second wedge member for the lower tab portion 166a of the first leaflet tab. In such configurations, a gap 168a between the upper tab portion 164a and lower tab portion 166a would remain after insertion of the first and second wedge members. However, each wedge member causes a width (along the circumferential direction) of the combination of the first and second leaflet tabs 162a, 162b at the radially-outer side of the window 114 to be greater than that of the upper opening 126 and/or lower opening 128, thereby preventing, or at least restraining, the leaflet tabs 162a, 162b from passing back through the commissure window 114. In such embodiments, the multiple wedge members can be coupled together (e.g., via stitching using one or more sutures) and/or the upper and lower tab portions on the radially-outer side of the commissure window 114 can be coupled together (e.g., via stitching using one or more sutures), for example, to prevent sliding along the axial direction of the respective tab portions.

Figure 10:
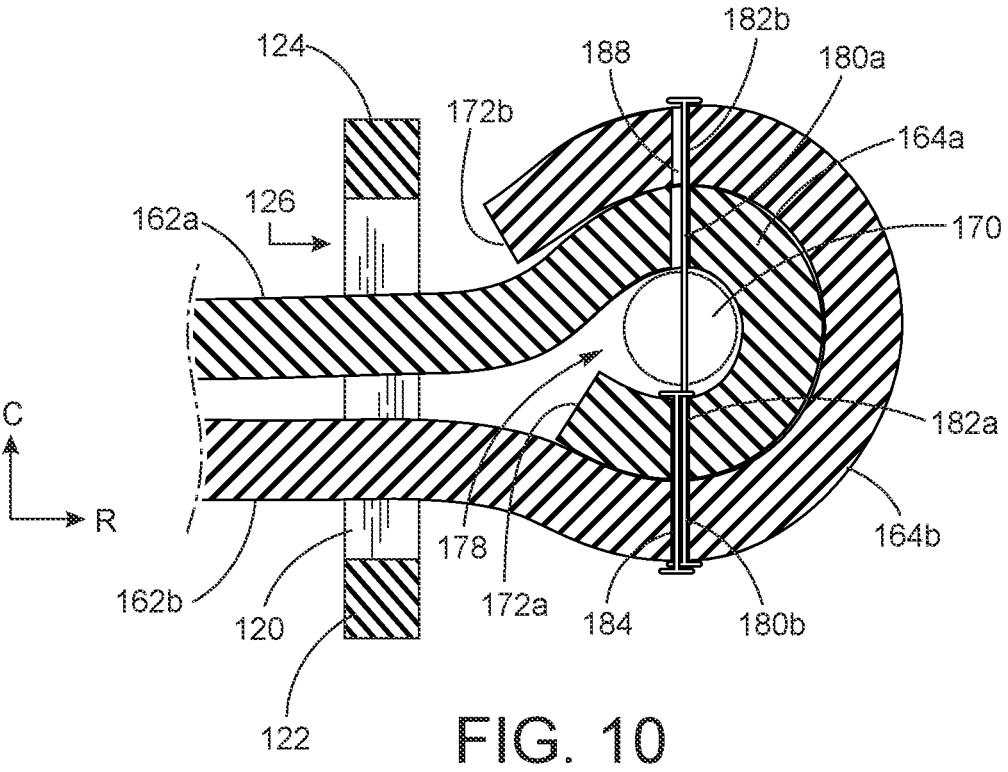

Once the one or more wedge members have been positioned with respect to the first leaflet tab 162a, the upper tab portion 164b of the second leaflet tab 162b can be wrapped around the upper tab portion 164a of the first leaflet tab 162a, as shown in FIG. 10. Before, during, or after the wrapping of the upper tab portion 164b, the lower tab portion 166b of the second leaflet 162b can also be wrapped around the lower tab portion 166a of the first leaflet tab 162a. Alternatively, in some embodiments, the upper tab portion 164b and/or the lower tab portion 166b of the second leaflet tab 162b can be wrapped around the respective tab portions of the first leaflet tab 162a prior to positioning of the wedge members. In either case, after positioning of the one or more wedge members, the tab portions of each leaflet tab 162a, 162b can be arranged such that free ends 172a, 172b of the upper tab portions 164a, 164b and free ends 174a, 174b of the lower tab portions 166a, 166b are disposed between the wedge member 170 and a radially-outer side of the commissure window 114 along a radial direction of the frame 102.

One or more sutures can be used to couple together the wedge members and the folded leaflet tabs 162a, 162b. For example, one or more second sutures 188 can be passed through the first part 193b of the upper tab portion 164b of the second leaflet tab 162b (e.g., via through-holes 182b), the second part 191a of the upper tab portion 164a of the first leaflet tab 162a (e.g., via through-holes 180a), the wedge member 170, the first part 193a of the upper tab portion 164a of the first leaflet tab 162a (e.g., via through-holes 182a), and the second part 191a of the upper tab portion 164b of the second leaflet tab 162b (e.g., via through-holes 180b), in order or vice versa. The one or more second sutures 188 can be passed through the first and second parts of the lower tab portions 166a, 166b of the first and second leaflet tabs 162a, 162b and the wedge member 170 in a similar manner.

If the valvular structure includes other commissures to be attached to commissure windows of the frame, the method of FIGS. 7A-10 can be repeated for the other commissures. In some embodiments, the valvular structure can have a tricuspid configuration with three leaflets, and the three commissures of the valvular structure are coupled to respective commissure windows of the frame by performing the method of FIGS. 7A-10 three separate times. In other embodiments, the valvular structure can have a bicuspid configuration with two leaflets, and the two commissures of the valvular structure are coupled to respective commissure windows of the frame by performing the method of FIGS. 7A-10 two separate times. In any of the embodiments with multiple commissures and commissure windows, performance of some or all of the method for the respective commissures can occur in parallel. For example, the leaflet tabs for each commissure can be folded and coupled together at the same time, after which the coupled leaflet tabs can be inserted into their respective windows. Other variations for parallel assembly of multiple commissures to multiple commissure windows are also possible according to one or more contemplated embodiments.

The method of assembly described with respect to FIGS. 7A-10 provides a simple and cost-effective methodology for installing commissure assemblies to respective windows of the valve frame. For example, the configuration of FIGS. 7A-7B can allow the leaflet tabs 162a, 162b to be quickly and easily coupled together in a flat configuration, followed by a simple sliding/insertion of the upper and lower tab portions into the respective upper and lower openings of the commissure window. Moreover, the assembly of the leaflet tabs and subsequent mounting to the window using one or more wedge members involves a relatively small number of distinct components and assembly stages.

In some embodiments, adjacent leaflet tabs of a commissure can be inserted through the commissure window prior to any folding of the leaflet tabs and/or the coupling of leaflet tabs to each other. The upper and lower tab portions of the first and second leaflet tabs can be passed (simultaneously or sequentially) through the upper and lower openings, respectively, to the radially-outer side of the commissure window. The first leaflet tab can then be folded around one or more wedge members and coupled thereto. Prior to or after the coupling of the first leaflet tab and the wedge member(s), the second leaflet tab can be wrapped around the folded first leaflet tab. The wedge member(s) can increase a width of the combination of first and second folded leaflet tabs such that the leaflet tabs cannot pass back through the window.

Figure 11:
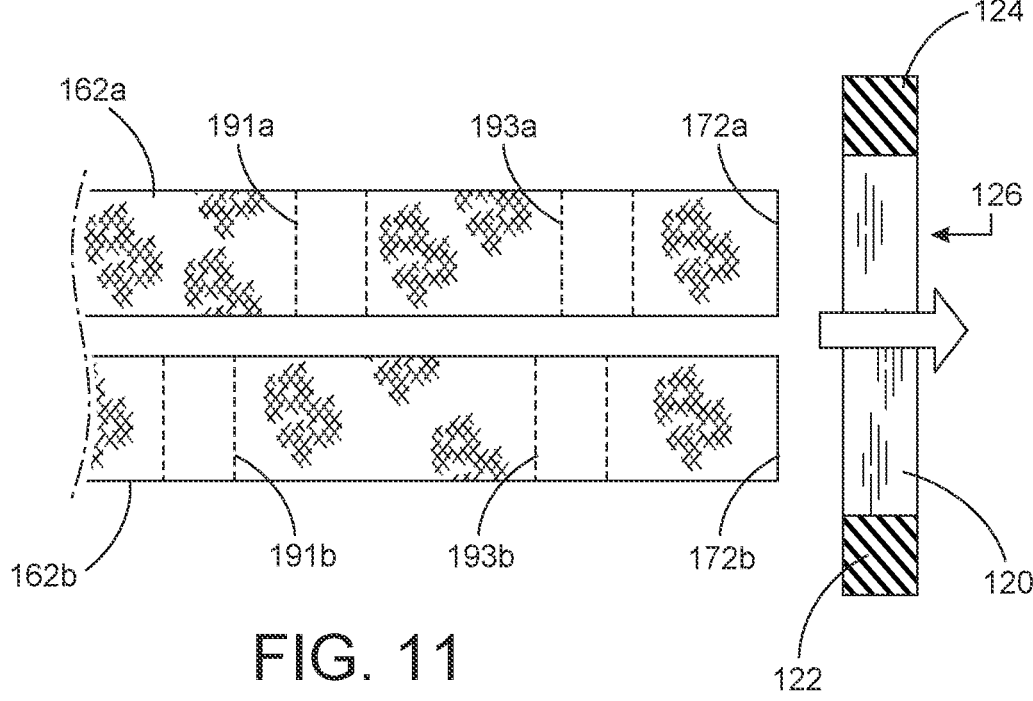
FIGS. 11-13 are simplified top-down views that illustrate insertion of the leaflet tabs through an H-shaped commissure window, insertion of a wedge member, and further attachment of the leaflet tabs, respectively, according to a second exemplary assembly method.
Figures 12, 13:
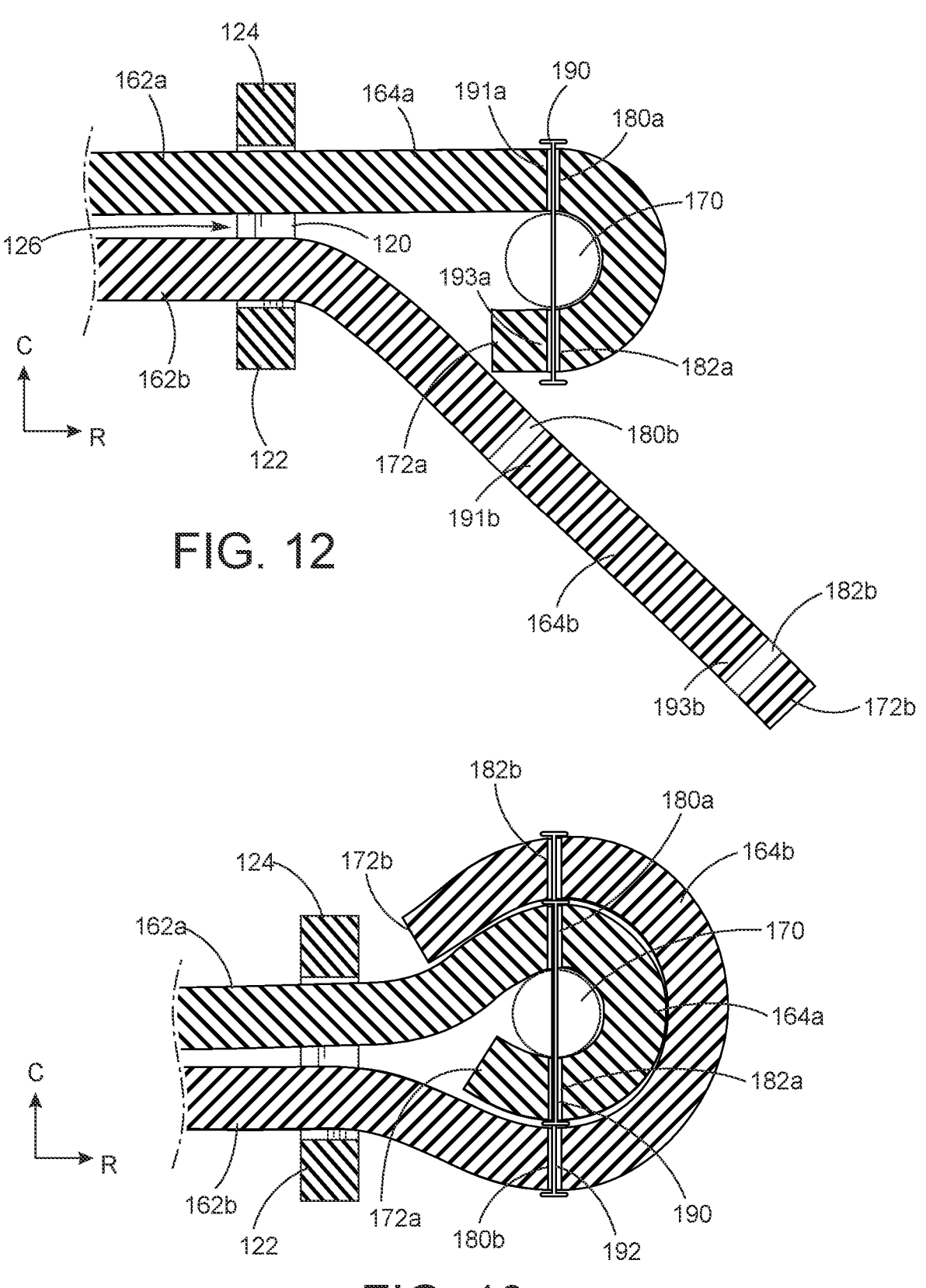

For example, FIGS. 11-13 illustrate a second exemplary method of installing a commissure 112 to an H-shaped commissure window 114. While FIGS. 11-13 illustrate only the upper tab portions 164a, 164b of the first and second leaflet tabs 162a, 162b, it should be noted that the installation of the lower tab portions 166a, 166b of the first and second leaflet tabs 162a, 162b would be handled in a similar manner simultaneously with, or substantially at a same time as, the illustrated installation of the upper tab portions 164a, 164b.

In FIG. 11, a first leaflet tab 162a and a second leaflet tab 162b can be disposed adjacent to each other. As described in detail above, each leaflet tab 162a, 162b can have respective upper tab portions 164a, 164b and lower tab portions 166a, 166b separated by a gap 168a, 168b. Each upper tab portion 162a,b can have a first part 193a,b that is adjacent to a free end 172a,b of the upper tab portion and a second part 191a,b that is between the first part 193a,b and the centerline of the leaflet, and each lower tab portion can have a first part that is adjacent to a free end of the lower tab portion and a second part that is between the first part and the centerline of the leaflet. In some embodiments, the respective first and second parts of the upper tab portions 164a,b and the lower tab portions 166a,b can optionally be provided with one or more holes (e.g., through-holes 180a,b and 182a,b), through which one or more sutures can be passed to couple the tab portions and/or a wedge member together.

The first leaflet tab 162a can be conveyed from a radially-inner side through respective openings 126, 128 to a radially-outer side of the commissure window 114. Before, after, or during the conveying of the first leaflet tab 162a into commissure window 114, the second leaflet tab 162b can be conveyed from the radially-inner side through respective openings 126, 128 to the radially-outer side of the commissure window 114. For example, as shown in FIG. 12, the free end 172a of the upper tab portion 164a of the first leaflet tab 162a can be inserted into the upper opening 126 of the commissure window, and the free end 172b of the upper tab portion 164b of the second leaflet tab 162b can be inserted into the upper opening of the commissure window. Similarly, the free end 174a of the lower tab portion 166a of the first leaflet tab 162a can be inserted into the lower opening 128 of the commissure window, and the free end 174b of the lower tab portion 166b of the second leaflet tab 162b can be inserted into the lower opening of the commissure window. In some embodiments, the insertion of the upper tab portions 164a, 164b into the upper opening 126 and the insertion of the lower tab portions 166a, 166b into the lower opening 128 can occur simultaneously or substantially at the same time. In other embodiments, the lower tab portions 166a, 166b can be fully inserted through the lower opening 128 prior to insertion of the upper tab portions 164a, 164b into the upper opening 126, or vice versa.

After insertion through respective openings 126, 128 of the commissure window 114, the first leaflet tab 162a can be wrapped around one or more wedge members at the radially-outer side of the commissure window. For example, the upper and lower tab portions 164a, 166a of the first leaflet tab 162a can be wrapped around (e.g., folded around) a single wedge member 170, as illustrated in FIG. 12. The wedge member 170 can extend between the upper and lower tab portions 164a, 166a and thus prevent, or at least restrain, the leaflet tabs 162a, 162b from passing back through the commissure window 114 (e.g., from the radially-outer side of the window back to the radially-inner side of the window) due to interaction between an intermediate portion of the wedge member 170 (e.g., between the upper tab portion 164a and the lower tab portion 164b along the axial direction of the frame) and the crossbar 120 of the window. The wedge member 170 may also cause a width (along the circumferential direction) of the combination of the first and second leaflet tabs 162a, 162b at the radially-outer side of the window 114 to be greater than that of the upper opening 126 and/or lower opening 128. Thus, the increased width can also prevent, or at least restrain, leaflet tabs 162a, 162b from passing back through the commissure window 114.

Alternatively, multiple wedge members can be provided, for example, a first wedge member for the upper tab portion 164a of the first leaflet tab 162a and a separate second wedge member for the lower tab portion 166a of the first leaflet tab. In such configurations, a gap 168a between the upper tab portion 164a and lower tab portion 166a would remain after insertion of the first and second wedge members. However, each wedge member causes a width (along the circumferential direction) of the combination of the first and second leaflet tabs 162a, 162b at the radially-outer side of the window 114 to be greater than that of the upper opening 126 and/or lower opening 128, thereby preventing, or at least restraining, the leaflet tabs 162a, 162b from passing back through the commissure window 114. In such embodiments, the multiple wedge members can be coupled together (e.g., via stitching using one or more sutures) and/or the upper and lower tab portions on the radially-outer side of the commissure window 114 can be coupled together (e.g., via stitching using one or more sutures), for example, to prevent sliding along the axial direction of the respective tab portions.

One or more sutures can be used to couple together the wedge members and the wrapped upper and lower tab portions 164a, 166a of the first leaflet tab 162a. For example, as illustrated in FIG. 12, one or more first sutures 190 can be passed through the first part 193a of the upper tab portion 164a of the first leaflet tab 162a (e.g., via through-hole 182a), the wedge member 170, and the second part 191a of the upper tab portion 164a of the first leaflet tab 162a (e.g., via through-hole 180a), in order or vice versa. The one or more first sutures 190 can be passed through the first and second parts of the lower tab portion 166a of the first leaflet tab 162a in a similar manner.

Once the one or more wedge members have been positioned with respect to the first leaflet tab 162a, the upper tab portion 164b of the second leaflet tab 162b can be wrapped around the upper tab portion 164a of the first leaflet tab 162a, as shown in FIG. 13. Before, during, or after the wrapping of the upper tab portion 164b, the lower tab portion 166b of the second leaflet 162b can also be wrapped around the lower tab portion 166a of the first leaflet tab 162a. Alternatively, in some embodiments, the upper tab portion 164b and/or the lower tab portion 166b of the second leaflet tab 162b can be wrapped around the respective tab portions of the first leaflet tab 162a prior to positioning of the wedge members. In either case, after positioning of the one or more wedge members, the tab portions of each leaflet tab 162a, 162b can be arranged such that free ends 172a, 172b of the upper tab portions 164a, 164b and free ends 174a, 174b of the lower tab portions 166a, 166b are disposed between the wedge member 170 and a radially-outer side of the commissure window 114 along a radial direction of the frame 102.

One or more sutures can be used to couple together the wedge members and the wrapped leaflet tabs 162a, 162b. For example, as illustrated in FIG. 13, one or more second sutures 192 can be passed, through the first part 193b of the upper tab portion 164b of the second leaflet tab 162b (e.g., via through-holes 182b), the second part 191a of the upper tab portion 164a of the first leaflet tab 162a (e.g., via through-holes 180a), the wedge member 170, the first part 193a of the upper tab portion 164a of the first leaflet tab 162a (e.g., via through-holes 182a), and the second part 191a of the upper tab portion 164b of the second leaflet tab 162b (e.g., via through-holes 180b), in order or vice versa. The one or more second sutures 192 can be passed through the first and second parts of the lower tab portions 166a, 166b of the first and second leaflet tabs 162a, 162b and the wedge member 170 in a similar manner. In some embodiments, the second leaflet tab 162b can be wrapped around the first leaflet tab 162a and the one or more wedge members prior to coupling the first leaflet tab 162a to the wedge member(s) 170. In such embodiments, the first suture(s) 190 can be omitted in favor of coupling together the first and second leaflet tabs 162a, 162b and the wedge member(s) 170 using just the second suture(s) 192.

If the valvular structure includes other commissures to be attached to commissure windows of the frame, the method of FIGS. 11-13 can be repeated for the other commissures. In some embodiments, the valvular structure can have a tricuspid configuration with three leaflets, and the three commissures of the valvular structure are coupled to respective commissure windows of the frame by performing the process of FIGS. 11-13 three separate times. In other embodiments, the valvular structure can have a bicuspid configuration with two leaflets, and the two commissures of the valvular structure are coupled to respective commissure windows of the frame by performing the method of FIGS. 11-13 two separate times. In any of the embodiments with multiple commissures and commissure windows, performance of some or all of the method for the respective commissures can occur in parallel. For example, the leaflet tabs for each commissure can be inserted into their respective windows and then the first leaflet tabs can be wrapped around and coupled to respective wedge members. Other variations for parallel assembly of multiple commissures to multiple commissure windows are also possible according to one or more contemplated embodiments.

The method of assembly described with respect to FIGS. 11-13 provides a simple and cost-effective methodology for installing commissure assemblies to respective windows of the valve frame. For example, the arrangement of FIG. 11 can allow the leaflet tabs 162a, 162b to be quickly and easily inserted through the respective upper and lower openings of the commissure window. Moreover, the assembly of the leaflet tabs and subsequent mounting to the window using one or more wedge members involves a relatively small number of distinct components and assembly stages.

In some embodiments, adjacent leaflet tabs of a commissure can be coupled a wedge member prior to insertion through the commissure window. An upper tab portion of the first leaflet tab of the commissure can be wrapped around a wedge member, and then coupled to an upper tab portion of the second leaflet tab. The lower tab portion of the first leaflet tab and the upper and lower tab portions of the second leaflet tab can remain unfolded. The lower tab portions of the first and second leaflet tabs can be passed through the lower opening of the commissure window from the radially-inner side to the radially-outer side of the commissure window, and the upper tab portion of the second leaflet tab can be passed through the upper opening of the commissure window from the radially-inner side to the radially-outer side of the commissure window. The wedge member and the upper tab portion of the first leaflet tab can be passed over the open end of the upper opening of the commissure window to the radially outer-side of the commissure window, such that a portion of the upper tab slides into the upper opening of the commissure window. The lower tab portion of the first leaflet tab can then be wrapped around the wedge member, and the upper and lower tab portions of the second leaflet tab can be wrapped around the respective portions of the first leaflet tab. The wedge member can increase a width of the combination of the first and second folded leaflet tabs such that the leaflet tabs cannot pass back through the window.

Figures 14, 15:
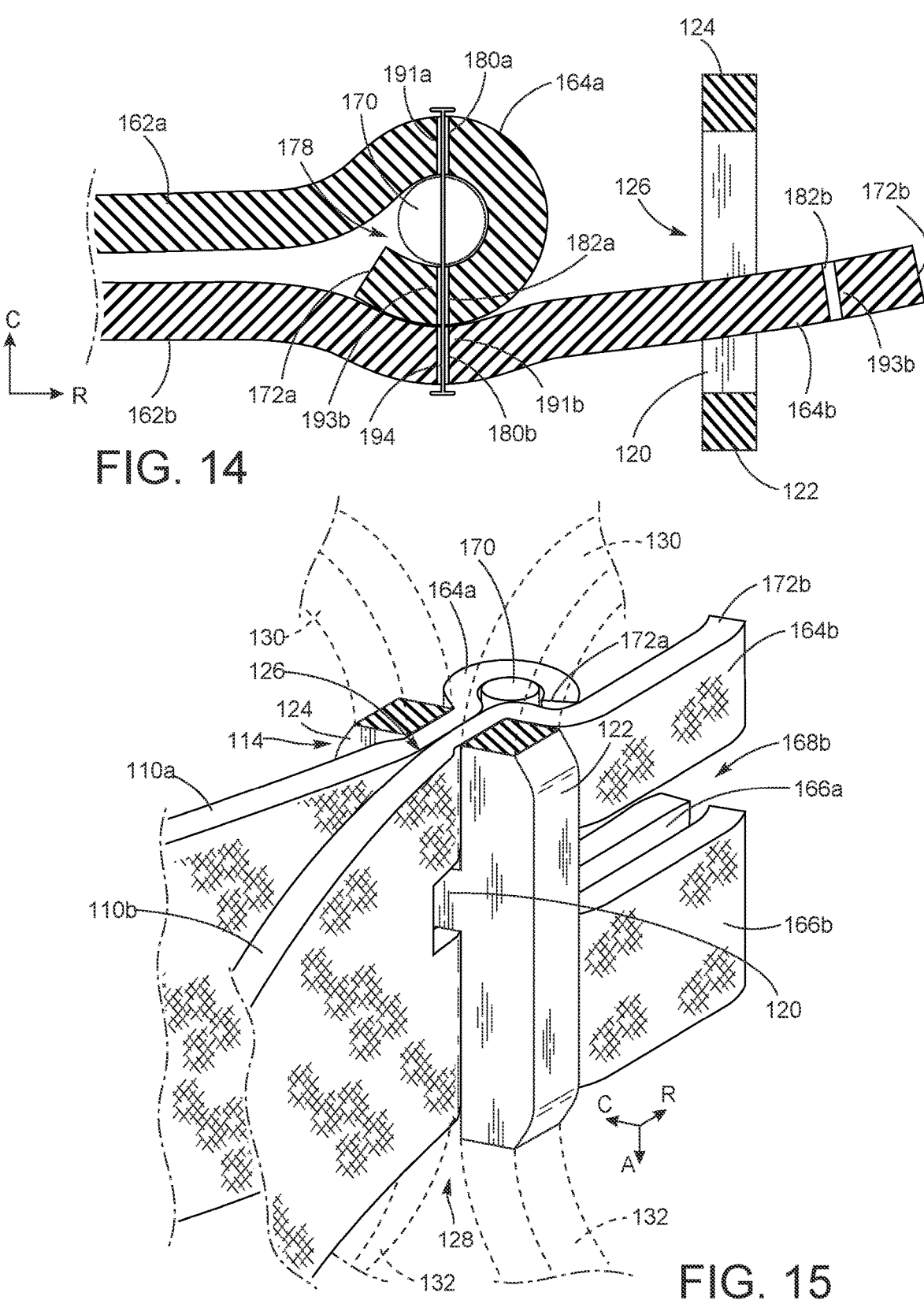
FIG. 14 is a simplified top-down view that illustrates coupling of a pair of leaflet tabs of a commissure and a wedge member prior to insertion through an H-shaped commissure window, according to a third exemplary assembly method.
FIG. 15 is a simplified perspective view that illustrates the commissure and wedge of FIG. 14 after insertion through the H-shaped commissure window, according to the third exemplary assembly method.

For example, FIGS. 14-15 illustrate a third exemplary method of installing a commissure 112 to an H-shaped commissure window 114. As described in detail above, each leaflet tab 162a, 162b for the commissure can have respective upper tab portions 164a, 164b and lower tab portions 166a, 166b separated by a gap 168a, 168b. Each upper tab portion 162a,b can have a first part 193a,b that is adjacent to a free end 172a,b of the upper tab portion and a second part 191a,b that is between the first part 193a,b and the centerline of the leaflet, and each lower tab portion can have a first part that is adjacent to a free end of the lower tab portion and a second part that is between the first part and the centerline of the leaflet. In some embodiments, the respective first and second parts of the upper tab portions 164a,b and the lower tab portions 166a,b can optionally be provided with one or more holes (e.g., through-holes 180a,b and 182a,b), through which one or more sutures can be passed to couple the tab portions and/or a wedge member together.

The upper tab portion 164a of the first leaflet tab 162a can be wrapped around a wedge member 170. The wrapped upper tab portion 164a of the first leaflet tab 162a can then be disposed adjacent to the upper tab portion 164b of the second leaflet tab 162b, which remains unfolded. Thus, the first part 193a of the upper tab portion 164a of the first leaflet tab 162a can contact, or at least face, the second part 191b of the upper tab portion of the second leaflet tab 162b, as shown in FIG. 14. Simultaneously or sequentially, the lower tab portions of the first and second leaflet tabs 162a, 162b can be disposed adjacent to each other and unfolded. One or more sutures can be used to couple together the wedge member 170 and the upper tab portions 164a, 164b of the first and second leaflet tabs 162a, 162b. For example, as illustrated in FIG. 14, one or more first sutures 194 can be passed through the second part 191b of the upper tab portion 164b of the second leaflet tab 162b (e.g., via through-holes 180b), the first part 193a of the upper tab portion 164a of the first leaflet tab 162a (e.g., via through-holes 182a), the wedge member 170, and the second part 191a of the upper tab portion 164a of the first leaflet tab 162a (e.g., via through-holes 180a), in order or vice versa.

Alternatively, the one or more sutures 194 can be used to couple the leaflet tabs 162a, 162b together before the wrapping of the first leaflet tab 162a. For example, the first leaflet tab 162a can be disposed in a substantially flat configuration on the second leaflet tab 162b and extending in an opposite direction from the second leaflet tab 162b, such that the centerlines of the leaflets are on opposite sides of overlapping portions of the first and second leaflet tabs 162a, 162b. Thus, the first parts 193a of the upper and lower tab portions 164a, 166a of the first leaflet tab 162a can be aligned with the second parts 191b of the upper and lower tab portions 164b, 166b of the second leaflet tab 162b, and the first parts 193b of the upper and lower tab portions 164b, 166b of the second leaflet tab 162b can be aligned with the second parts 191a of the upper and lower tab portions 164a, 166a of the first leaflet tab 162a. The wedge member 170 can be disposed atop the first part 193a of the upper tab portion 162a of the first leaflet tab 162a. In this overlapping configuration, the one or more first sutures 194 may be passed through the wedge member 170, the first part 193a of the upper tab portion 164a of the first leaflet tab 162a, and the second part 191b of the upper tab portion 164b of the second leaflet tab 162b, in order or vice versa. After the leaflet tabs are coupled together, the upper tab portions 164a can then be wrapped around the wedge member 170, as described above.

The wedge member 170 can extend to the lower tab portions 166a, 166b of the first and second leaflet tabs 162a, 162b, and attaching the wedge member 170 to the lower tab portions 166a, 166b would prevent the commissure from passing through the commissure window due to the intervening crossbar 120. Thus, the lower tab portions 166a, 166b can remain unattached to the wedge member 170 at this stage. This allows the lower tab portions 166a, 166b to be inserted through the lower opening 128 of commissure window 114, for example, in a manner similar to that described above with respect to FIG. 11. Before, during, or after the insertion of the lower tab portions 166a, 166b, the wedge member 170 can be passed over the upper end of upper opening 126 of the commissure window 114 (e.g., by passing over the outflow end 116 of the valve frame 102, from the radially-inner side of the window 114 to the radially-outer side of the window 114). The upper tab portions 164a, 164b can thus be inserted into the upper opening 126, for example, along a direction parallel to the axial direction of the frame 102 or a combination of axial and radial components. Alternatively or additionally, a cross-sectional dimension of the wedge member 170 can be such that the combination of wrapped upper tab portion 164a of the first leaflet tab 162a, the unfolded upper tab portion 164b of the second leaflet tab 162b, and the wedge member 170 is able to fit through the upper opening 126. To avoid the crossbar 120 as the upper tab portions pass through the upper opening 126, the wedge member 170 may be temporarily tilted to extend along the radial direction of the frame and can pass through the upper opening 126 prior to or with the free end 172b of the upper tab portion 164b of the second leaflet tab 162b. In either case, the wedge member 170 avoids the crossbar 120 of the window 114, thereby allowing the wedge member 170 to be attached to the upper tab portions 162a, 162b at the radially-inner side of the commissure window while still permitting the upper tab portions 162a, 162b to inserted through the upper opening 126 of the commissure window 114.

With the upper and lower tab portions of the first and second leaflets 162a, 162b inserted through the respective openings 126, 128 and the wedge member 170 on the radially-outer side of the window 114 as shown in FIG. 14, the lower tab portion 166a can be wrapped around the wedge member 170. The upper tab portion 164b of the second leaflet tab 162b can be wrapped around the upper tab portion 164a of the first leaflet tab 162a, and the lower tab portion 166b of the second leaflet 162b can be wrapped around the lower tab portion 166a of the first leaflet tab 162a, resulting in a configuration similar to that illustrated in FIG. 13. Similar to the above described embodiments, one or more sutures can be used to couple together the wedge member 170 and the folded leaflet tabs 162a, 162b. For example, similar to the configuration of FIG. 13, one or more second sutures 192 can be passed, through the first part 193b of the upper tab portion 164b of the second leaflet tab 162b (e.g., via through-holes 182b), the second part 191a of the upper tab portion 164a of the first leaflet tab 162a (e.g., via through-holes 180a), the wedge member 170, the first part 193a of the upper tab portion 164a of the first leaflet tab 162a (e.g., via through-holes 182a), and the second part 191a of the upper tab portion 164b of the second leaflet tab 162b (e.g., via through-holes 180b), in order or vice versa.

The one or more second sutures 192 can be passed through the first and second parts of the lower tab portions 166a, 166b of the first and second leaflet tabs 162a, 162b and the wedge member 170 in a similar manner.

If the valvular structure includes other commissures to be attached to commissure windows of the frame, the method of FIGS. 14-15 can be repeated for the other commissures. In some embodiments, the valvular structure can have a tricuspid configuration with three leaflets, and the three commissures of the valvular structure are coupled to respective commissure windows of the frame by performing the process of FIGS. 14-15 three separate times. In other embodiments, the valvular structure can have a bicuspid configuration with two leaflets, and the two commissures of the valvular structure are coupled to respective commissure windows of the frame by performing the method of FIGS. 14-15 two separate times. In any of the embodiments with multiple commissures and commissure windows, performance of some or all of the method for the respective commissures can occur in parallel. For example, the leaflet tabs for each commissure can be wrapped around respective wedge members and then coupled together at the same time, after which the coupled leaflet tabs can be inserted into their respective windows. Other variations for parallel assembly of multiple commissures to multiple commissure windows are also possible according to one or more contemplated embodiments.

The method of assembly described with respect to FIGS. 14-15 provides a simple and cost-effective methodology for installing commissure assemblies to respective windows of the valve frame. For example, the arrangement of FIG. 11 can allow the leaflet tabs 162a, 162b to be quickly and easily inserted through the respective upper and lower openings of the commissure window. Moreover, the assembly of the leaflet tabs and subsequent mounting to the window using one or more wedge members involves a relatively small number of distinct components and assembly stages.

In some embodiments, upper and lower tab portions of adjacent leaflet tabs can be coupled to separate wedge members prior to insertion through the commissure window. For example, an upper tab portion of the first leaflet tab of the commissure can be wrapped around a first wedge member, and then coupled to an upper tab portion of the second leaflet tab, which remains unfolded. Similarly, a lower tab portion of the first leaflet tab of the commissure can be wrapped around a second wedge member, and then coupled to a lower tab portion of the second leaflet tab, which remains unfolded. The configuration for upper and lower tab portions can be similar to that illustrated in FIG. 14, but with upper tab portion having a wedge member 170 separate from that of the lower tab portion.

The cross-sectional dimension of each wedge member can be such that the combination of wrapped upper tab portion of the first leaflet tab, first wedge member, and unfolded upper tab portion of the second leaflet tab fits through the upper opening of the commissure window, and the combination of wrapped lower tab portion of the first leaflet tab, second wedge member, and unfolded lower tab portion of the second leaflet tab fits through the lower opening of the commissure window. Since there is no wedge member extending between the upper and lower tab portions that would otherwise obstruct passage of the commissure through the window due to crossbar 120, the upper and lower tab portions of the first and second leaflet tabs can be passed through the upper and lower openings of the commissure window, respectively, from the radially-inner side to the radially-outer side of the commissure window.

The second leaflet tab can then be wrapped around and further coupled to the first leaflet tab and the wedge members, resulting in a structure similar to that described above with respect to FIG. 6, 10, or 13. Each wedge member can increase a width of the combination of the wrapped first and second leaflet tabs such that the leaflet tabs is prevented, or at least restrained, from passing back through the window. In such embodiments, the multiple wedge members can be coupled together (e.g., via stitching using one or more sutures) and/or the upper and lower tab portions on the radially-outer side of the commissure window 114 can be coupled together (e.g., via stitching using one or more sutures), for example, to prevent sliding along the axial direction of the respective tab portions. As with the other described embodiments, if the valvular structure includes other commissures to be attached to commissure windows of the frame, the method can be repeated for the other commissures.

In some embodiments, the upper tab portion of the first and second leaflet tabs can be inserted through the upper opening and attached to the commissure window 114 and/or the lower tab portion of the first and second leaflet tabs can be inserted through the lower opening and attached to the commissure window 114, using any of the assembly techniques disclosed in U.S. Provisional Application No. 62/959,723, which is incorporated herein by reference.

In some embodiments, the leaflet tabs of each leaflet of the valvular structure can be formed without separate upper and lower tab portions, for example, without gaps 168. In such embodiments, the leaflet tabs can have a configuration similar to those described in U.S. Provisional Application No. 62/959,723 and the other applications and publications incorporated by reference above. In some embodiments, these leaflet tabs can be inserted into either the upper opening or the lower opening of the commissure window 114. Since the leaflet tabs are only inserted into half of the H-shaped commissure window 114, the commissure window 114 may be considered a U-shaped window in such embodiments.

In any of the disclosed examples or embodiments, a coupling member, such as a flexible cloth or fabric, can be disposed around surfaces of the leaflet tabs and or the wedge member(s). For example, the coupling member can be attached to the wedge member(s) and the tabs prior to installation in the commissure window. In some embodiments, the coupling member can be wrapped around portions of the commissure window (e.g., struts 122, 124) to further secure the leaflet tabs to the commissure window and/or protect portions of the leaflets from abrasion.

Figures 17A, 17B:
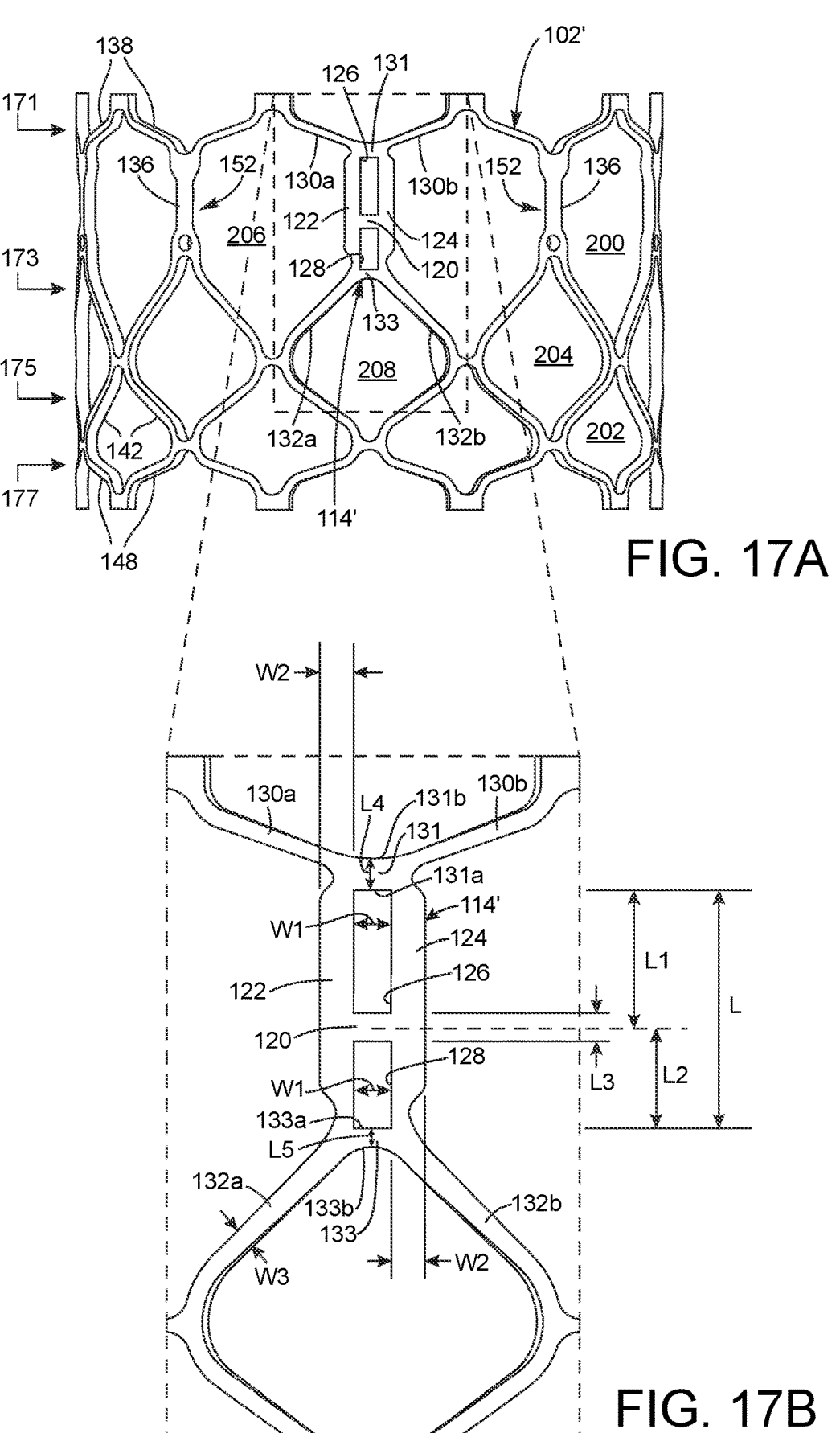
FIGS. 17A-17B are side and detail views, respectively, of another exemplary H-shaped commissure window of the prosthetic heart valve frame of FIG. 2.

FIGS. 17A and 17B illustrate an alternative frame 102' with commissure windows 114' according to another example. In some embodiments, the prosthetic valve 100 can include the frame 102' instead of the previously described frame 102. The frame 102' is similar in many respects to the frame 102 except for the details of the commissure windows. Similar reference numbers are used for parts of the frame 102' that are similar or the same as parts of the frame 102. For purposes of illustration, only the bare frame 102' is shown in FIGS. 17A and 17B. It should be understood that any of the other components of the prosthetic valve 100 (e.g., leaflets 100, inner skirt 108, outer skirt 104, etc.) can be assembled onto the frame 102' in the manner shown in FIG. 1 and described above.

In the example illustrated in FIGS. 17A and 17B, each commissure window 114' can include window struts 122, 124, which extend along the axial direction of the frame 102' and are spaced along the circumferential direction of the frame 102'. Each commissure window 114' can include a crossbar 120 extending between and connected to the window struts 122, 124. Each commissure window 114' can include a first, upper opening 126 (or upper window portion or downstream window portion) formed on one side of the crossbar 120 and a second, lower opening 128 (or lower window portion or upstream window portion) formed on the other side of the crossbar 120.

Each commissure window 114' can further include an upper lateral strut portion 131 extending between the upper ends of the window struts 122, 124 and forming a closed end of the upper opening 126. In one example, an upper angled strut 130a is connected to an upper end of the window strut 122, and an upper angled strut 130b is connected to an upper end of the window strut 124. The upper lateral strut portion 131 extends between the junction formed between the upper angled strut 130a and the window strut 122 and the junction formed between the upper angled strut 130b and the window strut 124. The upper lateral strut portion 131 can thereby increase the stability of the window struts 122, 124 at the upper ends.

Each commissure window 114' can further include a lower lateral strut portion 133 extending between the lower ends of the window struts 122, 124 and forming a closed end of the lower opening 128. In one example, a lower angled strut 132a is connected to a lower end of the window strut 122, and a lower angled strut 132b is connected to a lower end of the window strut 124. The lower lateral strut portion 133 extends between the junction formed between the lower angled strut 132a and the window strut 122 and the junction formed between the lower angled strut 132a and the window strut 124. The lower lateral strut portion 133 can thereby increase the structural stability of the window struts 122, 124 at the lower ends.

The lateral strut portions 131, 133 are spaced in the axial direction of the frame 102' and extend in the circumferential direction of the frame 102'. The upper opening 126 is enclosed by the window struts 122, 124, the upper lateral strut portion 131, and the crossbar 120. The lower opening 128 is enclosed by the window struts 122, 124, the lower lateral strut portion 133, and the crossbar 120. The resulting commissure window 114' can be described as having an H-shape with closed ends, where the window struts 122, 124 and the crossbar 120 form the H-shape (as in the previously described commissure window 114) and the lateral strut portions 131, 133 form the closed ends.

The inner surface 131a of the upper lateral strut portion 131 that faces the upper opening 126 can be flat as shown, or it can be curved (e.g., concave) in other examples. The outer surface 131b of the upper lateral strut portion 131 that extends between the upper angled struts 131a, 131b can be curved. In some cases, the outer surface 131b may include a notch (e.g., a U-shaped notch), as shown, for example, at the ends of the struts 136. The inner surface 133a of the lower lateral strut portion 133 that faces the opening 128 can be flat as shown, or it can be curved (e.g., concave) in other examples. The outer surface 133b of the lateral strut portion 133 that extends between the lower angled struts 132a, 132b can be curved. In some cases, the outer surface 133b may include a notch (e.g., U-shaped notch), as shown, for example, at the ends of the struts 136.

An axial distance measured from the inner surface 131a of the upper lateral strut portion 131 to a midline of the crossbar 120 can be represented by the length $L_1$. An axial distance measured from the inner surface 133a of the lower lateral strut portion 133 to the midline of the crossbar 120 can be represented by the length $L_2$. The axial distance measured from the inner surface 131a of the upper lateral strut portion 131 to the inner surface 133a of the lower lateral strut portion 131 can be represented by the length L, which is the sum of the lengths $L_1$ and $L_2$. The thickness of the crossbar 120 in the axial direction can be represented by the length $L_3$.

The ratio $L_1/L_2$ determines the axial position of the crossbar 120 relative to the window struts 112, 124 (or the relative to the lateral strut portions 131, 133). In one example, the ratio $L_1/L_2$ can be greater than or equal to 1. When $L_1/L_2$ is equal to 1, the crossbar 120 is positioned at the midpoint of each window strut 122, 124 along the axial direction. When $L_1/L_2$ is greater than 1, the upper opening 126 is taller than the lower opening 128, and the crossbar 120 is positioned closer to the lower lateral strut portion 133 than to the upper lateral strut portion 131. $L_1/L_2$ greater than 1 may allow the commissure window 114' to carry a higher load in the upper window portion. In one example, $L_1/L_2$ can be in a range from 1 to 3.

The length of the upper opening 126 is $L_1-\frac{1}{2}L_3$. The length of the lower opening 128 is $L_2-\frac{1}{2}L_3$. The leaflets can experience greater stress along the upper opening 126 since the leaflet free edge (i.e., the edge of the leaflet that coapts with the free edges of the other leaflets to close the prosthetic valve and moves away from the free edges of the other leaflets to open the prosthetic valve) is attached to this opening. In some cases, a longer $L_1$ can help prevent tearing at the portion of the commissure formed in the upper opening 126. In other cases, a longer $L_1$ can allow use of a high tab, which is a commissure tab that is slightly higher than the leaflet outflow. A high tab can allow better stress distribution at the top of the commissure.

Figure 18:
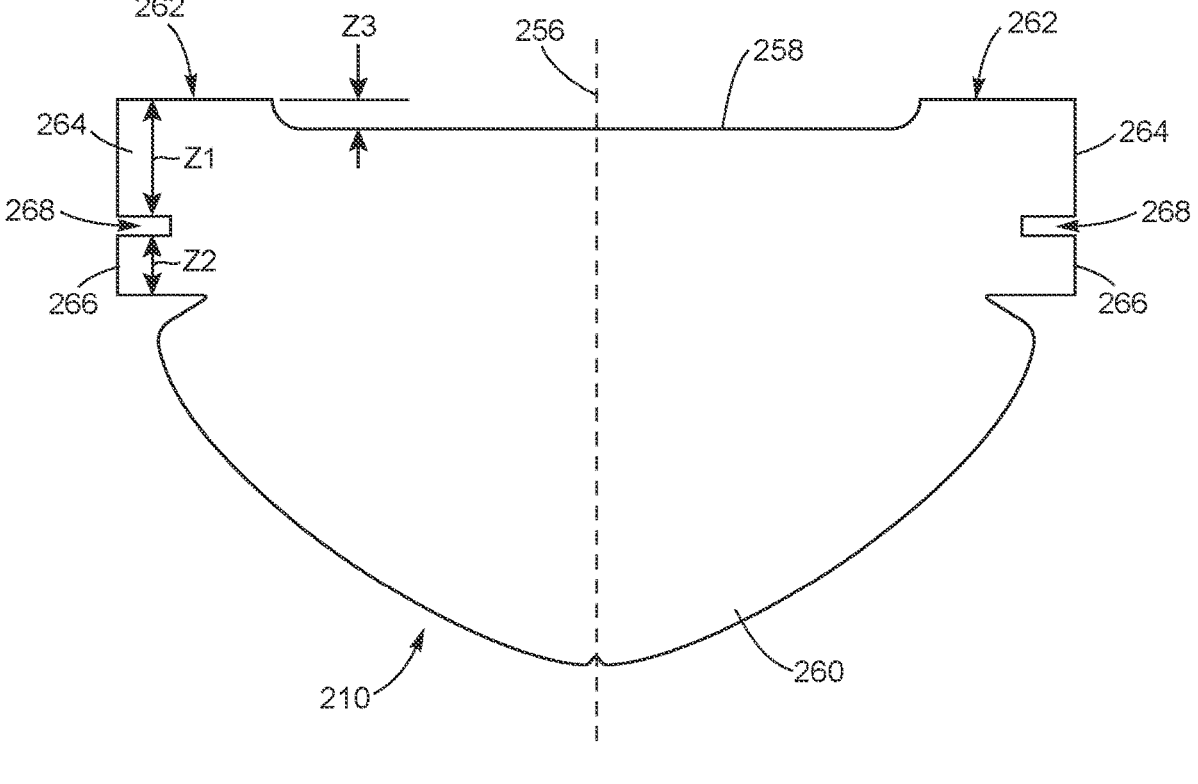
FIG. 18 is a plan view of an individual leaflet that can be incorporated in any of the prosthetic valves disclosed herein.

FIG. 18 illustrates an example of a leaflet 210 with a relatively high commissure tab. The leaflet 210 can include a main, cusp edge portion 260, two leaflet tabs 262 (or commissure tabs), and a leaflet free edge 258 (or coaptation edge). In the orientation of the drawing, the cusp edge portion 260 forms a lower edge portion of the leaflet 210, and the leaflet free edge 258 forms an upper edge of the leaflet 210. The leaflet tabs 262 project from opposite side edges of the leaflet 210. In some cases, the leaflet tabs 262 can be symmetrical about a centerline 256 of the leaflet. Each of the tabs 262 can include an upper tab portion 264 and a lower tab portion 266 separated by a notch 268 (or slit). In one example, the height $Z_1$ of each upper tab portion 264 can be greater than the height $Z_2$ of the respective lower tab portion 266. In one example, the upper tab portions 264 can extend slightly above the leaflet free edge 258 by a height $Z_3>0$. For example, height $Z_3$ can be in a range from 0.5 to 2 mm.

A leaflet assembly composed of a plurality of leaflets 210 (e.g., three leaflets 210) can be coupled to an annular frame using the commissure windows 114' (shown in FIGS. 17A and 17B). The assembly can include extending the high upper tab portions 264 of adjacent leaflets 210 through the upper openings 126 of the commissure windows 114' to form upper portions of the commissures and extending the lower tab portions 266 through the lower openings 128 of the commissure windows 114' to form the lower portions of the commissures. The process of forming the commissures can be as previously described with respect to commissure window 114. In the example where the upper tab portions 264 extend above the leaflet free edge 258, as shown in FIG. 18, bumps will be formed at the entrance of the commissure windows 114'. These bumps can allow better stress distribution at the top of the commissures formed at the commissure windows 114' by the leaflet tabs 262.

Returning to FIG. 17B, the length $L_3$ (i.e., the thickness of the crossbar 120 in the axial direction) is normally significantly less than each of lengths $L_1$ and $L_2$. At the same time, the length $L_3$ should be large enough to provide the crossbar 120 with sufficient strength to prevent the window struts 122, 124 from buckling too much under load. The length $L_3$ can be determined by analysis of the forces acting on the commissure window 114' during transition of the frame 102' from the crimped configuration to the fully expanded configuration. In one example, the length $L_3$ can have a minimum value of 0.2 mm. In another example, the length $L_3$ can have a minimum value of 0.4 mm.

The minimum thickness of the lateral strut portion 131 in the axial direction can be represented by the length $L_4$, and the minimum thickness of the lateral strut portion 133 in the axial direction can be represented by the length $L_5$. The lengths $L_4$ and $L_5$ can be the same or can be different, and each length $L_4$, $L_5$ should be large enough to provide the respective lateral strut portion with sufficient strength to prevent the window struts 122, 124 from buckling too much under load. The lengths $L_4$ and $L_5$ can be determined by analysis of the forces acting on the commissure window 114' during transition of the frame 102 from the crimped configuration to the fully expanded configuration. In one example, each of the lengths $L_4$ and $L_5$ can have a minimum value of 0.2 mm. In another example, each of the lengths $L_4$ and $L_5$ can have a minimum value of 0.4 mm.

The openings 124, 126 (or the gap between the window struts 122, 124) can have a width $W_1$. The size of the width $W_1$ can be selected to accommodate two leaflet tabs, sutures, and/or fabric involved in forming commissures, while taking into account compression of the leaflet tabs. In one example, the width $W_1$ can be in a range from 0.5 to 1 mm. The width of the window struts 122, 124 can be represented by $W_2$. The width $W_2$ is selected based on strength considerations. In one example, the width $W_2$ is selected such that the window struts 122, 124 do not bend during crimping/expansion and during cycling. The size of the width $W_2$ can be determined by force analysis (e.g., using finite element analysis) of the frame 102' when the frame 102' transitions between the crimped and fully expanded configurations and when the leaflets of the valvular structure attached to the frame are cycling between open and closed portions. In one example, the width $W_2$ can be in a range from 0.2 to 0.5 mm.

The crossbar 120 and the lateral strut portions 131, 133 can enable the commissure window 114' to be elongated in form. Elongated commissure windows can accommodate longer leaflet tabs (the length being measured in the axial direction), which are useful in relieving stresses applied to the leaflets during the transition between the systolic and diastolic phases. The crossbar 120 divides the commissure window into sub-windows such that the window strut portions of each sub-window extend over a shorter length, allowing the sub-window to retain its structural integrity and resist bending/plastic deformation under load, such as when the prosthetic valve is crimped to a radially compressed state. The lateral strut portions 131, 133 affixed to the ends of the window struts 122, 124 advantageously increase the structural stability of the window struts 122, 124.

The prosthetic valve 100 (shown in FIG. 1) can be constructed by disposing the valvular structure 106 (shown in FIG. 1) within the frame 102' and installing commissures at the commissure windows 114' to attach the leaflets of the valvular structure to the frame, as previously described and illustrated in FIGS. 6-15. The dimensions of the commissure window 114' as defined by $W_1$, $W_2$, $L_1$, $L_2$, $L_3$, $L_4$, $L_5$ in FIG. 17B can be tailored to avoid formation of convex or concave contours along the window struts 122, 124 when the frame 102' is under load (such as during crimping of the prosthetic valve or during transition of the prosthetic valve from the crimped configuration to the fully expanded configuration or during cycling of the leaflets). The dimensions can be determined, for example, by modeling the forces acting on the window struts 122, 124 when the frame 102' is under load.

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1

An assembly method for a prosthetic heart valve comprises (a) providing first and second leaflets for a valvular structure of the prosthetic heart valve, each leaflet having a pair of tabs, one of the tabs being on an opposite side from the other of the tabs with respect to a centerline of the leaflet, each tab having an upper tab portion and a lower tab portion separated from the upper tab portion along a direction parallel to the centerline by a gap; (b) disposing the upper and lower tab portions of a second tab of the pair of tabs of the second leaflet adjacent to the upper and lower tab portions of a first tab of the pair of tabs of the first leaflet, respectively; (c) stitching together the upper tab portions of the first and second leaflet tabs, and stitching together the lower tab portions of the first and second leaflet tabs; (d) folding the upper and lower tab portions of the first leaflet tab; (e) conveying the first and second leaflet tabs through a commissure window of an expandable annular frame of the prosthetic heart valve, the commissure window having upper and lower openings separated from each other along an axial direction of the annular frame by a crossbar, the conveying being along a radial direction of the annular frame from a radially inner-side of the commissure window to a radially-outer side of the commissure window and such that the upper tab portions are inserted through the upper opening and the lower tab portions are inserted through the lower opening; (f) inserting one or more wedge members between facing surfaces of the folded upper tab portion of the first leaflet tab and between facing surfaces of the folded lower tab portion of the first leaflet tab; (g) folding the upper tab portion of the second leaflet tab around the folded upper tab portion of the first leaflet tab, and folding the lower tab portion of the second leaflet tab around the folded lower tab portion of the first leaflet tab; and (h) after inserting the one or more wedge members as described in (f), stitching together the one or more wedge members and the upper tab portions of the first and second leaflet tabs, and stitching together the one or more wedge members and the lower tab portions of the first and second leaflet tabs.

Example 2

An assembly method according to any example herein, particularly example 1, wherein the upper and lower openings of the commissure window are disposed to form an H-shape in side view; the H-shaped commissure window has a pair of struts that each extend along the axial direction of the annular frame; and the crossbar extends along a circumferential direction of the annular frame between the pair of struts.

Example 3

An assembly method according to any example herein, particularly example 2, wherein the crossbar is offset from a midpoint of each strut along the axial direction.

Example 4

An assembly method according to any example herein, particularly example 3, wherein each strut has a first end adjacent to the upper opening and a second end adjacent to the lower opening, a distance, $L_1$, along the axial direction from the first end of each strut to a middle of the crossbar along the axial direction is less than a distance, $L_2$, along the axial direction from the middle of the crossbar to the second end of each strut, and $L_1/L_2$ is within a range of 0.25 to 0.35, inclusive.

Example 5

An assembly method according to any example herein, particularly any of examples 1 to 4, wherein the stitching in (c) is by at least one first suture.

Example 6

An assembly method according to any example herein, particularly example 5, wherein the at least one first suture is a single first suture that stitches together the upper tab portions of the first and second leaflet tabs and the lower tab portions of the first and second leaflet tabs.

Example 7

An assembly method according to any example herein, particularly example 5, wherein the at least one first suture is a pair of first sutures, one of the pair of first sutures stitching together the upper tab portions of the first and second leaflet tabs, and the other of the pair of first sutures stitching together the lower tab portions of the first and second leaflet tabs.

Example 8

An assembly method according to any example herein, particularly any of examples 1 to 7, wherein the stitching in (h) is by at least one second suture.

Example 9

An assembly method according to any example herein, particularly example 8, wherein the at least one second suture is a single second suture that stitches together the one or more wedge members, the upper tab portions of the first and second leaflet tabs, and the lower tab portions of the first and second leaflet tabs.

Example 10

An assembly method according to any example herein, particularly example 8, wherein the at least one second suture is a pair of second sutures, one of the pair of second sutures stitching together the one or more wedge members and the upper tab portions of the first and second leaflet tabs, and the other of the pair of second sutures stitching together the one or more wedge members and the lower tab portions of the first and second leaflet tabs.

Example 11

An assembly method according to any example herein, particularly any of examples 1 to 10, wherein the upper tab portion of each leaflet tab has a first part that is adjacent to a free end of said upper tab portion and a second part that is between the first part and the centerline of the leaflet; and wherein the lower tab portion of each leaflet tab has a third part that is adjacent to a free end of said lower tab portion and a fourth part that is between the third part and the centerline of the leaflet.

Example 12

An assembly method according to any example herein, particularly example 11, wherein the stitching in (c) comprises stitching the first part of the upper tab portion of the first leaflet tab to the second part of the upper tab portion of the second leaflet tab and stitching the third part of the lower tab portion of the first leaflet tab to the fourth part of the lower tab portion of the second leaflet tab; and wherein after the stitching in (c) and before the stitching in (h), the first part of the upper tab portion of the second leaflet tab, the second part of the upper tab portion of the first leaflet tab, the third part of the lower tab portion of the second leaflet tab, and the fourth part of the lower tab portion of the first leaflet tab are not stitched.

Example 13

An assembly method according to any example herein, particularly any of examples 11 and 12, wherein after the folding in (g), the first part of the upper tab portion of the second leaflet tab contacts the second part of the upper tab portion of the first leaflet tab, and the third part of the lower tab portion of the second leaflet tab contacts the fourth part of the lower tab portion of the first leaflet tab.

Example 14

An assembly method according to any example herein, particularly any of examples 11 to 13, wherein after the stitching in (h), the first part of the upper tab portion of the second leaflet tab, the second part of the upper tab portion of the first leaflet tab, the one or more wedge members, the first part of the upper tab portion of the first leaflet tab, and the second part of the upper tab portion of the second leaflet tab are disposed in order along the circumferential direction and stitched together. In addition, the third part of the lower tab portion of the second leaflet tab, the fourth part of the lower tab portion of the first leaflet tab, the one or more wedge members, the third part of the lower tab portion of the first leaflet tab, and the fourth part of the lower tab portion of the second leaflet tab are disposed in order along the circumferential direction and stitched together.

Example 15

An assembly method according to any example herein, particularly any of examples 11 to 14, wherein after the folding in (g), the free ends of the upper tab portions of the first and second leaflet tabs and the free ends of the lower tab portions of the first and second leaflet tabs are disposed along the radial direction between the one or more wedge members and the radially-outer side of the commissure window.

Example 16

An assembly method according to any example herein, particularly any of examples 11 to 15, wherein the folding in (d) is such that the second part of the upper tab portion of the first leaflet tab faces or is in contact with the first part of the upper tab portion of the first leaflet tab, and the fourth part of the lower tab portion of the first leaflet tab faces or is in contact with the third part of the lower tab portion of the first leaflet tab.

Example 17

An assembly method according to any example herein, particularly any of examples 1 to 16, further comprises (i) providing a third leaflet for the valvular structure, the third leaflet also having a pair of tabs, one of the tabs being on an opposite side from the other of the tabs with respect to a centerline of the third leaflet, each tab having an upper tab portion and a lower tab portion separated from the upper tab portion along a direction parallel to the centerline by a gap; (j) disposing the upper and lower tab portions of a fourth tab of the pair of tabs of either the first leaflet or the second leaflet adjacent to the upper and lower tab portions of a third tab of the pair of tabs of the third leaflet, respectively; (k) stitching together the upper tab portions of the third and fourth tabs, and stitching together the lower tab portions of the third and fourth tabs; (l) folding the upper and lower tab portions of the third leaflet tab; (m) conveying the third and fourth tabs through a second commissure window of the annular frame, the second commissure window having second upper and second lower openings separated from each other along the axial direction by a second crossbar, the conveying being along the radial direction from a radially inner-side of the second commissure window to a radially-outer side of the second commissure window and such that the upper tab portions are inserted through the second upper opening and the lower tab portions are inserted through the second lower opening; (n) inserting one or more second wedge members between facing surfaces of the folded upper tab portion of the third tab and between facing surfaces of the folded lower tab portion of the third tab; (o) folding the upper tab portion of the fourth tab around the folded upper tab portion of the third tab, and folding the lower tab portion of the fourth tab around the folded lower tab portion of the third tab; and (p) after (n), stitching together the one or more second wedge members and the upper tab portions of the third and fourth tabs, and stitching together the one or more second wedge members and the lower tab portions of the third and fourth tabs.

Example 18

An assembly method according to any example herein, particularly any of examples 1 to 17, wherein each wedge member comprises at least one of a braided suture, a braided cable, or a folded piece of cloth.

Example 19

An assembly method according to any example herein, particularly any of examples 1 to 18, wherein each commissure window is an integral part of the expandable annular frame of the prosthetic heart valve.

Example 20

An assembly method according to any example herein, particularly any of examples 1 to 18, wherein each commissure window is a part of a respective support member that forms a part of or is coupled to the expandable annular frame of the prosthetic heart valve.

Example 21

An assembly method according to any example herein, particularly example 20, wherein the support member comprises a portion of an actuator or locking mechanism of the prosthetic heart valve, or is coupled to an actuator or locking mechanism of the prosthetic heart valve.

Example 22

An assembly method according to any example herein, particularly any of examples 11 to 21, wherein one or more of the first through fourth parts includes one or more through-holes therein.

Example 23

An assembly method according to any example herein, particularly example 22, wherein the stitching in (c) comprises passing one or more sutures through the through-holes of the first part of the upper tab portion of the first leaflet tab and of the second part of the upper tab portion of the second leaflet tab, and passing one or more sutures through the through-holes of the third part of the lower tab portion of the first leaflet tab and of the fourth part of the lower tab portion of the second leaflet tab.

Example 24

An assembly method according to any example herein, particularly any of examples 22 and 23, wherein the stitching in (h) comprises passing one or more sutures through the through-holes of the first and second parts of the upper tab portion of the second leaflet tab, and passing one or more sutures through the through-holes of the third and fourth parts of the lower tab portion of the second leaflet tab.

Example 25

An assembly method according to any example herein, particularly any of examples 1 to 24, wherein the one or more wedge members comprises a single continuous wedge member.

Example 26

An assembly method according to any example herein, particularly any of examples 1 to 24, wherein the one or more wedge members comprises separate first and second wedge members, the first wedge member being inserted with respect to the upper tab portion of the first leaflet tab, the second wedge member being inserted with respect to the lower tab portion of the first leaflet tab.

Example 27

An assembly method according to any example herein, particularly any of examples 1 to 26, wherein the conveying of (e) is performed prior to the disposing of (b) or (c), and/or wherein the folding of (g) is performed prior to the inserting of (f).

Example 28

An assembly method for a prosthetic heart valve comprises (a) providing first and second leaflets for a valvular structure of the prosthetic heart valve, each leaflet having a pair of tabs, one of the tabs being on an opposite side from the other of the tabs with respect to a centerline of the leaflet, each tab having an upper tab portion and a lower tab portion separated from the upper tab portion along a direction parallel to the centerline by a gap; (b) disposing the upper tab portion of a first tab of the pair of tabs of the first leaflet to surround at least a portion of a circumference of a first wedge member, and disposing the lower tab portion of the first leaflet tab to surround at least a portion of a circumference of a second wedge member; (c) stitching together the first wedge member and at least the upper tab portion of the first leaflet tab, and stitching together the second wedge member and at least the lower tab portion of the first leaflet tab; (d) conveying the first wedge member, the second wedge member, and the first leaflet tab through a commissure window of an expandable annular frame of the prosthetic heart valve, the commissure window having upper and lower openings separated from each other along an axial direction of the annular frame by a crossbar, the conveying being along a radial direction of the annular frame from a radially inner-side of the commissure window to a radially-outer side of the commissure window, and such that the upper tab portion of the first leaflet tab and the first wedge member are inserted through the upper opening and the lower tab portion of the first leaflet tab and the second wedge member are inserted through the lower opening; (e) conveying a second tab of the pair of tabs of the second leaflet through the commissure window, the conveying being along the radial direction from the radially inner-side of the commissure window to the radially-outer side of the commissure window and such that the upper tab portion of the second leaflet tab is inserted through the upper opening and the lower tab portion of the second leaflet tab is inserted through the lower opening; (0 folding the upper tab portion of the second leaflet tab around the upper tab portion of the first leaflet tab, and folding the lower tab portion of the second leaflet tab around the lower tab portion of the first leaflet tab; and (g) after (f), stitching together the first wedge member, and the upper tab portions of the first and second leaflet tabs, and stitching together the second wedge member and the lower tab portions of the first and second leaflet tabs.

Example 29

An assembly method according to any example herein, particularly example 28, wherein the upper tab portion of each leaflet tab has a first part that is adjacent to a free end of said upper tab portion and a second part that is between the first part and the centerline of the leaflet; and wherein the lower tab portion of each leaflet tab has a third part that is adjacent to a free end of said lower tab portion and a fourth part that is between the third part and the centerline of the leaflet.

Example 30

An assembly method according to any example herein, particularly example 29, wherein, after the folding in (f), the first part of the upper tab portion of the second leaflet tab contacts the second part of the upper tab portion of the first leaflet tab, and the third part of the lower tab portion of the second leaflet tab contacts the fourth part of the lower tab portion of the first leaflet tab.

Example 31

An assembly method according to any example herein, particularly any of examples 29 and 30, wherein the stitching in (c) comprises stitching together the first part of the upper tab portion of the first leaflet tab, the first wedge member, and the second part of the upper tab portion of the first leaflet tab; and wherein stitching together the third part of the lower tab portion of the first leaflet tab, the second wedge member, and the fourth part of the lower tab portion of the first leaflet tab.

Example 32

An assembly method according to any example herein, particularly any of examples 29 and 30, further comprises prior to the stitching of (c), disposing the upper and lower tab portions of a second tab of the pair of tabs of the second leaflet adjacent to the upper and lower tab portions of the first leaflet tab, respectively. In the stitching of (c), the first wedge member and the upper tab portions of the first and second leaflet tabs are stitched together, and the second wedge member and the lower tab portions of the first and second leaflet tabs are stitched together. The conveying of (e) is performed simultaneously with the conveying of (d).

Example 33

An assembly method according to any example herein, particularly example 32, wherein the stitching in (c) comprises stitching together the first part of the upper tab portion of the first leaflet tab, the first wedge member, the second part of the upper tab portion of the first leaflet tab, and the second part of the upper tab portion of the second leaflet tab. The stitching in (c) further comprises stitching together the third part of the lower tab portion of the first leaflet tab, the second wedge member, the fourth part of the lower tab portion of the first leaflet tab, and the fourth part of the lower tab portion of the second leaflet tab

Example 34

An assembly method according to any example herein, particularly of any of examples 28 to 33, wherein after the stitching of (c) and before the stitching of (g), at least the first part of the upper tab portion of the second leaflet tab and the third part of the lower tab portion of the second leaflet tab are not stitched.

Example 35

An assembly method according to any example herein, particularly example 28, wherein the stitching of (c) is performed after the conveying of (d) or prior to the disposing of (b).

Example 36

An assembly method according to any example herein, particularly any of examples 28 to 35, wherein in the conveying of (d), a dimension along the circumferential direction of a combination of the first wedge member and the upper tab portion of the first leaflet tab is less than a width along the circumferential direction of the upper opening of the commissure window; and wherein after the folding of (f), a dimension along the circumferential direction of a combination of the first wedge member and the upper tab portions of the first and second leaflet tabs is greater than the width along the circumferential direction of the upper opening.

Example 37

An assembly method according to any example herein, particularly any of examples 28 to 36, wherein in the conveying of (d), a dimension along the circumferential direction of a combination of the second wedge member and the lower tab portion of the first leaflet tab is less than a width along the circumferential direction of the lower opening of the commissure window; and wherein after the folding of (f), a dimension along the circumferential direction of a combination of the second wedge member and the lower tab portions of the first and second leaflet tabs is greater than the width along the circumferential direction of the lower opening.

Example 38

An assembly method according to any example herein, particularly any of examples 28 to 37, wherein the disposing the upper tab portion of (b) comprises folding the upper tab portion of the first leaflet tab inserting the first wedge member between facing surfaces of the folded upper tab portion of the first leaflet tab; and/or wherein the disposing the lower tab portion of (b) comprises folding the lower tab portion of the first leaflet tab and inserting the second wedge member between facing surfaces of the folded lower tab portion of the first leaflet tab.

Example 39

An assembly method according to any example herein, particularly any of examples 28 to 38, wherein the disposing the upper tab portion of (b) comprises wrapping the upper tab portion of the first leaflet tab around the first wedge member, and/or the disposing the lower tab portion of (b) comprises wrapping the lower tab portion of the first leaflet tab around the second wedge member.

Example 40

An assembly method according to any example herein, particularly any of examples 28 to 39, wherein the upper and lower openings of the commissure window are disposed to form an H-shape in side view, the H-shaped commissure window has a pair of struts that each extend along the axial direction of the annular frame, and the crossbar extends along a circumferential direction of the annular frame between the pair of struts.

Example 41

An assembly method according to any example herein, particularly example 40, wherein the crossbar is offset from a midpoint of each strut along the axial direction.

Example 42

An assembly method according to any example herein, particularly example 41, wherein each strut has a first end adjacent to the upper opening and a second end adjacent to the lower opening, a distance, $L_1$, along the axial direction from the first end of each strut to a middle of the crossbar along the axial direction is less than a distance, $L_2$, along the axial direction from the middle of the crossbar to the second end of each strut, and $L_1/L_2$ is within a range of 0.25 to 0.35, inclusive.

Example 43

An assembly method according to any example herein, particularly any of examples 28 to 42, wherein in the folding of (d), the stitching together the first wedge member and the upper tab portions is by at least one first suture, and the stitching together the second wedge member and the lower tab portions is by at least one second suture.

Example 44

An assembly method according to any example herein, particularly any of examples 28-43, wherein, in (d), the stitching together the first wedge member and the upper tab portions and the stitching together the second wedge member and the lower tab portions is by a single suture.

Example 45

An assembly method according to any example herein, particularly any of examples 28-44, wherein, after the stitching of (g): the first part of the upper tab portion of the second leaflet tab, the second part of the upper tab portion of the first leaflet tab, the first wedge member, the first part of the upper tab portion of the first leaflet tab, and the second part of the upper tab portion of the second leaflet tab are disposed in order along the circumferential direction and stitched together; and/or the third part of the lower tab portion of the second leaflet tab, the fourth part of the lower tab portion of the first leaflet tab, the second wedge member, the third part of the lower tab portion of the first leaflet tab, and the fourth part of the lower tab portion of the second leaflet tab are disposed in order along the circumferential direction and stitched together.

Example 46

An assembly method according to any example herein, particularly any of examples 28-45, wherein, after the folding of (f): the free ends of the upper tab portions of the first and second leaflet are disposed along the radial direction between the first wedge member and the radially-outer side of the commissure window; and/or the free ends of the lower tab portions of the first and second leaflet tabs are disposed along the radial direction between the second wedge member and the radially-outer side of the commissure window.

Example 47

An assembly method according to any example herein, particularly any of examples 28-46, further comprising: (h) providing a third leaflet for the valvular structure, the third leaflet also having a pair of tabs, one of the tabs being on an opposite side from the other of the tabs with respect to a centerline of the third leaflet, each tab having an upper tab portion and a lower tab portion separated from the upper tab portion along a direction parallel to the centerline by a gap; (i) disposing the upper tab portion of a third tab of the pair of tabs of the third leaflet to surround at least a portion of a circumference of a third wedge member, and disposing the lower tab portion of the third leaflet tab to surround at least a portion of a circumference of a fourth wedge member; (j) stitching together the third wedge member and at least the upper tab portion of the third leaflet tab, and stitching together the fourth wedge member and at least the lower tab portion of the third leaflet tab; (k) conveying the third wedge member, the fourth wedge member, and the third leaflet tab through a second commissure window of the annular frame, the second commissure window having second upper and second lower openings separated from each other along the axial direction by a second crossbar, the conveying being along the radial direction from a radially inner-side of the second commissure window to a radially-outer side of the second commissure window, and such that the upper tab portion of the third leaflet tab and the third wedge member are inserted through the second upper opening and the lower tab portion of the third leaflet tab and the fourth wedge member are inserted through the second lower opening; (l) conveying a fourth tab of the pair of tabs of either the first leaflet or the second leaflet through the second commissure window, the conveying being along the radial direction from the radially inner-side of the second commissure window to the radially-outer side of the second commissure window and such that the upper tab portion of the fourth tab is inserted through the upper opening and the lower tab portion of the fourth tab is inserted through the lower opening; (m) folding the upper tab portion of the fourth tab around the upper tab portion of the third leaflet tab, and folding the lower tab portion of the fourth tab around the lower tab portion of the third leaflet tab; and (n) after (m), stitching together the third wedge member, and the upper tab portions of the third and fourth tabs, and stitching together the fourth wedge member and the lower tab portions of the third and fourth tabs.

Example 48

An assembly method according to any example herein, particularly any of examples 28-47, wherein each wedge member comprises at least one of a braided suture, a braided cable, or a folded piece of cloth.

Example 49

An assembly method according to any example herein, particularly any of examples 28-48, wherein each commissure window is an integral part of the expandable annular frame of the prosthetic heart valve.

Example 50

An assembly method according to any example herein, particularly any of examples 28-48, wherein each commissure window is a part of a respective support member that forms a part of or is coupled to the expandable annular frame of the prosthetic heart valve.

Example 51

An assembly method according to any example herein, particularly example 50, wherein the support member comprises a portion of an actuator or locking mechanism of the prosthetic heart valve, or is coupled to an actuator or locking mechanism of the prosthetic heart valve.

Example 52

An assembly method according to any example herein, particularly any of examples 29-51, wherein one or more of the first through fourth parts includes one or more through-holes therein.

Example 53

An assembly method according to any example herein, particularly example 52, wherein the stitching in (c) comprises passing one or more sutures through the through-holes of the second part of the upper tab portion of the first leaflet tab and of the second part of the upper tab portion of the first leaflet tab, and passing one or more sutures through the through-holes of the fourth part of the lower tab portion of the first leaflet tab and of the fourth part of the lower tab portion of the second leaflet tab.

Example 54

An assembly method according to any example herein, particularly any of examples 52-53, wherein the stitching in (g) comprises passing one or more sutures through the through-holes of the first and second parts of the upper tab portion of the second leaflet tab, and passing one or more sutures through the through-holes of the third and fourth parts of the lower tab portion of the second leaflet tab.

Example 55

An assembly method for a prosthetic heart valve comprises: (a) providing first and second leaflets for a valvular structure of the prosthetic heart valve, each leaflet having a pair of tabs, one of the tabs being on an opposite side from the other of the tabs with respect to a centerline of the leaflet, each tab having an upper tab portion and a lower tab portion separated from the upper tab portion along a direction parallel to the centerline by a gap; (b) conveying a first tab of the pair of tabs of the first leaflet through a commissure window of an expandable annular frame of the prosthetic heart valve, and conveying a second tab of the pair of tabs of the second leaflet through the commissure window, the commissure window having upper and lower openings separated from each other along an axial direction of the annular frame by a crossbar, the conveying being along a radial direction of the annular frame from a radially inner-side of the commissure window to a radially-outer side of the commissure window and such that the upper tab portions are inserted through the upper opening and the lower tab portions are inserted through the lower opening; (c) after (b), disposing the upper and lower tab portions of the first leaflet tab to surround at least a portion of a circumference of one or more wedge members; (d) folding the upper tab portion of the second leaflet tab around the upper tab portion of the first leaflet tab, and folding the lower tab portion of the second leaflet tab around the lower tab portion of the first leaflet tab; and (e) stitching together the one or more wedge members and the upper tab portions of the first and second leaflet tabs, and stitching together the one or more wedge members and the lower tab portions of the first and second leaflet tabs.

Example 56

An assembly method according to any example herein, particularly example 55, wherein: the upper tab portion of each leaflet tab has a first part that is adjacent to a free end of said upper tab portion and a second part that is between the first part and the centerline of the leaflet, and the lower tab portion of each leaflet tab has a third part that is adjacent to a free end of said lower tab portion and a fourth part that is between the third part and the centerline of the leaflet.

Example 57

An assembly method according to any example herein, particularly any of examples 55-56, further comprises: after (c) and prior to (d), stitching together the one or more wedge members and the upper tab portions of the first leaflet tab, and stitching together one or more wedge members and the lower tab portions of the first leaflet tab.

Example 58

An assembly method according to any example herein, particularly example 57, wherein: the stitching together the one or more wedge members and the upper tab portions of the first leaflet tab comprises stitching together the first part of the upper tab portion of the first leaflet tab, the one or more wedge members, and the second part of the upper tab portion of the first leaflet tab; and the stitching together one or more wedge members and the lower tab portions of the first leaflet tab comprises stitching together the third part of the lower tab portion of the first leaflet tab, the one or more wedge members, and the fourth part of the lower tab portion of the first leaflet tab.

Example 59

An assembly method according to any example herein, particularly any of examples 55-58, wherein in (b), the conveying the second leaflet tab through the commissure window occurs simultaneously with the conveying the first leaflet tab through the commissure window.

Example 60

An assembly method according to any example herein, particularly any of examples 55-58, wherein in (b), the conveying the second leaflet tab through the commissure window occurs before or after the conveying the first leaflet tab through the commissure window.

Example 61

An assembly method according to any example herein, particularly any of examples 55-60, wherein, after (d): the first part of the upper tab portion of the second leaflet tab contacts the second part of the upper tab portion of the first leaflet tab, the second part of the upper tab portion of the second leaflet tab contacts the first part of the upper tab portion of the first leaflet tab, the third part of the lower tab portion of the second leaflet tab contacts the fourth part of the lower tab portion of the first leaflet tab, and the fourth part of the lower tab portion of the second leaflet tab contacts the third part of the lower tab portion of the first leaflet tab.

Example 62

An assembly method according to any example herein, particularly example 55, wherein the folding of (d) occurs prior to the disposing of (c).

Example 63

An assembly method according to any example herein, particularly any of examples 55-62, wherein prior to (e), the upper and lower tab portions of the second leaflet tab are not stitched.

Example 64

An assembly method according to any example herein, particularly any of examples 55-63, wherein, after (d): a dimension along the circumferential direction of a combination of the one or more wedge members and the upper tab portions of the first and second leaflet tabs is greater than a width along the circumferential direction of the upper opening, and/or a dimension along the circumferential direction of a combination of the one or more wedge members and the lower tab portions of the first and second leaflet tabs is greater than the width along the circumferential direction of the lower opening.

Example 65

An assembly method according to any example herein, particularly any of examples 55-64, wherein the disposing the upper tab portion of (c) comprises: folding the upper tab portion of the first leaflet tab; and inserting the one or more wedge members between facing surfaces of the folded upper tab portion of the first leaflet tab; and/or wherein the disposing the lower tab portion of (c) comprises: folding the lower tab portion of the first leaflet tab; and inserting the one or more wedge members between facing surfaces of the folded lower tab portion of the first leaflet tab.

Example 66

An assembly method according to any example herein, particularly any of examples 55-65, wherein: the disposing the upper tab portion of (c) comprises wrapping the upper tab portion of the first leaflet tab around the one or more wedge members, and/or the disposing the lower tab portion of (c) comprises wrapping the lower tab portion of the first leaflet tab around the one or more wedge members.

Example 67

An assembly method according to any example herein, particularly any of examples 55-66, wherein the one or more wedge members comprises a single continuous wedge member.

Example 68

An assembly method according to any example herein, particularly any of examples 55-66, wherein the one or more wedge members comprises separate first and second wedge members, the upper tab portion of the first leaflet tab being disposed around the first wedge member, the lower tab portion of the first leaflet tab being disposed around the second wedge member.

Example 69

An assembly method according to any example herein, particularly any of examples 55-68, wherein: the upper and lower openings of the commissure window are disposed to form an H-shape in side view, the H-shaped commissure window has a pair of struts that each extend along the axial direction of the annular frame, and the crossbar extends along a circumferential direction of the annular frame between the pair of struts.

Example 70

An assembly method according to any example herein, particularly example 69, wherein the crossbar is offset from a midpoint of each strut along the axial direction.

Example 71

An assembly method according to any example herein, particularly example 70, wherein: each strut has a first end adjacent to the upper opening and a second end adjacent to the lower opening, a distance, $L_1$, along the axial direction from the first end of each strut to a middle of the crossbar along the axial direction is less than a distance, $L_2$, along the axial direction from the middle of the crossbar to the second end of each strut, and $L_1/L_2$ is within a range of 0.25 to 0.35, inclusive.

Example 72

An assembly method according to any example herein, particularly any of examples 55-71, wherein the stitching in (e) is by at least one first suture.

Example 73

An assembly method according to any example herein, particularly example 72, wherein the at least one first suture is a single first suture that stitches together the one or more wedge members, the upper tab portions of the first and second leaflet tabs, and the lower tab portions of the first and second leaflet tabs.

Example 74

An assembly method according to any example herein, particularly example 72, wherein the at least one first suture is a pair of first sutures, one of the pair of first sutures stitching together the one or more wedge members and the upper tab portions of the first and second leaflet tabs, and the other of the pair of first sutures stitching together the one or more wedge members and the lower tab portions of the first and second leaflet tabs.

Example 75

An assembly method according to any example herein, particularly any of examples 56-74, wherein, after (d): the free ends of the upper tab portions of the first and second leaflet are disposed along the radial direction between the one or more wedge members and the radially-outer side of the commissure window; and/or the free ends of the lower tab portions of the first and second leaflet tabs are disposed along the radial direction between the one or more wedge members and the radially-outer side of the commissure window.

Example 76

An assembly method according to any example herein, particularly any of examples 55-75, further comprises: (f) providing a third leaflet for the valvular structure, the third leaflet also having a pair of tabs, one of the tabs being on an opposite side from the other of the tabs with respect to a centerline of the third leaflet, each tab having an upper tab portion and a lower tab portion separated from the upper tab portion along a direction parallel to the centerline by a gap; (g) conveying the third leaflet tab through a second commissure window of the annular frame, and conveying a fourth tab of the pair of tabs of either the first leaflet or the second leaflet through the second commissure window, the second commissure window having second upper and second lower openings separated from each other along the axial direction by a second crossbar, the conveying being along the radial direction from a radially inner-side of the second commissure window to a radially-outer side of the second commissure window and such that the upper tab portions are inserted through the second upper opening and the lower tab portions are inserted through the second lower opening; (h) after (g), disposing the upper and lower tab portions of the third tab to surround at least a portion of a circumference of one or more second wedge members; (i) folding the upper tab portion of the fourth tab around the upper tab portion of the third tab, and folding the lower tab portion of the fourth tab around the folded lower tab portion of the third tab; and (j) after (i), stitching together the one or more second wedge members and the upper tab portions of the third and fourth tabs, and stitching together the one or more second wedge members and the lower tab portions of the third and fourth tabs.

Example 77

An assembly method according to any example herein, particularly any of examples 55-76, wherein each wedge member comprises at least one of a braided suture, a braided cable, or a folded piece of cloth.

Example 78

An assembly method according to any example herein, particularly any of examples 55-77, wherein each commissure window is an integral part of the expandable annular frame of the prosthetic heart valve.

Example 79

An assembly method according to any example herein, particularly any of examples 55-77, wherein each commissure window is a part of a respective support member that forms a part of or is coupled to the expandable annular frame of the prosthetic heart valve.

Example 80

An assembly method according to any example herein, particularly example 79, wherein the support member comprises a portion of an actuator or locking mechanism of the prosthetic heart valve, or is coupled to an actuator or locking mechanism of the prosthetic heart valve.

Example 81

An assembly method according to any example herein, particularly any of examples 56-79, wherein one or more of the first through fourth parts includes one or more through-holes therein.

Example 82

An assembly method according to any example herein, particularly example 81, wherein the stitching in (e) comprises passing one or more sutures through the through-holes of the first part of the upper tab portion of the second leaflet tab and of the second part of the upper tab portion of the second leaflet tab, and passing one or more sutures through the through-holes of the third part of the lower tab portion of the second leaflet tab and of the fourth part of the lower tab portion of the second leaflet tab.

Example 83

An assembly method for a prosthetic heart valve comprises: (a) providing first and second leaflets for a valvular structure of the prosthetic heart valve, each leaflet having a pair of tabs, one of the tabs being on an opposite side from the other of the tabs with respect to a centerline of the leaflet, each tab having an upper tab portion and a lower tab portion separated from the upper tab portion along a direction parallel to the centerline by a gap; (b) disposing the upper tab portion of a first tab of the pair of tabs of the first leaflet to surround at least a portion of a circumference of a first wedge member; (c) stitching together the first wedge member and at least the upper tab portion of the first leaflet tab; (d) conveying a lower tab portion of the first leaflet tab through a commissure window of an expandable annular frame of the prosthetic heart valve, the commissure window having upper and lower openings separated from each other along an axial direction of the annular frame by a crossbar, the conveying being along a radial direction of the annular frame from a radially-inner side of the commissure window to a radially-outer side of the commissure window and such that the lower tab portion of the first leaflet tab extends through the lower opening; (e) conveying the first wedge member and the upper tab portion of the first leaflet tab from the radially-inner side of the commissure window through or over the upper opening of the commissure window to the radially-outer side of the commissure window, such that the upper tab portion of the first leaflet tab extends through the upper opening; (f) folding the lower tab portion of the first leaflet tab around the first wedge member; (g) conveying a second tab of the pair of tabs of the second leaflet through the commissure window, the conveying being along the radial direction from the radially inner-side of the commissure window to the radially-outer side of the commissure window and such that the upper tab portion of the second leaflet tab is inserted through the upper opening and the lower tab portion of the second leaflet tab is inserted through the lower opening; (h) folding the upper tab portion of the second leaflet tab around the upper tab portion of the first leaflet tab, and folding the lower tab portion of the second leaflet tab around the lower tab portion of the first leaflet tab; and (i) after (h), stitching together the first wedge member and the upper and lower tab portions of the first and second leaflet tabs.

Example 84

An assembly method according to any example herein, particularly example 83, wherein: the upper tab portion of each leaflet tab has a first part that is adjacent to a free end of said upper tab portion and a second part that is between the first part and the centerline of the leaflet, and the lower tab portion of each leaflet tab has a third part that is adjacent to a free end of said lower tab portion and a fourth part that is between the third part and the centerline of the leaflet.

Example 85

An assembly method according to any example herein, particularly any of examples 83-84, further comprises: after (f) and prior to (h), stitching together the first wedge member and the lower tab portion of the first leaflet tab.

Example 86

An assembly method according to any example herein, particularly any of examples 83-85, wherein, in (c), the first wedge member, the upper tab portion of the first leaflet tab, and the upper portion of the second leaflet tab are stitched together, and the conveying of (g) is performed together with the conveying of (d) and/or (e).

Example 87

An assembly method according to any example herein, particularly any of examples 83-85, wherein the conveying of (g) is performed before or with the conveying of (d) and/or (e).

Example 88

An assembly method according to any example herein, particularly any of examples 83-87, wherein the conveying of (e) is performed before or with the conveying of (d).

Example 89

An assembly method according to any example herein, particularly any of examples 83-88, wherein the folding of (f) is performed together with the folding of (h).

Example 90

An assembly method according to any example herein, particularly any of examples 84-89, wherein, after (h): the first part of the upper tab portion of the second leaflet tab contacts the second part of the upper tab portion of the first leaflet tab, the second part of the upper tab portion of the second leaflet tab contacts the first part of the upper tab portion of the first leaflet tab, the third part of the lower tab portion of the second leaflet tab contacts the fourth part of the lower tab portion of the first leaflet tab, and the fourth part of the lower tab portion of the second leaflet tab contacts the third part of the lower tab portion of the first leaflet tab.

Example 91

An assembly method according to any example herein, particularly any of examples 83-90, wherein, after (h): a dimension along the circumferential direction of a combination of the first wedge member and the upper tab portions of the first and second leaflet tabs is greater than a width along the circumferential direction of the upper opening, and/or a dimension along the circumferential direction of a combination of the first wedge member and the lower tab portions of the first and second leaflet tabs is greater than the width along the circumferential direction of the lower opening.

Example 92

An assembly method according to any example herein, particularly any of examples 83-91, wherein the disposing the upper tab portion of (b) comprises: folding the upper tab portion of the first leaflet tab, and inserting the first wedge member between facing surfaces of the folded upper tab portion of the first leaflet tab; or wrapping the upper tab portion of the first leaflet tab around the one or more wedge members.

Example 93

An assembly method according to any example herein, particularly any of examples 83-92, wherein: the upper and lower openings of the commissure window are disposed to form an H-shape in side view, the H-shaped commissure window has a pair of struts that each extend along the axial direction of the annular frame, and the crossbar extends along a circumferential direction of the annular frame between the pair of struts.

Example 94

An assembly method according to any example herein, particularly example 93, wherein the crossbar is offset from a midpoint of each strut along the axial direction.

Example 95

An assembly method according to any example herein, particularly example 94, wherein: each strut has a first end adjacent to the upper opening and a second end adjacent to the lower opening, a distance, $L_1$, along the axial direction from the first end of each strut to a middle of the crossbar along the axial direction is less than a distance, $L_2$, along the axial direction from the middle of the crossbar to the second end of each strut, and $L_1/L_2$ is within a range of 0.25 to 0.35, inclusive.

Example 96

An assembly method according to any example herein, particularly any of examples 83-95, wherein the stitching in (i) is by at least one first suture.

Example 97

An assembly method according to any example herein, particularly example 96, wherein the at least one first suture is a single first suture that stitches together the first wedge member, the upper tab portions of the first and second leaflet tabs, and the lower tab portions of the first and second leaflet tabs.

Example 98

An assembly method according to any example herein, particularly example 96, wherein the at least one first suture is a pair of first sutures, one of the pair of first sutures stitching together the first wedge member and the upper tab portions of the first and second leaflet tabs, and the other of the pair of first sutures stitching together the first wedge member and the lower tab portions of the first and second leaflet tabs.

Example 99

An assembly method according to any example herein, particularly any of examples 84-98, wherein, after (h): the free ends of the upper tab portions of the first and second leaflet are disposed along the radial direction between the first wedge member and the radially-outer side of the commissure window; and the free ends of the lower tab portions of the first and second leaflet tabs are disposed along the radial direction between the first wedge member and the radially-outer side of the commissure window.

Example 100

An assembly method according to any example herein, particularly any of examples 83-99, further comprising: (j) providing a third leaflet for the valvular structure, the third leaflet also having a pair of tabs, one of the tabs being on an opposite side from the other of the tabs with respect to a centerline of the third leaflet, each tab having an upper tab portion and a lower tab portion separated from the upper tab portion along a direction parallel to the centerline by a gap; (k) disposing the upper tab portion of a third tab of the pair of tabs of the third leaflet to surround at least a portion of a circumference of a second wedge member; (l) stitching together the third wedge member and at least the upper tab portion of the third tab; (m) conveying a lower tab portion of the third tab through a second commissure window of the annular frame, the second commissure window having second upper and second lower openings separated from each other along the axial direction by a second crossbar, the conveying being along the radial direction from a radially inner-side of the second commissure window to a radially-outer side of the second commissure window and such that the lower tab portion of the third tab extends through the second lower opening; (n) conveying the second wedge member and the upper tab portion of the third tab from the radially-inner side of the second commissure window through or over the upper opening of the second commissure window to the radially-outer side of the second commissure window, such that the upper tab portion of the third tab extends through the second upper opening; (o) folding the lower tab portion of the third tab around the second wedge member; (p) conveying a fourth tab of the pair of tabs of either the first leaflet or the second leaflet through the second commissure window, the conveying being along the radial direction from the radially inner-side of the second commissure window to the radially-outer side of the second commissure window and such that the upper tab portion of the fourth tab is inserted through the upper opening and the lower tab portion of the fourth tab is inserted through the lower opening; (q) folding the upper tab portion of the fourth tab around the upper tab portion of the third tab, and folding the lower tab portion of the fourth tab around the folded lower tab portion of the third tab; and (r) after (q), stitching together the second wedge member and the upper and lower tab portions of the third and fourth tabs.

Example 101

An assembly method according to any example herein, particularly any of examples 83-100, wherein each wedge member comprises at least one of a braided suture, a braided cable, or a folded piece of cloth.

Example 102

An assembly method according to any example herein, particularly any of examples 83-101, wherein each commissure window is an integral part of the expandable annular frame of the prosthetic heart valve.

Example 103

An assembly method according to any example herein, particularly any of examples 83-101, wherein each commissure window is a part of a respective support member that forms a part of or is coupled to the expandable annular frame of the prosthetic heart valve.

Example 104

An assembly method according to any example herein, particularly example 103, wherein the support member comprises a portion of an actuator or locking mechanism of the prosthetic heart valve, or is coupled to an actuator or locking mechanism of the prosthetic heart valve.

Example 105

An assembly method according to any example herein, particularly any of examples 83-104, wherein one or more of the first through fourth parts includes one or more through-holes therein.

Example 106

An assembly method according to any example herein, particularly example 105, wherein the stitching in (h) comprises passing one or more sutures through the through-holes of the first part of the upper tab portion of the second leaflet tab and of the second part of the upper tab portion of the second leaflet tab, and passing one or more sutures through the through-holes of the third part of the lower tab portion of the second leaflet tab and of the fourth part of the lower tab portion of the second leaflet tab.

Example 107

A prosthetic heart valve comprises: an expandable annular frame having a plurality of commissure windows; and a valvular structure coupled to the commissure windows. The valvular structure comprises a plurality of leaflets. The tabs of adjacent leaflets are coupled to a respective one of the commissure windows according to the assembly method of any of examples 1-106.

Example 108

A prosthetic heart valve comprises: an expandable annular frame having a plurality of commissure windows; and a valvular structure comprising a plurality of leaflets, each leaflet having a pair of tabs, one of the tabs being on an opposite side from the other of the tabs with respect to a centerline of the leaflet, each tab having an upper tab portion and a lower tab portion separated from the upper tab portion along a direction parallel to the centerline by a gap. The valvular structure has a plurality of commissures formed by paired tabs of adjacent leaflets. Each commissure is coupled to a corresponding one of the commissure windows to support the valvular structure within the annular frame. Each commissure window has upper and lower openings separated from each other along an axial direction of the annular frame by a respective crossbar. The upper and lower tab portions for each tab extend through the upper and lower openings, respectively, to a radially-outer side of the respective commissure window. The annular frame is expandable between a crimped state having a first diameter and an expanded state having a second diameter greater than the first diameter.

Example 109

The prosthetic heart valve of any example herein, particularly example 108, further comprises a plurality of wedge members corresponding to the plurality of commissures. Each wedge member is disposed on the radially-outer side of the respective commissure window, with the tabs of the corresponding commissure wrapping around the wedge member.

Example 110

The prosthetic heart valve of any example herein, particularly example 109, wherein each wedge member is coupled to one or more of the wrapped tabs of the corresponding commissure by one or more sutures.

Example 111

The prosthetic heart valve of any example herein, particularly example 108, further comprises: a plurality of first and second wedge members corresponding to the plurality of commissures. Each first wedge member is disposed on the radially-outer side of the respective commissure window, with the upper tab portions of the tabs of the corresponding commissure wrapping around said first wedge member. Each second wedge member is disposed on the radially-outer side of the respective commissure window with the lower tab portions of the tabs of the corresponding commissure wrapping around said second wedge member.

Example 112

The prosthetic heart valve of any example herein, particularly example 111, wherein: each first wedge member is coupled to one or more of the wrapped upper tab portions of the tabs of the corresponding commissure, and each second wedge member is coupled to one or more of the wrapped lower tab portions of the tabs of the corresponding commissure by one or more sutures.

Example 113

The prosthetic heart valve of any example herein, particularly any of examples 109-112, wherein each wedge member comprises at least one of a braided suture, a braided cable, or a folded piece of cloth.

Example 114

The prosthetic heart valve of any example herein, particularly any of examples 108-113, wherein each commissure window is an integral part of the expandable annular frame.

Example 115

The prosthetic heart valve of any example herein, particularly any of examples 108-113, further comprises a plurality of support members that form a part of or are coupled to the expandable annular frame. Each commissure window is a part of a respective one of the support members.

Example 116

The prosthetic heart valve of any example herein, particularly example 115, further comprises an actuator constructed to expand or contract the annular frame, or a locking mechanism constructed to maintain a shape of the annular frame after expansion or contraction thereof. At least one of the support members is a portion of the actuator or locking mechanism, or is coupled to the actuator or locking mechanism.

Example 117

The prosthetic heart valve of any example herein, particularly any of examples 108-116, wherein the upper and lower openings of each commissure window are disposed to form an H-shape in respective side view, each commissure window has a pair of struts, each strut extending along the axial direction of the annular frame, and for each commissure window, the corresponding crossbar extends along a circumferential direction of the annular frame between the pair of struts.

Example 118

The prosthetic heart valve of any example herein, particularly example 117, wherein the crossbar is offset from a midpoint of each strut along the axial direction.

Example 119

The prosthetic heart valve of any example herein, particularly example 118, wherein, for each commissure window: each strut has a first end adjacent to the upper opening and a second end adjacent to the lower opening, a distance, $L_1$, along the axial direction from the first end of each strut to a middle of the crossbar along the axial direction is less than a distance, $L_2$, along the axial direction from the middle of the crossbar to the second end of each strut.

Example 120

The prosthetic heart valve of any example herein, particularly example 119, wherein $L_1/L_2$ is within a range of 0.25 to 0.35, inclusive.

Example 121

The prosthetic heart valve of any example herein, particularly any of examples 107-120, wherein the annular frame comprises a plurality of first struts that are angled with respect to the axial direction so as to extend along a circumferential direction of the annular frame, the first struts connect together at adjacent ends to form an open-cell lattice structure, each cell being open along the radial direction of the annular frame, and the struts of each commissure window are disposed within the lattice structure and coupled to adjacent ones of the first struts.

Example 122

The prosthetic heart valve of any example herein, particularly any of examples 107-121, wherein for each commissure window, each strut has: a first end adjacent to the upper opening and connected to a third end of a respective first angled strut of the annular frame, the first angled strut having a fourth end connected to an adjacent angled strut of the annular frame; and a second end adjacent to the lower opening and connected to a fifth end of a respective second angled strut of the annular frame, the second angled strut having a sixth end connected to another adjacent angled strut of the annular frame. For each commissure window, $(h_1y_2)/(h_2y_1)$ is within a range of 0.8-1.2, inclusive, when the annular frame is at a third diameter midway between the crimped state and the expanded state, where $h_1$ is a distance along the axial direction from the third end to the fourth end of the first angled strut, $h_2$ is a distance along the axial direction from the fifth end to the sixth end of the second angled strut, $y_1$ is a distance along the axial direction from the fourth end to a middle of the crossbar, and $y_2$ is a distance along the axial direction from the sixth end to the middle of the crossbar.

Example 123

The prosthetic heart valve of any example herein, particularly example 122, wherein $(h_1y_2)/(h_2y_1)$ is within a range of 0.9-1.1, inclusive.

Example 124

The prosthetic heart valve of any example herein, particularly example 123, wherein $(h_1y_2)/(h_2y_1)$ is approximately 1.

Example 125

The prosthetic heart valve of any example herein, particularly any of examples 121-124, wherein the annular frame further comprises a plurality of second struts that extend substantially parallel to the axial direction, each second strut being disposed within the lattice structure and coupled to adjacent ones of the first struts.

Example 126

The prosthetic heart valve of any example herein, particularly 125, wherein at least one of the second struts is disposed between a pair of the commissure windows along the circumferential direction of the annular frame.

Example 127

The prosthetic heart valve of any example herein, particularly any of examples 125-126, wherein at equal intervals along the circumferential direction of the annular frame, one of the second struts or one of the commissure windows is disposed within the lattice structure.

Example 128

The prosthetic heart valve of any example herein, particularly any of examples 125-127, wherein each second strut has a width along the circumferential direction that is greater than a width of each first strut.

Example 129

The prosthetic heart valve of any example herein, particularly any of examples 125-128, wherein each second strut has end portions and a middle portion between the end portions along a direction parallel to the axial direction of the annular frame, a width of the middle portion along the circumferential direction being less than that of the end portions.

Example 130

The prosthetic heart valve of any example herein, particularly any of examples 125-129, wherein each second strut has a dog-bone shape in respective side view that complements a shape of a facing strut of one of the commissure windows when the annular frame is in a crimped configuration.

Example 131

The prosthetic heart valve of any example herein, particularly any of examples 121-130, wherein the struts of each commissure window have widths along the circumferential direction greater than respective widths of the first struts.

Example 132

The prosthetic heart valve of any example herein, particularly any of examples 121-131, wherein the commissure windows and the lattice structure are constructed such that, for each commissure window: a first distance along the circumferential direction between the struts at their first ends remains substantially the same in the deployed state as in the crimped state, and/or a second distance along the circumferential direction between the struts at their second ends remains substantially the same in the deployed state as in the crimped state.

Example 133

The prosthetic heart valve of any example herein, particularly any of examples 107-132, wherein the annular frame has an inflow end and an outflow end, and the upper opening of each commissure window is disposed between the outflow end and the lower opening along the axial direction.

Example 134

The prosthetic heart valve of any example herein, particularly example 133, wherein the lattice structure is constructed such that: the upper opening of each commissure window opens to the outflow end of the annular frame along a direction parallel to the axial direction of the annular frame, and/or the lower opening of each commissure window opens along a direction parallel to the axial direction of the annular frame to a respective one of the cells of the lattice structure that is closed to the inflow end of the annular frame by one of the first struts or a joint between adjacent first struts that form said one of the cells.

Example 135

The prosthetic heart valve of any example herein, particularly any of examples 133-134, wherein an open area of one of the cells formed adjacent to the outflow end of the annular frame is greater than an open area of one of the cells formed adjacent to the inflow end of the annular frame.

Example 136

The prosthetic heart valve of any example herein, particularly any of examples 117-135, wherein, for each commissure window, a maximum width of each strut along the circumferential direction is at a portion between the first and second ends of the strut.

Example 137

The prosthetic heart valve of any example herein, particularly any of examples 107-136, wherein the valvular structure is a bicuspid structure with two leaflets and two commissures, and the annular frame has two commissure windows on diametrically opposite sides from each other.

Example 138

The prosthetic heart valve of any example herein, particularly any of examples 107-136, wherein the valvular structure is a tricuspid structure with three leaflets and three commissures, and the annular frame has three commissure windows equally spaced along a circumferential direction of the annular frame.

Example 139

The prosthetic heart valve of any example herein, particularly any of examples 107-138, wherein the annular frame is formed of a plastically-expandable material or a self-expanding material.

Example 140

The prosthetic heart valve of any example herein, particularly any of examples 108-116, wherein at least one of the commissure windows comprises: a first strut and a second strut extending along the axial direction of the annular frame and spaced apart from each other in a circumferential direction of the annular frame, each of the first strut and the second strut having first and second ends spaced apart along an axial direction of the annular frame; a first lateral strut portion connected to the first ends of the first strut and the second strut; and a second lateral strut portion connected to the second ends of the first strut and the second strut. The crossbar of the at least one of the commissure windows is connected to the first and second struts and positioned between the first and second lateral strut portions. The upper opening of the at least one of the commissure windows is defined between the first and second struts, the first lateral strut portion, and the crossbar. The lower opening of the at least one of the commissure windows is defined between the first and second struts, the second lateral strut portion, and the crossbar.

Example 141

The prosthetic heart valve of any example herein, particularly example 140, wherein a ratio of a first distance measured from the first lateral strut portion to a midline of the crossbar to a second distance measured from the second lateral strut portion to the midline of the crossbar is in a range from 1 to 3.

Example 142

A delivery assembly comprises a delivery apparatus having a handle at a proximal end thereof and a prosthetic heart valve according to any of examples 108-141 coupled to a distal end portion of the delivery apparatus.

Example 143

A method comprises inserting the prosthetic heart valve according to any of examples 108-141 and 144-146 into a body of a patient, wherein the prosthetic heart valve is inserted with the annular frame in a crimped configuration. The method comprises advancing the prosthetic heart valve to an implantation site within the body of the patient. The method includes radially expanding the prosthetic heart valve to a functional size at the implantation site.

Example 144

A prosthetic heart valve comprises an expandable annular frame having a first window strut portion and a second window strut portion extending in an axial direction of the frame and a crossbar extending in a circumferential direction of the frame and connected at opposite ends to the first and second window strut portions. The crossbar and the first and second window strut portions define a commissure window having an H-shape. The commissure window has a first commissure window portion upstream of the crossbar and a second commissure window downstream of the crossbar. The prosthetic heart valve further comprises a valvular structure disposed within the expandable annular frame. The valvular structure comprises a first leaflet and a second leaflet. The first leaflet has a first tab on a first side edge thereof, and the second leaflet has a second tab on a second side edge thereof. The first tab and the second tab extend through at least one of the first and second commissure window portions to form at least a portion of a commissure that couples the first leaflet and the second leaflet to the expandable annular frame.

Example 145

The prosthetic heart valve of any example herein, particularly example 144, wherein each of the first tab and the second tab comprises a first tab portion and a second tab portion, wherein the first tab portions of the first tab and the second tab extend through the first commissure window portion to form a first portion of the commissure, and wherein the second tab portions of the first tab and the second tab extend through the second commissure window portion to form a second portion of the commissure.

Example 146

The prosthetic heart valve of any example herein, particularly any one of examples 144 and 145, further comprises a first lateral strut portion disposed upstream of the crossbar and connected at opposite ends to the first and second window strut portions and a second lateral strut portion disposed downstream of the crossbar and connected at opposite ends to the first and second window strut portions. The first lateral strut portion forms a closed end of the first commissure window portion. The second lateral strut portion forms a closed end of the second commissure window portion.

Example 147

A prosthetic heart valve comprises an expandable annular frame having a plurality of commissure windows and a valvular structure comprising a plurality of leaflets. Each leaflet has a pair of tabs, one of the tabs being on an opposite side from the other of the tabs with respect to a centerline of the leaflet. Each tab has an upper tab portion and a lower tab portion. The valvular structure has a plurality of commissures formed by paired tabs of adjacent leaflets. Each commissure is coupled to a corresponding one of the commissure windows to support the valvular structure within the annular frame. Each commissure window has upper and lower openings separated from each other along an axial direction of the annular frame by a respective crossbar. The upper and lower tab portions for each tab extend through the upper and lower openings, respectively, to a radially-outer side of the respective commissure window. The annular frame is expandable between a crimped state having a first diameter and an expanded state having a second diameter greater than the first diameter.

Example 148

An assembly method for a prosthetic heart valve comprises providing first and second leaflets for a valvular structure of the prosthetic heart valve, each leaflet having a pair of tabs, one of the tabs being on an opposite side from the other of the tabs with respect to a centerline of the leaflet, each tab having an upper tab portion and a lower tab portion. The method comprises disposing the upper and lower tab portions of a second tab of the pair of tabs of the second leaflet adjacent to the upper and lower tab portions of a first tab of the pair of tabs of the first leaflet, respectively. The method comprises conveying the first and second leaflet tabs through a commissure window of an expandable annular frame of the prosthetic heart valve, the commissure window having upper and lower openings separated from each other along an axial direction of the annular frame by a crossbar, the conveying being along a radial direction of the annular frame from a radially inner-side of the commissure window to a radially-outer side of the commissure window and such that the upper tab portions are inserted through the upper opening and the lower tab portions are inserted through the lower opening. The method further comprises securing the first and second leaflet tabs on the radially-outer side of the commissure window.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A prosthetic heart valve comprising:
an expandable annular frame having a plurality of commissure windows; and
a valvular structure comprising a plurality of leaflets, each leaflet having a pair of tabs, one of the tabs being on an opposite side from the other of the tabs with respect to a centerline of the leaflet, each tab having an upper tab portion and a lower tab portion;
wherein the valvular structure has a plurality of commissures formed by paired tabs of adjacent leaflets, each commissure being coupled to a corresponding one of the commissure windows to support the valvular structure within the annular frame;
wherein each commissure window has upper and lower openings separated from each other along an axial direction of the annular frame by a respective crossbar;
wherein the upper and lower tab portions for each tab extend through the upper and lower openings, respectively, to a radially-outer side of the respective commissure window; and
wherein the annular frame is expandable between a crimped state having a first diameter and an expanded state having a second diameter greater than the first diameter.

2. The prosthetic heart valve of claim 1, further comprising:

a plurality of wedge members corresponding to the plurality of commissures, each wedge member being disposed on the radially-outer side of the respective commissure window, with the tabs of the corresponding commissure wrapping around said wedge member.

3. The prosthetic heart valve of claim 2, wherein each wedge member comprises at least one of a braided suture, a braided cable, or a folded piece of cloth.

4. The prosthetic heart valve of claim 1, further comprising:
a plurality of first and second wedge members corresponding to the plurality of commissures;
wherein each first wedge member is disposed on the radially-outer side of the respective commissure window, with the upper tab portions of the tabs of the corresponding commissure wrapping around said first wedge member; and
wherein each second wedge member is disposed on the radially-outer side of the respective commissure window with the lower tab portions of the tabs of the corresponding commissure wrapping around said second wedge member.

5. The prosthetic heart valve of claim 1, wherein each commissure window is an integral part of the expandable annular frame.

6. The prosthetic heart valve of claim 1, further comprising:
a plurality of support members that form a part of or are coupled to the expandable annular frame, wherein each commissure window is a part of a respective one of the support members; and
an actuator constructed to expand or contract the annular frame or a locking mechanism constructed to maintain a shape of the annular frame after expansion or contraction thereof;
wherein at least one of the support members is a portion of the actuator or locking mechanism or is coupled to the actuator or locking mechanism.

7. The prosthetic heart valve of claim 1, wherein:
the upper and lower openings of each commissure window are disposed to form an H-shape in respective side view,
each commissure window has a pair of struts, each strut extending along the axial direction of the annular frame, and
for each commissure window, the corresponding crossbar extends along a circumferential direction of the annular frame between the pair of struts.

8. The prosthetic heart valve of claim 7, wherein:
the crossbar is offset from a midpoint of each strut along the axial direction;
for each commissure window, each strut has a first end adjacent to the upper opening and a second end adjacent to the lower opening, a distance, $L_1$, along the axial direction from the first end of each strut to a middle of the crossbar along the axial direction is less than a distance, $L_2$, along the axial direction from the middle of the crossbar to the second end of each strut; and
a ratio $L_1/L_2$ is within a range of 0.25 to 0.35, inclusive.

9. The prosthetic heart valve of claim 1, wherein:
the annular frame comprises a plurality of first struts that are angled with respect to the axial direction so as to extend along a circumferential direction of the annular frame, the first struts connect together at adjacent ends to form an open-cell lattice structure, each cell being open along the radial direction of the annular frame, and the struts of each commissure window are disposed within the lattice structure and coupled to adjacent ones of the first struts.

10. The prosthetic heart valve of claim 1, wherein:

the annular frame comprises a plurality of first struts that are angled with respect to the axial direction so as to extend along a circumferential direction of the annular frame, the first struts connect together at adjacent ends to form an open-cell lattice structure, each cell being open along the radial direction of the annular frame, and the struts of each commissure window are disposed within the lattice structure and coupled to adjacent ones of the first struts.

11. The prosthetic heart valve of claim 10, wherein the annular frame further comprises a plurality of second struts that extend substantially parallel to the axial direction, each second strut being disposed within the lattice structure and coupled to adjacent ones of the first struts, and wherein at least one of the second struts is disposed between a pair of the commissure windows along the circumferential direction of the annular frame.

12. The prosthetic heart valve of claim 1, wherein:

for each commissure window, each strut has:

a first end adjacent to the upper opening and connected to a third end of a respective first angled strut of the annular frame, the first angled strut having a fourth end connected to an adjacent angled strut of the annular frame; and a second end adjacent to the lower opening and connected to a fifth end of a respective second angled strut of the annular frame, the second angled strut having a sixth end connected to another adjacent angled strut of the annular frame; and for each commissure window, $(h_1 \times y_2)/(h_2 \times y_1)$ is within a range of 0.8-1.2, inclusive, when the annular frame is at a third diameter midway between the crimped state and the expanded state, where $h_1$ is a distance along the axial direction from the third end to the fourth end of the first angled strut, $h_2$ is a distance along the axial direction from the fifth end to the sixth end of the second angled strut, $y_1$ is a distance along the axial direction from the fourth end to a middle of the crossbar, and $y_2$ is a distance along the axial direction from the sixth end to the middle of the crossbar.

13. The prosthetic heart valve of claim 1, wherein at least one of the commissure windows comprises:

a first strut and a second strut extending along the axial direction of the annular frame and spaced apart from each other in a circumferential direction of the annular frame, each of the first strut and the second strut having first and second ends spaced apart along the axial direction of the annular frame;

a first lateral strut portion connected to the first ends of the first strut and the second strut;

a second lateral strut portion connected to the second ends of the first strut and the second strut;

wherein the crossbar of the at least one of the commissure windows is connected to the first and second struts and positioned between the first and second lateral strut portions;

wherein the upper opening of the at least one of the commissure windows is defined between the first and second struts, the first lateral strut portion, and the crossbar; and wherein the lower opening of the at least one of the commissure windows is defined between the first and second struts, the second lateral strut portion, and the crossbar.

14. The prosthetic heart valve of claim 13, wherein a ratio of a first distance measured from the first lateral strut portion to a midline of the crossbar to a second distance measured from the second lateral strut portion to the midline of the crossbar is in a range from 1 to 3.

15. The prosthetic heart valve of claim 1, wherein the annular frame has an inflow end and an outflow end, and wherein the upper opening of each commissure window is disposed between the outflow end and the lower opening along the axial direction.

16. A delivery assembly comprising:

a delivery apparatus having a handle at a proximal end thereof;

a prosthetic heart valve according to claim 1 coupled to a distal end portion of the delivery apparatus.

17. A prosthetic heart valve comprising:

an expandable annular frame having a first window strut portion and a second window strut portion extending in an axial direction of the frame and a crossbar extending in a circumferential direction of the frame and connected at opposite ends to the first and second window strut portions, the crossbar and the first and second window strut portions defining a commissure window having an H-shape, the commissure window having a first commissure window portion upstream of the crossbar and a second commissure window portion downstream of the crossbar; and a valvular structure disposed within the expandable annular frame, the valvular structure comprising a first leaflet and a second leaflet, the first leaflet having a first tab on a first side edge thereof, the second leaflet having a second tab on a second side edge thereof, the first tab and the second tab extending through at least one of the first and second commissure window portions to form at least a portion of a commissure that couples the first leaflet and the second leaflet to the expandable annular frame.

18. The prosthetic heart valve of claim 17, wherein each of the first tab and the second tab comprises a first tab portion and a second tab portion, wherein the first tab portions of the first tab and the second tab extend through the first commissure window portion to form a first portion of the commissure, and wherein the second tab portions of the first tab and the second tab extend through the second commissure window portion to form a second portion of the commissure.

19. The prosthetic heart valve of claim 17, further comprising:

a first lateral strut portion disposed upstream of the crossbar and connected at opposite ends to the first and second window strut portions, the first lateral strut portion forming a closed end of the first commissure window portion; and a second lateral strut portion disposed downstream of the crossbar and connected at opposite ends to the first and second window strut portions, the second lateral strut portion forming a closed end of the second commissure window portion.

20. An assembly method for a prosthetic heart valve, the method comprising:

providing first and second leaflets for a valvular structure of the prosthetic heart valve, each leaflet having a pair of tabs, one of the tabs being on an opposite side from the other of the tabs with respect to a centerline of the leaflet, each tab having an upper tab portion and a lower tab portion;

disposing the upper and lower tab portions of a second tab of the pair of tabs of the second leaflet adjacent to the upper and lower tab portions of a first tab of the pair of tabs of the first leaflet, respectively;

conveying the first and second leaflet tabs through a commissure window of an expandable annular frame of the prosthetic heart valve, the commissure window having upper and lower openings separated from each other along an axial direction of the annular frame by a crossbar, the conveying being along a radial direction of the annular frame from a radially inner-side of the commissure window to a radially-outer side of the commissure window and such that the upper tab portions are inserted through the upper opening and the lower tab portions are inserted through the lower opening; and securing the first and second leaflet tabs on the radially-outer side of the commissure window.

21. The method of claim 20, wherein the upper and lower openings of the commissure window are disposed to form an H-shape in side view, the H-shaped commissure window has a pair of struts that each extend along the axial direction of the annular frame, and the crossbar extends along a circumferential direction of the annular frame between the pair of struts.

* * * * *